United States Patent
Tanaka et al.

(10) Patent No.: US 11,871,968 B2
(45) Date of Patent: Jan. 16, 2024

(54) SPINAL FIXATION ACCESS AND DELIVERY SYSTEM

(71) Applicant: Providence Medical Technology, Inc., Pleasanton, CA (US)

(72) Inventors: Shigeru Tanaka, Half Moon Bay, CA (US); Christopher U. Phan, Dublin, CA (US); Christopher Lambert, Concord, CA (US); Nicholas Domek, Walnut Creek, CA (US); Bon Champ, Campbell, CA (US); Edward Liou, Pleasanton, CA (US)

(73) Assignee: Providence Medical Technology, Inc., Pleasanton, CA (US)

( * ) Notice: Subject to any disclaimer, the term of this patent is extended or adjusted under 35 U.S.C. 154(b) by 159 days.

(21) Appl. No.: 16/614,888

(22) PCT Filed: May 18, 2018

(86) PCT No.: PCT/US2018/033505
§ 371 (c)(1),
(2) Date: Nov. 19, 2019

(87) PCT Pub. No.: WO2018/213779
PCT Pub. Date: Nov. 22, 2018

(65) Prior Publication Data
US 2020/0155205 A1 May 21, 2020

Related U.S. Application Data

(60) Provisional application No. 62/508,434, filed on May 19, 2017.

(51) Int. Cl.
*A61B 17/70* (2006.01)
*A61B 90/00* (2016.01)
(Continued)

(52) U.S. Cl.
CPC ...... *A61B 17/7064* (2013.01); *A61B 17/7032* (2013.01); *A61B 17/7037* (2013.01);
(Continued)

(58) Field of Classification Search
CPC ...... A61B 17/70; A61B 17/7062–7071; A61B 17/7076; A61B 17/7083–7085;
(Continued)

(56) References Cited

U.S. PATENT DOCUMENTS 1,934,962 A  11/1933  Barry
2,708,376 A   5/1955  Booth
(Continued)

FOREIGN PATENT DOCUMENTS

DE   G9304368.6 U1   5/2003
FR     2722980 A1    2/1996
(Continued)

OTHER PUBLICATIONS

US 7,063,700 B2, 06/2006, Michelson (withdrawn)
(Continued)

*Primary Examiner* — Eduardo C Robert
*Assistant Examiner* — Michelle C Eckman
(74) *Attorney, Agent, or Firm* — Dorsey & Whitney LLP

(57) ABSTRACT

A spinal fixation access and delivery system is disclosed. In some aspects, the system is used to access the cervical facet joint via a posterior access approach. The system may include an access device including a body having a proximal portion and a distal portion and a chamfered or beveled end feature positioned at the distal portion of the body and configured for insertion at the cervical facet joint. The system may further include a guide device having access device engagement features and a spinal fixation member.

(Continued)

The access device includes at least one guide device receiving feature complementary to or keyed to the engagement feature of the guide device.

10 Claims, 70 Drawing Sheets

(51) Int. Cl.
    *A61B 17/16*         (2006.01)
    *A61B 17/02*         (2006.01)

(52) U.S. Cl.
    CPC ...... *A61B 17/7076* (2013.01); *A61B 17/7086* (2013.01); *A61B 17/1671* (2013.01); *A61B 2017/0256* (2013.01); *A61B 2090/036* (2016.02)

(58) Field of Classification Search
    CPC ............ A61B 17/1659; A61B 17/1671; A61B 2017/0256; A61B 17/025; A61B 17/885–885
    See application file for complete search history.

(56)                 References Cited

U.S. PATENT DOCUMENTS

| | | |
|---|---|---|
| 2,984,241 A | 5/1961 | Carlson |
| 3,486,505 A | 12/1969 | Morrison |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,192,327 A | 3/1993 | Brantigan |
| 5,236,460 A | 8/1993 | Barber |
| 5,443,514 A | 8/1995 | Steffee |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,109 A | 11/1996 | Bertagnoli |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,906,616 A | 5/1999 | Pavlov et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa et al. |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,174,311 B1 | 1/2001 | Branch et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,200,322 B1 | 3/2001 | Branch et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| 6,248,345 B1 | 6/2001 | Goldenheim et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,485,518 B1 | 11/2002 | Cornwall et al. |
| 6,500,206 B1 | 12/2002 | Bryan |
| 6,514,256 B2 | 2/2003 | Zucherman et al. |
| 6,524,312 B2 | 2/2003 | Landry et al. |
| 6,530,955 B2 | 3/2003 | Boyle et al. |
| 6,537,279 B1 | 3/2003 | Michelson |
| 6,540,747 B1 | 4/2003 | Marino |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,899 B1 | 6/2003 | Foley et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,582,467 B1 | 6/2003 | Teitelbaum et al. |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |

(56) References Cited

U.S. PATENT DOCUMENTS

| | | |
|---|---|---|
| 6,719,773 B1 | 4/2004 | Boucher et al. |
| 6,719,794 B2 | 4/2004 | Gerber et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,814,738 B2 | 11/2004 | Naughton et al. |
| 6,823,871 B2 | 11/2004 | Schmieding |
| 6,840,941 B2 | 1/2005 | Rogers et al. |
| 6,851,430 B2 | 2/2005 | Tsou |
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,255,703 B2 | 8/2007 | Mujwid et al. |
| 7,261,739 B2 | 8/2007 | Ralph et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,491,240 B1 | 2/2009 | Carver et al. |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,509 B2 | 1/2010 | Stark |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,708,766 B2 | 5/2010 | Anderson et al. |
| 7,722,619 B2 | 5/2010 | Michelson |
| D619,719 S | 7/2010 | Pannu |
| D620,113 S | 7/2010 | Courtney et al. |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,942,903 B2 | 5/2011 | Moskowitz et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,299 B2 | 11/2011 | McGahan et al. |
| 8,062,303 B2 | 11/2011 | Berry et al. |
| 8,066,705 B2 | 11/2011 | Michelson |
| D650,481 S | 12/2011 | Gottlieb et al. |
| 8,092,475 B2 | 1/2012 | Cotter et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |

(56) References Cited

U.S. PATENT DOCUMENTS

| | | |
|---|---|---|
| 8,267,966 B2 | 9/2012 | McCormack et al. |
| 8,333,804 B1 | 12/2012 | Wensel |
| D674,900 S | 1/2013 | Janice et al. |
| 8,348,979 B2 | 1/2013 | McCormack |
| 8,361,152 B2 | 1/2013 | McCormack et al. |
| 8,366,747 B2 | 2/2013 | Shluzas |
| 8,366,748 B2 | 2/2013 | Kleiner |
| 8,382,767 B2 | 2/2013 | Wassinger et al. |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,439,922 B1 * | 5/2013 | Arnold .............. A61B 17/7086 606/279 |
| 8,512,347 B2 | 8/2013 | McCormack et al. |
| 8,523,908 B2 | 9/2013 | Malone |
| 8,529,609 B2 | 9/2013 | Helgerson et al. |
| 8,623,054 B2 | 1/2014 | McCormack et al. |
| 8,668,722 B2 | 3/2014 | Pavlov et al. |
| 8,753,345 B2 | 6/2014 | McCormack et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |
| 9,005,288 B2 | 4/2015 | McCormack et al. |
| 9,011,492 B2 | 4/2015 | McCormack et al. |
| 9,039,766 B1 | 5/2015 | Fonte |
| D732,667 S | 6/2015 | McCormack et al. |
| 9,186,193 B2 | 11/2015 | Kleiner et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg, Jr. et al. |
| 9,271,765 B2 | 3/2016 | Blain |
| 9,333,086 B2 | 5/2016 | McCormack et al. |
| 9,339,263 B2 | 5/2016 | Fenn et al. |
| 9,358,127 B2 | 6/2016 | Duffield et al. |
| 9,381,049 B2 | 7/2016 | McCormack et al. |
| 9,427,264 B2 | 8/2016 | Kleiner et al. |
| 9,504,583 B2 | 11/2016 | Blain |
| 9,622,791 B2 | 4/2017 | McCormack et al. |
| 9,622,873 B2 | 4/2017 | McCormack et al. |
| 9,622,874 B2 | 4/2017 | McCormack et al. |
| 9,629,665 B2 | 4/2017 | McCormack et al. |
| 9,707,650 B2 | 7/2017 | Tiefenbock |
| 9,717,403 B2 | 8/2017 | Kleiner et al. |
| 9,937,053 B2 | 4/2018 | Melkent et al. |
| 10,039,649 B2 | 8/2018 | McCormack et al. |
| 10,149,673 B2 | 12/2018 | McCormack et al. |
| 10,172,721 B2 | 1/2019 | McCormack et al. |
| D841,165 S | 2/2019 | McCormack et al. |
| D841,167 S | 2/2019 | Ricca et al. |
| 10,201,375 B2 | 2/2019 | McCormack et al. |
| 10,206,787 B2 | 2/2019 | Voellmicke |
| 10,219,910 B2 | 3/2019 | McCormack et al. |
| 10,226,285 B2 | 3/2019 | McCormack et al. |
| 10,238,501 B2 | 3/2019 | McCormack et al. |
| 10,327,913 B2 | 6/2019 | Palmatier et al. |
| 10,456,175 B2 | 10/2019 | McCormack et al. |
| 10,568,666 B2 | 2/2020 | McCormack et al. |
| 10,588,672 B2 | 3/2020 | McCormack et al. |
| D884,895 S | 5/2020 | McCormack et al. |
| D887,552 S | 6/2020 | Tanaka et al. |
| 10,682,243 B2 | 6/2020 | Phan et al. |
| D911,525 S | 2/2021 | Tanaka et al. |
| 10,907,417 B2 | 2/2021 | Brady |
| RE48,501 E | 4/2021 | McCormack et al. |
| 11,272,964 B2 | 3/2022 | Mccormack et al. |
| 11,285,010 B2 | 3/2022 | Mccormack |
| 11,648,128 B2 | 5/2023 | Tanaka et al. |
| 2001/0004710 A1 | 6/2001 | Felt et al. |
| 2001/0007074 A1 | 7/2001 | Strobel et al. |
| 2001/0047208 A1 | 11/2001 | Michelson |
| 2001/0053914 A1 | 12/2001 | Landry et al. |
| 2002/0026195 A1 | 2/2002 | Layne et al. |
| 2002/0068941 A1 | 6/2002 | Hanson et al. |
| 2002/0077641 A1 | 6/2002 | Michelson |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0165612 A1 | 11/2002 | Gerber et al. |
| 2002/0169471 A1 | 11/2002 | Ferdinand |
| 2002/0177866 A1 | 11/2002 | Weikel et al. |
| 2003/0023312 A1 | 1/2003 | Thalgott |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0040801 A1 | 2/2003 | Ralph et al. |
| 2003/0077134 A1 | 4/2003 | Moser et al. |
| 2003/0083668 A1 | 5/2003 | Rogers et al. |
| 2003/0083688 A1 | 5/2003 | Simonson |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0149438 A1 | 8/2003 | Nichols et al. |
| 2003/0158553 A1 | 8/2003 | Michelson |
| 2003/0225416 A1 | 12/2003 | Bonvallet et al. |
| 2004/0010259 A1 | 1/2004 | Keller et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2004/0225292 A1 | 11/2004 | Sasso et al. |
| 2004/0254575 A1 | 12/2004 | Obenchain et al. |
| 2005/0010294 A1 | 1/2005 | Michelson |
| 2005/0015097 A1 | 1/2005 | Mujwid et al. |
| 2005/0015149 A1 | 1/2005 | Michelson |
| 2005/0021042 A1 | 1/2005 | Marnay et al. |
| 2005/0027358 A1 | 2/2005 | Suddaby |
| 2005/0033432 A1 | 2/2005 | Gordon et al. |
| 2005/0038511 A1 | 2/2005 | Martz et al. |
| 2005/0049623 A1 | 3/2005 | Moore et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0085912 A1 | 4/2005 | Arnin et al. |
| 2005/0090829 A1 | 4/2005 | Martz et al. |
| 2005/0090901 A1 | 4/2005 | Studer |
| 2005/0113842 A1 | 5/2005 | Bertagnoli et al. |
| 2005/0119680 A1 | 6/2005 | Dykes |
| 2005/0124993 A1 | 6/2005 | Chappuis |
| 2005/0143818 A1 | 6/2005 | Yuan et al. |
| 2005/0149192 A1 | 7/2005 | Zucherman et al. |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0209698 A1 | 9/2005 | Gordon et al. |
| 2005/0216018 A1 | 9/2005 | Sennett |
| 2005/0234455 A1 | 10/2005 | Binder et al. |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0251260 A1 | 11/2005 | Gerber et al. |
| 2005/0267480 A1 | 12/2005 | Suddaby |
| 2006/0004367 A1 | 1/2006 | Alamin et al. |
| 2006/0004448 A1 | 1/2006 | Casey |
| 2006/0015184 A1 | 1/2006 | Winterbottom et al. |

(56) References Cited

U.S. PATENT DOCUMENTS

| | | |
|---|---|---|
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058790 A1 | 3/2006 | Carl et al. |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149279 A1 | 7/2006 | Mathews |
| 2006/0149289 A1 | 7/2006 | Winslow et al. |
| 2006/0184172 A1 | 8/2006 | Michelson |
| 2006/0189991 A1 | 8/2006 | Bickley |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0229627 A1 | 10/2006 | Hunt et al. |
| 2006/0235306 A1 | 10/2006 | Cotter et al. |
| 2006/0235391 A1 | 10/2006 | Sutterlin |
| 2006/0235414 A1 | 10/2006 | Lim et al. |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0162138 A1 | 7/2007 | Heinz |
| 2007/0179617 A1 | 8/2007 | Brown et al. |
| 2007/0179619 A1 | 8/2007 | Grob et al. |
| 2007/0191861 A1 | 8/2007 | Allard et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0250167 A1 | 10/2007 | Bray et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0293949 A1 | 12/2007 | Salerni et al. |
| 2007/0299451 A1 | 12/2007 | Tulkis |
| 2008/0015581 A1 | 1/2008 | Eckman |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0071375 A1 | 3/2008 | Carver et al. |
| 2008/0077245 A1 | 3/2008 | Lee |
| 2008/0091269 A1 | 4/2008 | Zipnick et al. |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0154377 A1 | 6/2008 | Voellmicke |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0183209 A1 | 7/2008 | Robinson et al. |
| 2008/0195206 A1 | 8/2008 | Chee et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0249571 A1 | 10/2008 | Sasso et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275455 A1 | 11/2008 | Berry et al. |
| 2008/0287955 A1 | 11/2008 | Michelson |
| 2008/0300685 A1 | 12/2008 | Carls et al. |
| 2008/0306537 A1 | 12/2008 | Culbert |
| 2008/0312744 A1 | 12/2008 | Vresilovic et al. |
| 2009/0036927 A1 | 2/2009 | Vestgaarden |
| 2009/0131986 A1 | 5/2009 | Lee et al. |
| 2009/0138053 A1 | 5/2009 | Assell et al. |
| 2009/0177205 A1 * | 7/2009 | McCormack ...... A61B 17/1604 606/90 |
| 2009/0177215 A1 | 7/2009 | Stack et al. |
| 2009/0177237 A1 | 7/2009 | Zucherman et al. |
| 2009/0182429 A1 | 7/2009 | Humphreys et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0297603 A1 | 12/2009 | Joshi |
| 2009/0306671 A1 | 12/2009 | McCormack et al. |
| 2009/0312763 A1 | 12/2009 | McCormack et al. |
| 2010/0036418 A1 | 2/2010 | Siemionow et al. |
| 2010/0069912 A1 * | 3/2010 | McCormack ........ A61B 17/025 606/90 |
| 2010/0082065 A1 | 4/2010 | Butler et al. |
| 2010/0086185 A1 | 4/2010 | Weiss |
| 2010/0093829 A1 | 4/2010 | Gorman |
| 2010/0111829 A1 | 5/2010 | Drapeau et al. |
| 2010/0114318 A1 | 5/2010 | Gittings et al. |
| 2010/0145391 A1 | 6/2010 | Kleiner |
| 2010/0145459 A1 | 6/2010 | Mcdonough et al. |
| 2010/0161057 A1 | 6/2010 | Berry et al. |
| 2010/0191241 A1 | 7/2010 | McCormack et al. |
| 2010/0211104 A1 | 8/2010 | Moumene et al. |
| 2010/0286783 A1 | 11/2010 | Lechmann et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0184470 A1 | 7/2011 | Gorek et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |

(56) References Cited

U.S. PATENT DOCUMENTS

| | | | |
|---|---|---|---|
| 2012/0029545 A1* | 2/2012 | Nelson | A61B 17/1659 606/171 |
| 2012/0065613 A1 | 3/2012 | Pepper et al. | |
| 2012/0130496 A1 | 5/2012 | Duffield et al. | |
| 2012/0143334 A1 | 6/2012 | Boyce et al. | |
| 2012/0179259 A1 | 7/2012 | Mcdonough et al. | |
| 2012/0215259 A1* | 8/2012 | Cannestra | A61B 17/7064 606/279 |
| 2012/0245637 A1 | 9/2012 | Kraus et al. | |
| 2012/0245689 A1 | 9/2012 | Gimbel et al. | |
| 2012/0265250 A1 | 10/2012 | Ali | |
| 2012/0277801 A1* | 11/2012 | Marik | A61F 2/4405 606/279 |
| 2012/0283776 A1 | 11/2012 | Mishra | |
| 2012/0296431 A1 | 11/2012 | Kim et al. | |
| 2012/0323242 A1 | 12/2012 | Tsuang et al. | |
| 2013/0006364 A1 | 1/2013 | McCormack et al. | |
| 2013/0012994 A1 | 1/2013 | McCormack et al. | |
| 2013/0013070 A1 | 1/2013 | McCormack et al. | |
| 2013/0018474 A1 | 1/2013 | McCormack et al. | |
| 2013/0023889 A1 | 1/2013 | Blain et al. | |
| 2013/0023995 A1 | 1/2013 | McCormack et al. | |
| 2013/0023996 A1 | 1/2013 | McCormack et al. | |
| 2013/0030440 A1 | 1/2013 | McCormack et al. | |
| 2013/0030532 A1 | 1/2013 | McCormack et al. | |
| 2013/0110168 A1 | 5/2013 | McCormack et al. | |
| 2013/0110243 A1 | 5/2013 | Patterson et al. | |
| 2013/0123922 A1 | 5/2013 | McCormack et al. | |
| 2013/0123923 A1 | 5/2013 | Pavlov et al. | |
| 2013/0144389 A1 | 6/2013 | Bonutti | |
| 2013/0226239 A1 | 8/2013 | Altarac et al. | |
| 2013/0238095 A1 | 9/2013 | Pavento et al. | |
| 2013/0253649 A1 | 9/2013 | Davis | |
| 2013/0274763 A1 | 10/2013 | Drapeau et al. | |
| 2013/0310839 A1 | 11/2013 | McCormack et al. | |
| 2013/0310878 A1 | 11/2013 | McCormack et al. | |
| 2013/0310943 A1 | 11/2013 | McCormack et al. | |
| 2013/0317548 A1 | 11/2013 | Malone | |
| 2013/0338720 A1 | 12/2013 | Kleiner | |
| 2014/0012318 A1 | 1/2014 | Goel | |
| 2014/0025113 A1 | 1/2014 | McCormack et al. | |
| 2014/0066758 A1 | 3/2014 | Marik et al. | |
| 2014/0100657 A1 | 4/2014 | McCormack et al. | |
| 2014/0114415 A1 | 4/2014 | Tyber | |
| 2014/0135930 A1 | 5/2014 | Georges | |
| 2014/0172103 A1 | 6/2014 | O'neil et al. | |
| 2014/0228959 A1 | 8/2014 | Niemiec et al. | |
| 2014/0296916 A1 | 10/2014 | Mccormack et al. | |
| 2014/0379087 A1 | 12/2014 | McCormack | |
| 2015/0025635 A1 | 1/2015 | Laubert | |
| 2015/0088200 A1 | 3/2015 | Lins | |
| 2015/0100129 A1 | 4/2015 | Waugh et al. | |
| 2015/0201977 A1 | 7/2015 | Mccormack et al. | |
| 2015/0230834 A1* | 8/2015 | Cannestra | A61B 17/7064 606/247 |
| 2015/0297357 A1 | 10/2015 | McCormack et al. | |
| 2015/0328005 A1 | 11/2015 | Padovani et al. | |
| 2015/0328010 A1 | 11/2015 | Martynova et al. | |
| 2015/0342617 A1 | 12/2015 | Kunz et al. | |
| 2015/0342648 A1 | 12/2015 | Mccormack et al. | |
| 2015/0342649 A1* | 12/2015 | McCormack | A61B 17/7011 606/279 |
| 2016/0008040 A1 | 1/2016 | Mccormack et al. | |
| 2016/0242754 A1 | 8/2016 | Mccormack et al. | |
| 2016/0250035 A1 | 9/2016 | De Villiers et al. | |
| 2016/0317316 A1 | 11/2016 | Mccormack et al. | |
| 2016/0331553 A1 | 11/2016 | Liou et al. | |
| 2017/0027713 A1 | 2/2017 | Kleiner | |
| 2017/0135733 A1 | 5/2017 | Donner et al. | |
| 2017/0189199 A1 | 7/2017 | Maier et al. | |
| 2017/0216044 A1 | 8/2017 | McCormack et al. | |
| 2017/0281360 A1 | 10/2017 | Seifert | |
| 2017/0348027 A1 | 12/2017 | McCormack et al. | |
| 2017/0354444 A1 | 12/2017 | McCormack et al. | |
| 2017/0360571 A1 | 12/2017 | Mesiwala | |
| 2018/0161077 A1 | 6/2018 | McCormack et al. | |
| 2018/0168772 A1 | 6/2018 | Abboud et al. | |
| 2018/0303623 A1 | 10/2018 | Shoshtaev | |
| 2018/0303631 A1 | 10/2018 | Phan et al. | |
| 2019/0209151 A1 | 7/2019 | McCormack et al. | |
| 2019/0239932 A1 | 8/2019 | McCormack et al. | |
| 2019/0240041 A1 | 8/2019 | McCormack et al. | |
| 2019/0247099 A1 | 8/2019 | McCormack et al. | |
| 2019/0307571 A1 | 10/2019 | McCormack et al. | |
| 2019/0307572 A1 | 10/2019 | McCormack et al. | |
| 2019/0350626 A1 | 11/2019 | McCormack et al. | |
| 2020/0085475 A1 | 3/2020 | McCormack et al. | |
| 2020/0289285 A1 | 9/2020 | Siemionow et al. | |
| 2020/0375633 A1 | 12/2020 | McCormack et al. | |
| 2021/0022881 A1 | 1/2021 | McCormack et al. | |
| 2021/0059833 A1 | 3/2021 | Tanaka et al. | |
| 2022/0211513 A1 | 7/2022 | Mccormack et al. | |
| 2022/0287742 A1 | 9/2022 | Mccormack et al. | |
| 2022/0313448 A1 | 10/2022 | Mccormack | |
| 2022/0323117 A1 | 10/2022 | Phan et al. | |
| 2023/0139017 A1 | 5/2023 | McCormack et al. | |
| 2023/0149179 A1 | 5/2023 | McCormack et al. | |
| 2023/0181327 A1 | 6/2023 | Tanaka et al. | |

FOREIGN PATENT DOCUMENTS

| | | |
|---|---|---|
| JP | H11508781 A | 8/1999 |
| JP | 2004523288 A | 8/2004 |
| JP | 2008509735 A | 4/2008 |
| JP | 2008522787 A | 7/2008 |
| JP | 2012501234 A | 1/2012 |
| JP | 2014516268 A | 7/2014 |
| WO | 9641582 A1 | 12/1996 |
| WO | 99/49818 A1 | 10/1999 |
| WO | 00/035388 A1 | 6/2000 |
| WO | 00/53126 A1 | 9/2000 |
| WO | 01/01895 A1 | 1/2001 |
| WO | 02/34120 A2 | 5/2002 |
| WO | 02/038062 A2 | 5/2002 |
| WO | 02/076335 A2 | 10/2002 |
| WO | 2005032358 A2 | 4/2005 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008127978 A2 | 10/2008 |
| WO | 2008153732 A1 | 12/2008 |
| WO | 2009089367 A2 | 7/2009 |
| WO | 2009148619 A2 | 12/2009 |
| WO | 2010030994 A2 | 3/2010 |
| WO | 2010074714 A2 | 7/2010 |
| WO | 2010107692 A1 | 9/2010 |
| WO | 2011050140 A1 | 4/2011 |
| WO | 2013043584 A2 | 3/2013 |
| WO | 2014188280 A2 | 11/2014 |
| WO | 2016049784 A1 | 4/2016 |

OTHER PUBLICATIONS

Atul Goel, Facetai distraction as treatment for single- and multilevel cervical spondylotic radiculopathy and myelopathy: a preliminary report, J Neurosurg Spine, Jun. 2011, pp. 689-696.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

Stein, et al., "Percutaneous Facet Joint Fusion: Preliminary Experience," Journal of Vascular and Interventional Radiology, Jan.-Feb. 1993, pp. 69-74, vol. 4, No. 1.

(56) References Cited

OTHER PUBLICATIONS

International Search Report and Written Opinion of the International Searching Authority for International Patent Application No. PCT/US2018/033505, dated Sep. 25, 2018 (12 pages).

* cited by examiner

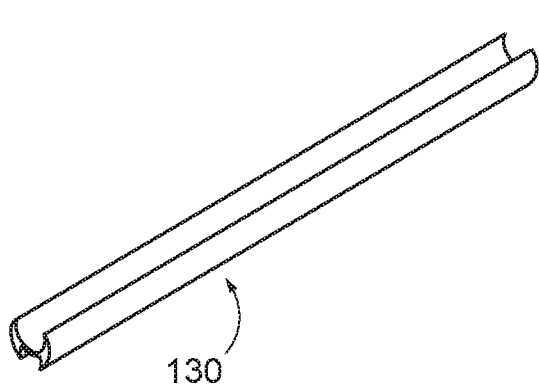 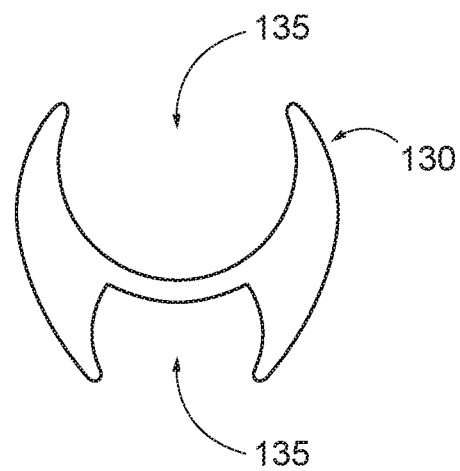
FIG. 14A  FIG. 14B
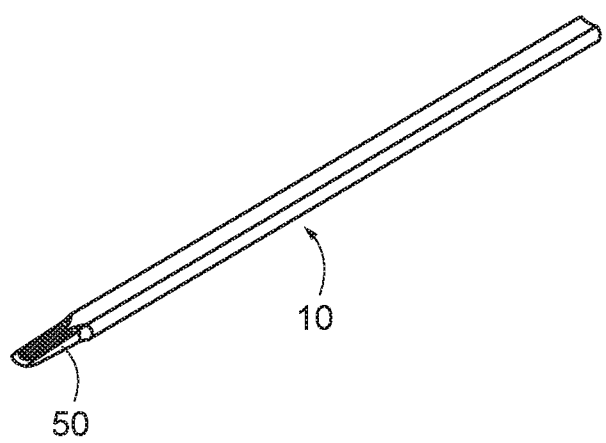 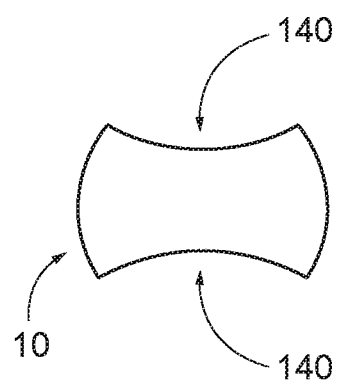
FIG. 14C  FIG. 14D

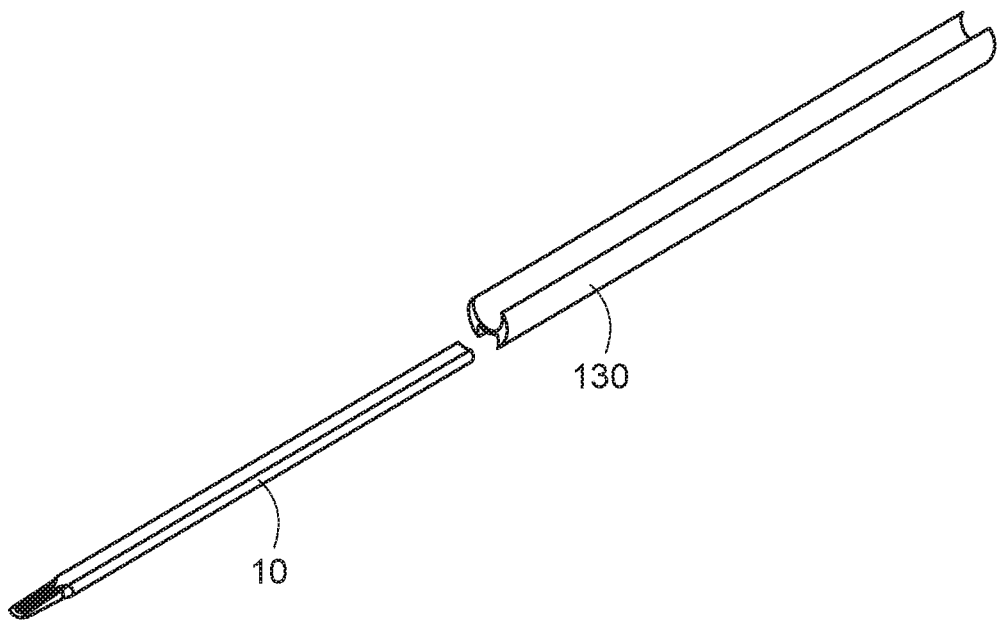
FIG. 14E
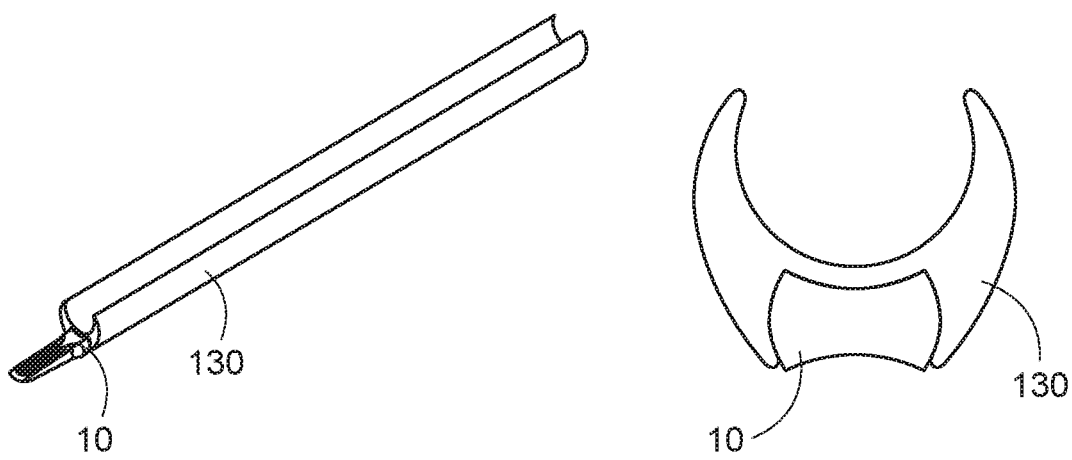
FIG. 14F
FIG. 14G

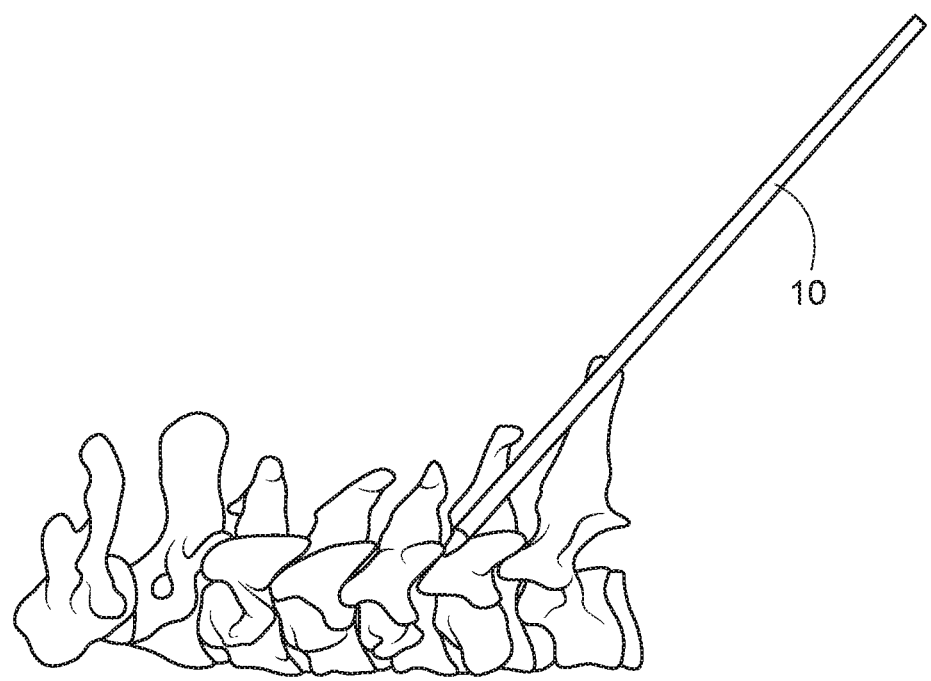
FIG. 14H
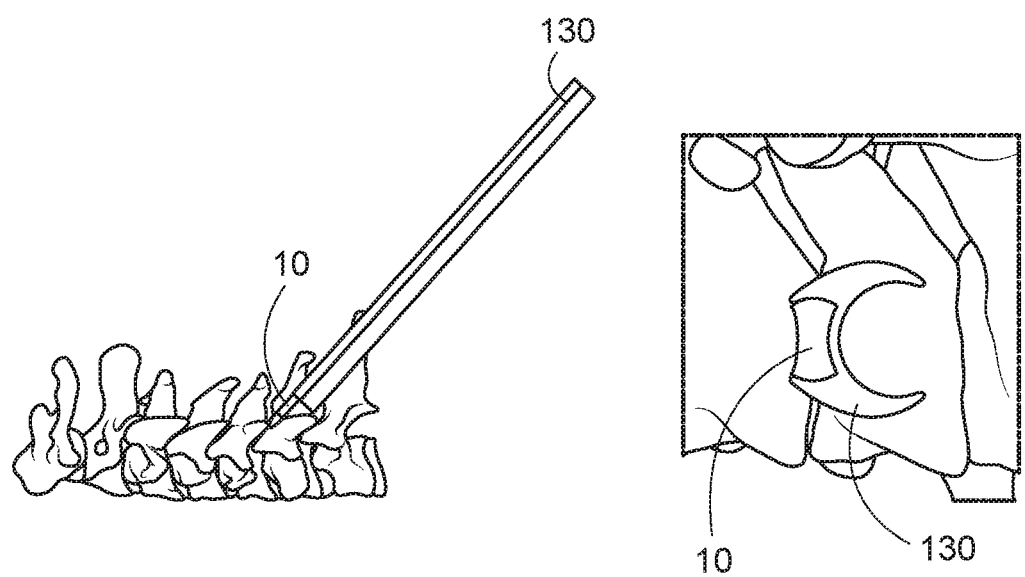
FIG. 14I
FIG. 14J

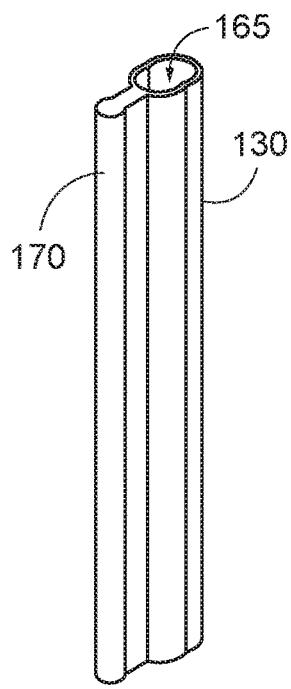
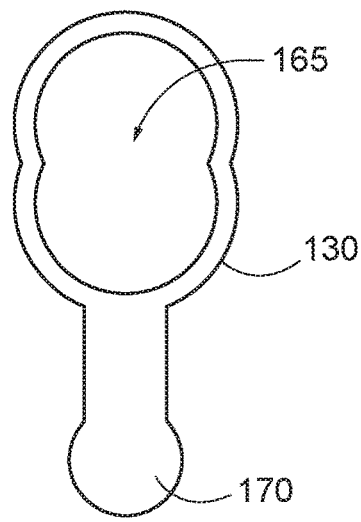
FIG. 17A  　　　　　　　FIG. 17B
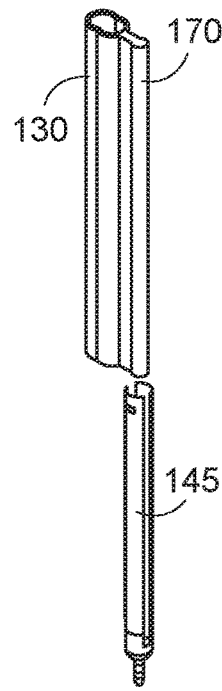
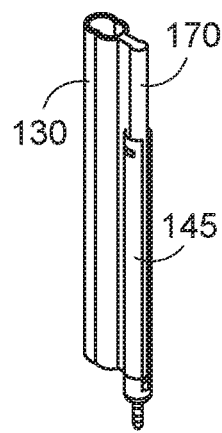
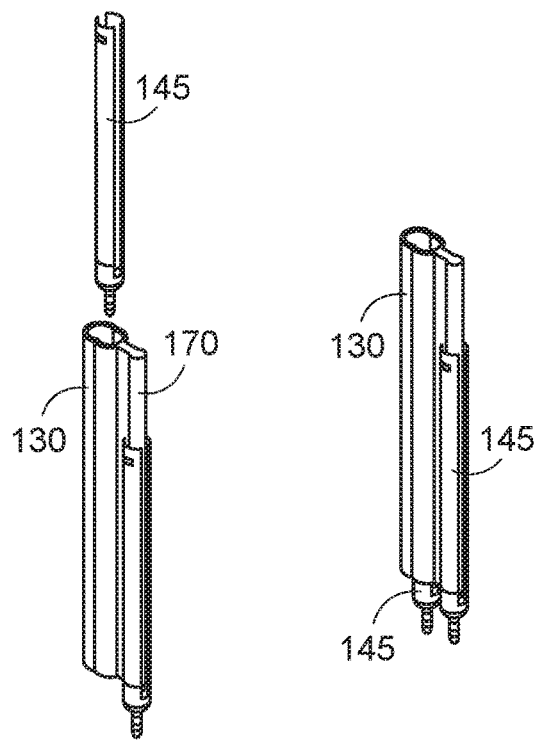
FIG. 17C　　FIG. 17D　　FIG. 17E　　FIG. 17F

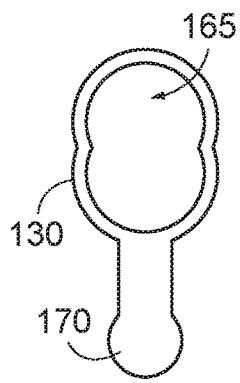 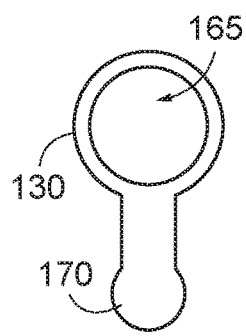 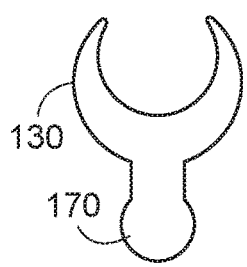 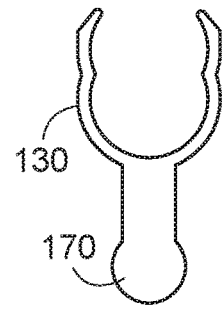
FIG. 18A  FIG. 18B  FIG. 18C  FIG. 18D
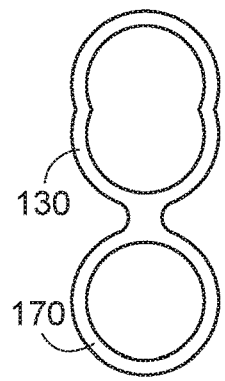 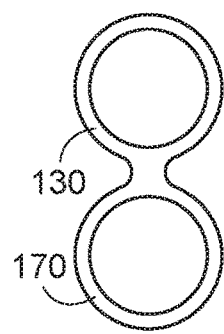 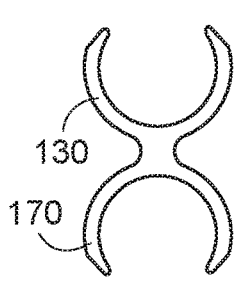 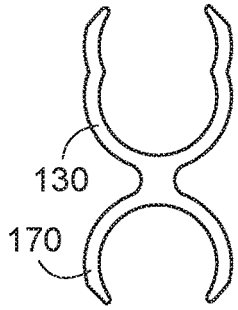
FIG. 18E  FIG. 18F  FIG. 18G  FIG. 18H
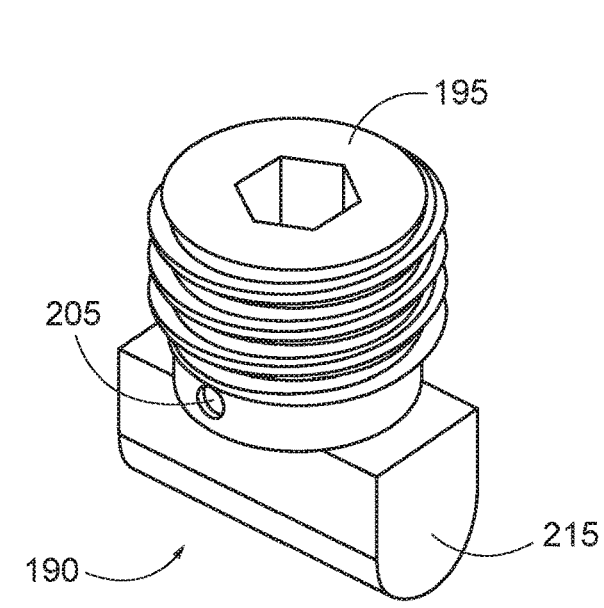 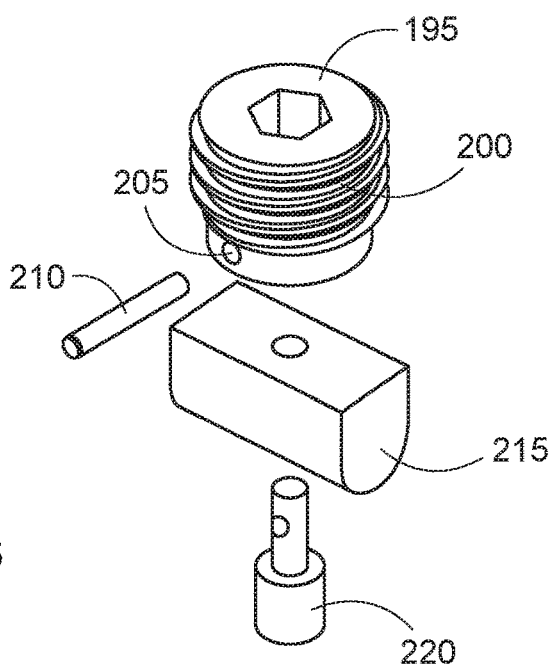
FIG. 19A  FIG. 19B

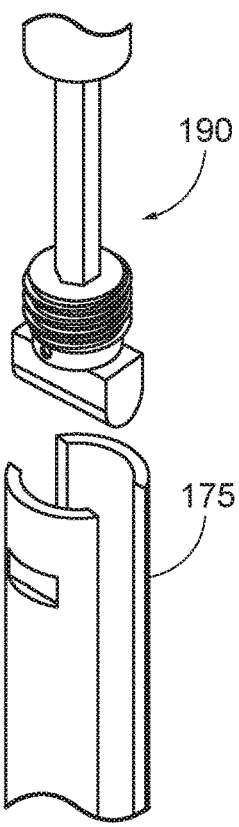 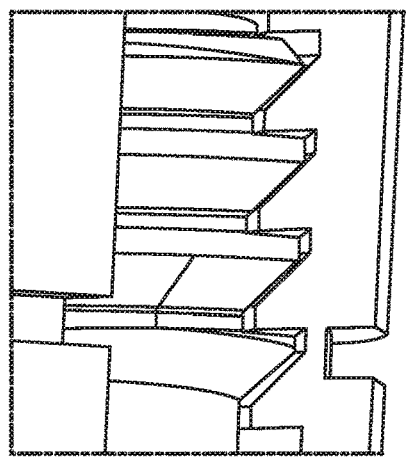 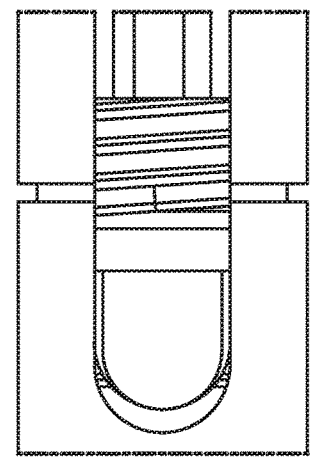
FIG. 19C  FIG. 19D  FIG. 19E
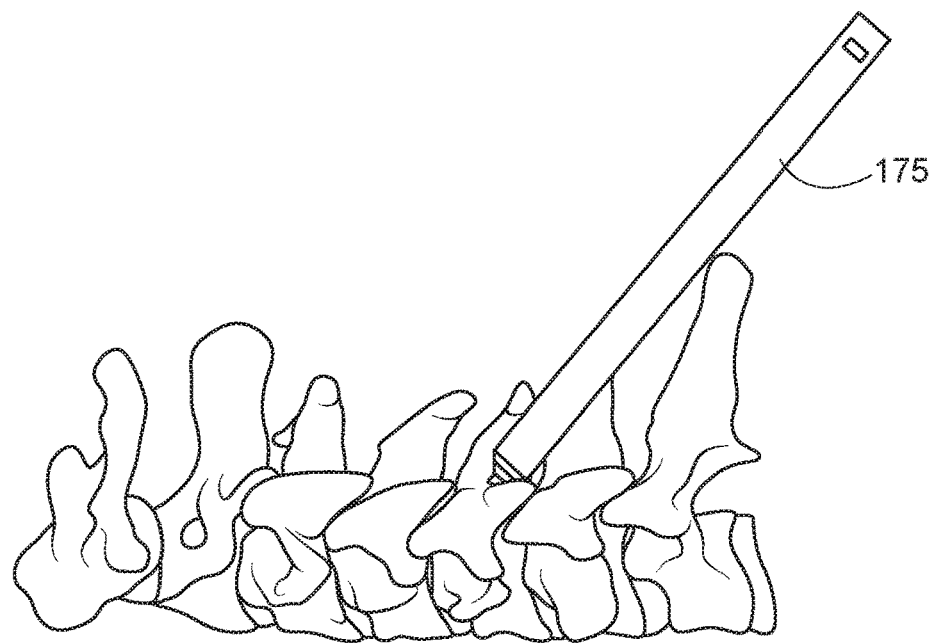
FIG. 19F

SPINAL FIXATION ACCESS AND DELIVERY SYSTEM

CROSS-REFERENCE TO RELATED APPLICATION

This application is the national stage application of International Application No. PCT/US2015/033505, filed May 18, 2018, and entitled "SPINAL FIXATION ACCESS AND DELIVERY SYSTEM," which claims priority to U.S. Patent Application No. 62/508,434, filed May 19, 2017 and entitled SPINAL FIXATION ACCESS AND DELIVERY SYSTEM, which are hereby incorporated by reference in its entirety and for all purposes.

FIELD

This application is directed to medical devices and methods. More specifically, the application is directed to devices and methods related to spinal fixation to provide stability to the spine and promote spinal fusion.

BACKGROUND

Chronic back problems are one of the most common causes of pain and disability in the United States and other developed countries. According to at least one estimate, spinal fusion procedures, in which two adjacent vertebrae are fused together using plates, screws and other implants, are the most commonly performed surgical procedures in the United States. Spinal fusion is often performed in an attempt to increase space between the two adjacent vertebrae being operated on (known as spinal distraction) and to thus prevent impingement of the spinal cord or nerve roots branching from the spinal cord and passing through openings in the vertebral column. Unfortunately, most techniques and devices used for performing spinal fusion are relatively invasive and involve a number of risks and difficult recovery and rehabilitation.

Posterior spinal fusion is one method of surgical intervention. However, in order to provide direct visualization of the target area, it requires extensive dissection of muscles and ligaments. This dissection causes acute and chronic soft tissue pain syndrome. Acutely, patients are typically hospitalized for three to four days for pain control that requires IV narcotics. Long-term, patients frequently have persistent pain due to the extensive nature of the dissection. This is compared to one-day hospitalization for anterior approaches that do not require any muscle or soft tissue dissection. In some cases, soft tissues may not return to anatomic position and may be permanently deformed. Persistent pain after posterior surgical approaches is referred to as post-laminectomy syndrome.

Therefore, since it is considered less traumatic to the patient, anterior spinal fusion surgery has generally been preferred over posterior fusion surgery. However, posterior approaches to the cervical spine do have some advantages over anterior approaches.

Lateral mass or pedicle screw fixation provides more rigid fixation of the cervical spine than anterior plates, interbody devices and interspinous wiring. It is often used for traumatic instability, but it has also been used for degenerative conditions. Despite providing good results, lateral mass fixation is often avoided because of the morbidity of the soft tissue dissection, as noted above.

Therefore, a need exists for alternative devices and methods for fixation of the spine following surgery for fusion of adjacent vertebrae. Ideally, these devices, systems and methods would allow for minimally invasive or less invasive access and fixation that many of the currently available techniques do not provide. For example, it may be advantageous to have devices, systems and methods that use a posterior approach for accessing the spine. At least some of these objectives will be met by the embodiments described herein.

BRIEF SUMMARY

The various embodiments described herein provide devices, systems and methods for accessing the cervical spine via a posterior approach and delivering or providing a spinal fixation device for fixation of the cervical spine. The embodiments described below generally include an access and delivery system through which or along which one or more spinal fixation devices may be advanced. The access devices described herein generally include a distal end that can be inserted into a cervical facet. Once inserted into the facet, the access device can be used as a point of stabilization.

A cervical facet joint access device for accessing the cervical facet joint via a posterior access approach is disclosed. In some aspects, the device includes a body having a proximal portion and a distal portion and a chamfered or beveled end feature positioned at the distal portion of the body and configured for insertion at the cervical facet joint. In some aspects, the chamfered or beveled end feature is offset from the body. In some aspects, the body is an elongated body having opposing top and bottom faces, opposing side faces and opposing end faces and the chamfered or beveled end feature is offset from the body and positioned on one of the opposing side faces. In some aspects, the body has a rectangular shaped cross section. In some aspects, the proximal portion has a first height and the distal portion has a second height and the first height is greater than the second height. In some aspects, the body is an elongated tubular body. In some aspects, the chamfered or beveled end feature is positioned at an end of the distal portion. In some aspects, the end further includes a stop adapted to abut a posterior edge of the facet joint. The stop may include a raised or protruding feature adapted to engage the facet joint. In some aspects, the end feature includes an expandable anchor held in a closed position via a detent feature and opened by actuation of an internal rod to pivot the arms of the end feature into an open position. In some aspects, the end feature includes an expandable member held in a closed position for delivery and expanded into an open position by actuation of an internal rod. In some aspects, the end feature comprises an articulating tip. In some aspects, the body is a tubular body adapted to receive other surgical instruments for spinal fixation.

A spinal fixation access and delivery system for accessing the cervical facet joint via a posterior access approach is disclosed. In some aspects, the system includes an access device including a body having a proximal portion and a distal portion and a chamfered or beveled end feature positioned at the distal portion of the body and configured for insertion at the cervical facet joint. The system may further include a guide device having access device engagement features and a spinal fixation member. The access device includes at least one guide device receiving feature complementary to or keyed to the engagement feature of the guide device.

The access device may be the access device as disclosed herein. In some aspects, the chamfered or beveled end feature of the access device is offset from the body. In some aspects, the body is an elongated body having opposing top and bottom faces, opposing side faces and opposing end faces and the chamfered or beveled end feature is offset from the body and positioned on one of the opposing side faces. In some aspects, the body has a rectangular shaped cross section. In some aspects, the proximal portion has a first height and the distal portion has a second height and the first height is greater than the second height. In some aspects, the body is an elongated tubular body. In some aspects, the chamfered or beveled end feature is positioned at an end of the distal portion. In some aspects, the end further includes a stop adapted to abut a posterior edge of the facet joint. The stop may include a raised or protruding feature adapted to engage the facet joint. In some aspects, the end feature includes an expandable anchor held in a closed position via a detent feature and opened by actuation of an internal rod to pivot the arms of the end feature into an open position. In some aspects, the end feature includes an expandable member held in a closed position for delivery and expanded into an open position by actuation of an internal rod. In some aspects, the end feature comprises an articulating tip. In some aspects, the body is a tubular body adapted to receive other surgical instruments for spinal fixation.

In some aspects, the device engagement features are selected from a protrusion, a notch or a recess. In some aspects, the system may further include a decortication tool. A portion of the decortication tool may optionally include a burr, a rasp or one or more teeth.

A spinal fixation access and delivery system for accessing the cervical facet joint via a posterior access approach is disclosed. In some aspects, the system includes an access device, a spinal fixation member, and a guide device having at least one spinal fixation member engagement feature. The spinal fixation member includes at least one guide device receiving feature complementary to or keyed to the engagement feature of the guide device. In some aspects, the spinal fixation member is a tower or a polyaxial screw with a tower feature. In some aspects, the at least one spinal fixation member engagement feature is a generally cylindrical body protruding from an outer surface of the guide device and generally extending the length of the guide device. The access device may be the access device as disclosed herein.

In some aspects, the chamfered or beveled end feature of the access device is offset from the body. In some aspects, the body is an elongated body having opposing top and bottom faces, opposing side faces and opposing end faces and the chamfered or beveled end feature is offset from the body and positioned on one of the opposing side faces. In some aspects, the body has a rectangular shaped cross section. In some aspects, the proximal portion has a first height and the distal portion has a second height and the first height is greater than the second height. In some aspects, the body is an elongated tubular body. In some aspects, the chamfered or beveled end feature is positioned at an end of the distal portion. In some aspects, the end further includes a stop adapted to abut a posterior edge of the facet joint. The stop may include a raised or protruding feature adapted to engage the facet joint. In some aspects, the end feature includes an expandable anchor held in a closed position via a detent feature and opened by actuation of an internal rod to pivot the arms of the end feature into an open position. In some aspects, the end feature includes an expandable member held in a closed position for delivery and expanded into an open position by actuation of an internal rod. In some aspects, the end feature comprises an articulating tip. In some aspects, the body is a tubular body adapted to receive other surgical instruments for spinal fixation.

A cervical spinal fixation member is disclosed. In some aspects, the spinal fixation member includes an elongated tubular body having a length extending between a distal and a proximal end, a rod receiving slot defined in at least a portion of the length of the tubular body; and a polyaxial screw. The spinal fixation member may further include a rod. In some aspects, the rod receiving slot further includes an opening defined in the outer circumference of the elongated tubular body. In some aspects, the rod receiving slot extends only a portion of the length of the elongated body and the elongated body is solid for the remainder of the length.

These and other aspects and embodiments will be described in further detail below, in reference to the attached drawing figures.

BRIEF DESCRIPTION OF DRAWINGS

FIGS. 5A and 5C show a closed position and FIGS. 5B and 5D show an open position.

FIGS. 6A and 6C show a closed position and FIGS. 6B and 6D show an open position.

FIGS. 14A-14G illustrate an access and delivery system according to aspects of the present disclosure.

FIGS. 14H-14S illustrate the system of FIGS. 14A-14G in use.

FIGS. 17A-17F illustrate a portion of an access and delivery system according to aspects of the present disclosure which may be further stabilized by engagement with a fixation device.

FIGS. 18A-H are cross-sections of various embodiments of a portion of an access and delivery system according to aspects of the present disclosure which may be further stabilized by engagement with a fixation device.

FIGS. 19A-19E are various views of a temporary locking screw that may be used with the system of FIG. 17.

FIGS. 19F-19Q show the screw and system of FIGS. 17 and 19A-19E in use.

DETAILED DESCRIPTION

Spinal stenosis reflects a narrowing of one or more areas of the spine, often in the upper or lower back. This narrowing can put pressure on the spinal cord or on the nerves that branch out from the compressed areas. Individual vertebrae of the spine are positioned relative to each other, and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

Figure 1:
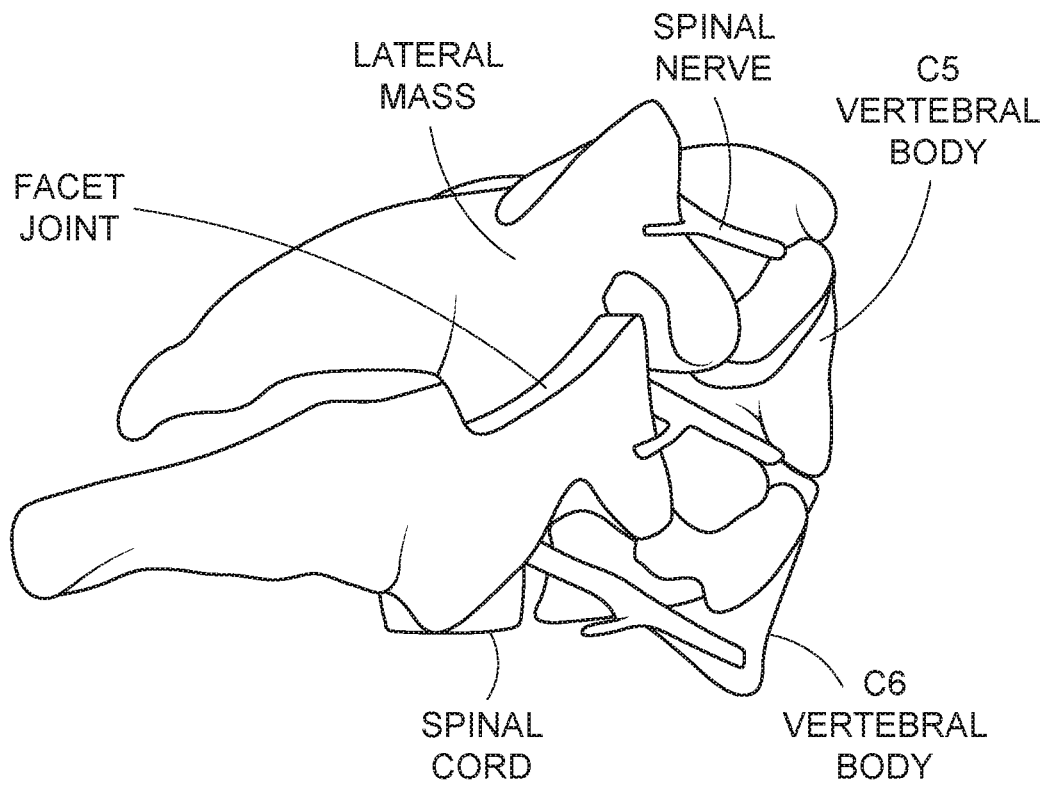
FIG. 1 is a lateral view of the C5 and C6 (cervical) vertebrae.

Options for distracting two adjacent vertebrae of a spine, such as the cervical vertebrae shown in FIG. 1, in an effort to ameliorate spinal stenosis, are varied and may include the use of implants, or cages and screws. In many cases, it may be possible to insert a facet joint implant into a facet joint by itself and, due to the design of the implant, do nothing further to secure the implant within the joint. In other words, the shape, size, surface features and overall configuration of the implant may cause it to remain securely within the facet joint without further attachment devices required. In some cases however, and in general for overall safety of a facet joint distraction procedure, it may be advantageous to use one or more additional devices, such as screws, to help secure the facet joint implant to one or both of the adjacent vertebrae that form the joint with a screw.

Still further, it may be advantageous to provide additional stabilization to the fusion site with the use of a pedicle screw and/or a lateral mass screw as a supplement to spinal fusion surgery. A pedicle screw or lateral mass screw are types of bone screws designed for insertion into the pedicle or lateral mass of a vertebra, respectively. The screws are inserted in adjacent vertebrae (e.g., consecutive spine segments such as C5 and C6) and then connected via a rod to prevent motion at those segments that are being fused. In this way, the screws act as anchor points for the rod and provide additional stability to fusion site to promote better fusion. Post-fusion, the rods and screws can be removed.

Described herein are devices, systems and methods for accessing the cervical spine via a posterior approach and introducing, implanting and/or securing a spinal fixation device, such as screws and rods, in the spine. Accessing the cervical spine via a posterior approach utilizes minimally invasive or less invasive techniques. Aspects described below generally include an access tool and a guide tool, through which or along which one or more spinal fixation devices may be advanced. In addition, a separate decortication tool may be advanced through or with the help of the guide tool. The decortication tool may include a burr or a rasp or teeth or other bone roughening feature for preparing the bone surface prior to insertion of the spinal fixation device.

In use, the surgeon advances the access tool into the facet joint through a minimally invasive or less invasive incision. Once anchored into place, this access tool provides a fixed point deep in the spine that is then used as a marker to advance drills, awls, plates, rods and screws, and other instruments to the cervical spine from a posterior approach without direct visualization. Such an approach with the disclosed devices prevents instruments from slipping off the spine or drills catching soft tissue and skidding out of control. In addition, the cervical facet has a fixed anatomical relationship to lateral mass bone consistent in most, if not all, patients. Instruments can be advanced over, along or about the access tool to reliable landmarks on or at the lateral mass without direct visualization. For example, to aid in spinal fixation, lateral mass screws or pedicle screws may be inserted with the help of a guide tool.

Turning now to the figures, the access tool or access device may also be referred to as an access chisel or an access anchor. The access device is advanced to the facet joint defined between adjacent vertebra, such as the vertebra of the cervical spine. The device provides access to the facet joint and surrounding anatomical structures, such as the lateral mass and the pedicle.

Referring now to FIGS. 2A-12H, the access device 10 includes a body 15 having a proximal portion 20 and a distal portion 25. The distal portion 25 further includes a chamfered or beveled end feature 30. The access device may be made of titanium, stainless steel, polycarbonate, or any other metal, metal alloy or polymer of sufficient strength.

In some aspects, as depicted in FIGS. 2A-2E, the body 15 of the access device 10 is an elongated body having opposing top and bottom faces 15a, 15b, opposing side faces 15c, 15d and opposing end faces 15e, 15f. The body has a generally rectangular cross-section at the proximal portion 20 which extends towards the distal portion 25. At the distal portion, the elongated body steps down or narrows relative to the proximal portion. That is, and with reference to FIG. 2B, a height Hp of the proximal portion is greater than a height HD of the distal portion of the body 15. The proximal portion is configured to receive a removable handle (not shown) for ease of the user in manipulation of the device 10. The distal portion 25 further includes a chamfered or beveled end feature 30 positioned on a side face 15d of the elongated body. That is, the end feature 30 is offset relative to the body.

Figure 2A:
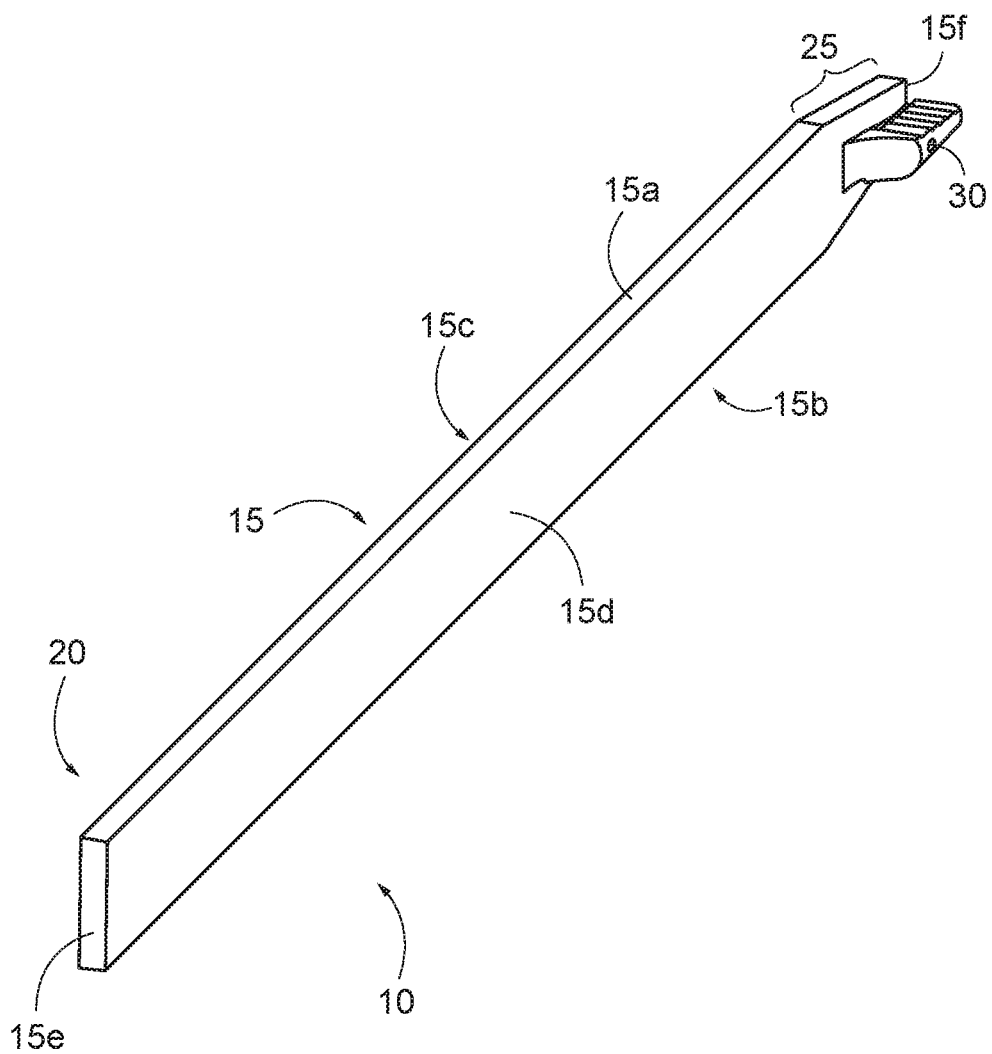
FIG. 2A is a perspective view of an access device according to the present disclosure.
Figure 2B:
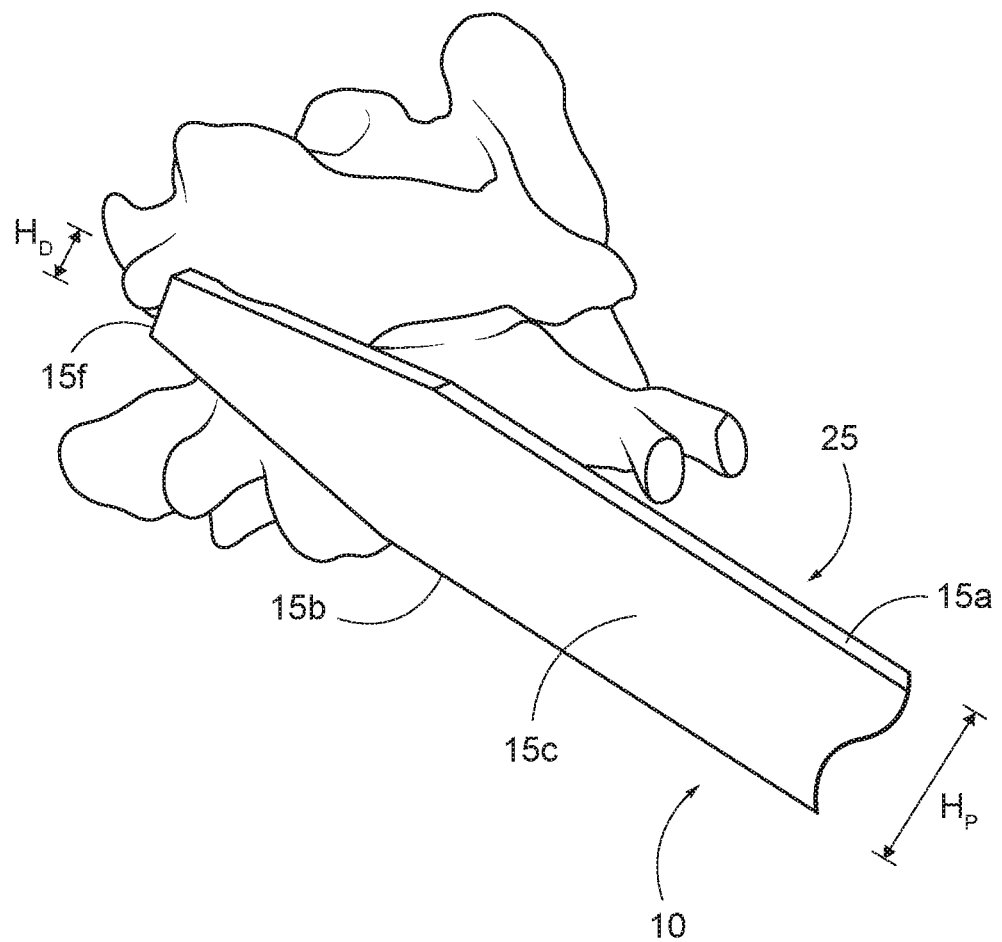
FIGS. 2B-2E are various views of the access device of FIG. 2A in use.
Figure 2C:
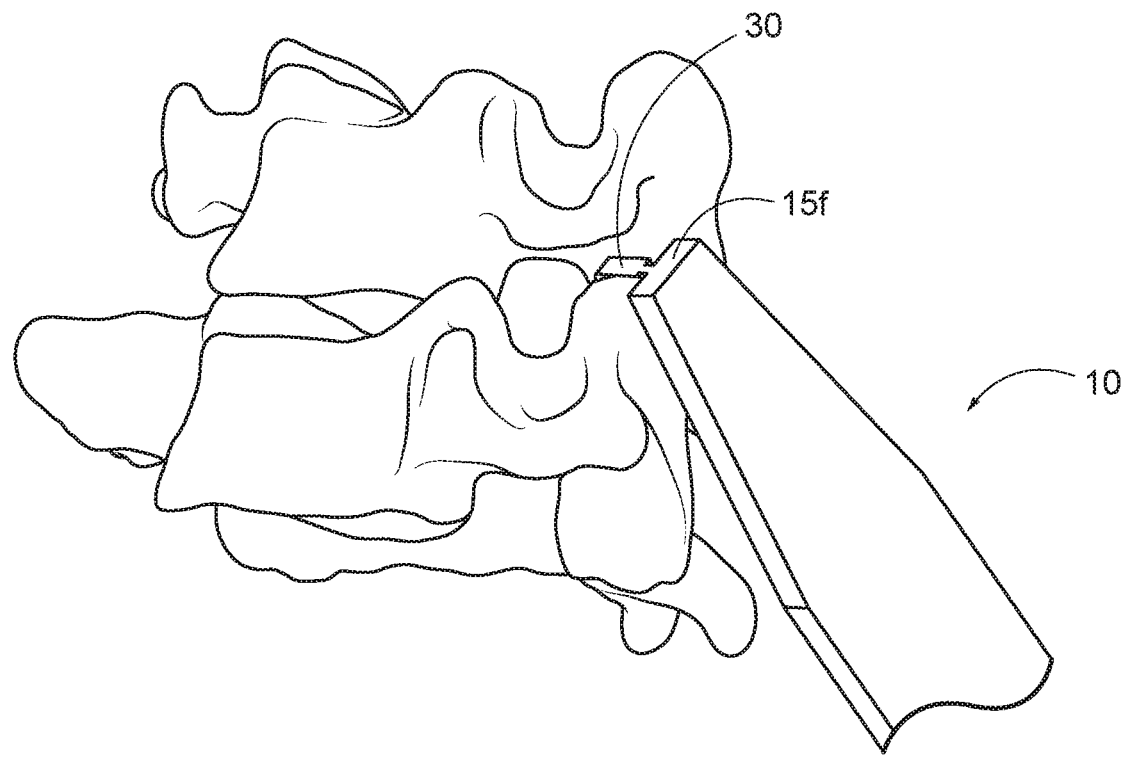
Figure 2D:
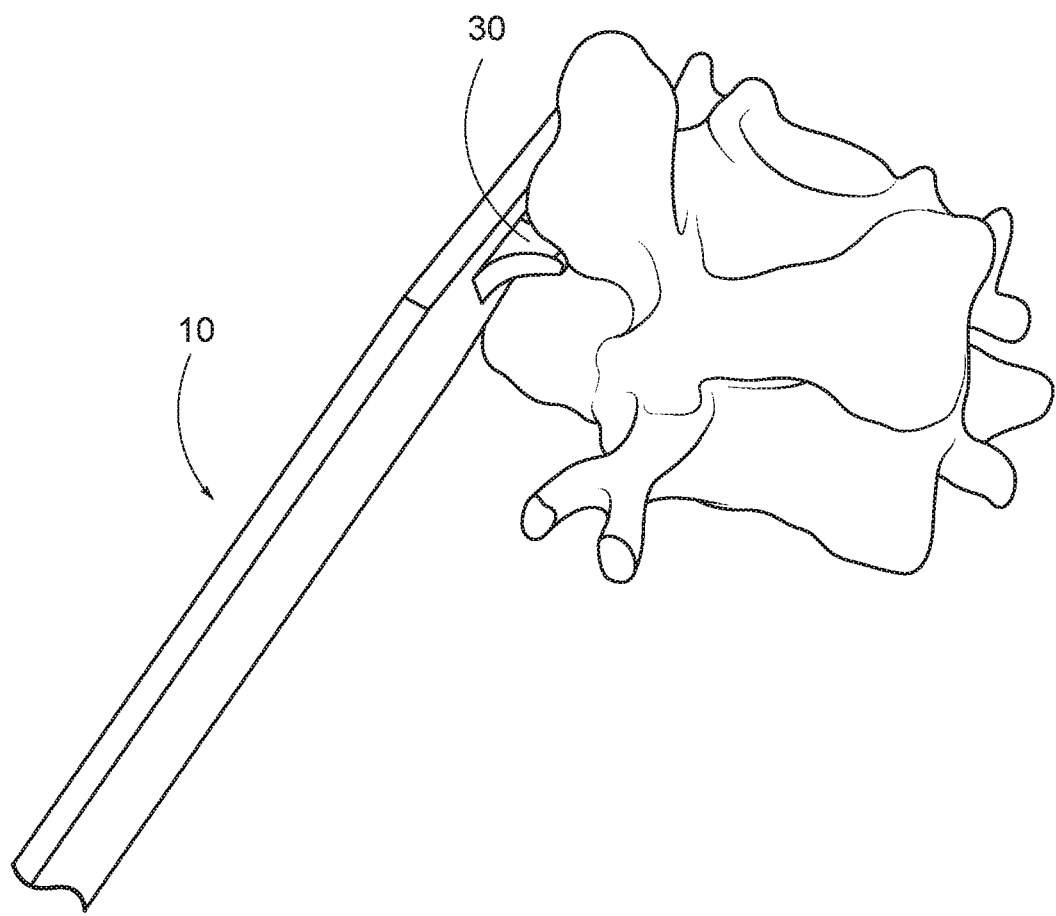
Figure 2E:
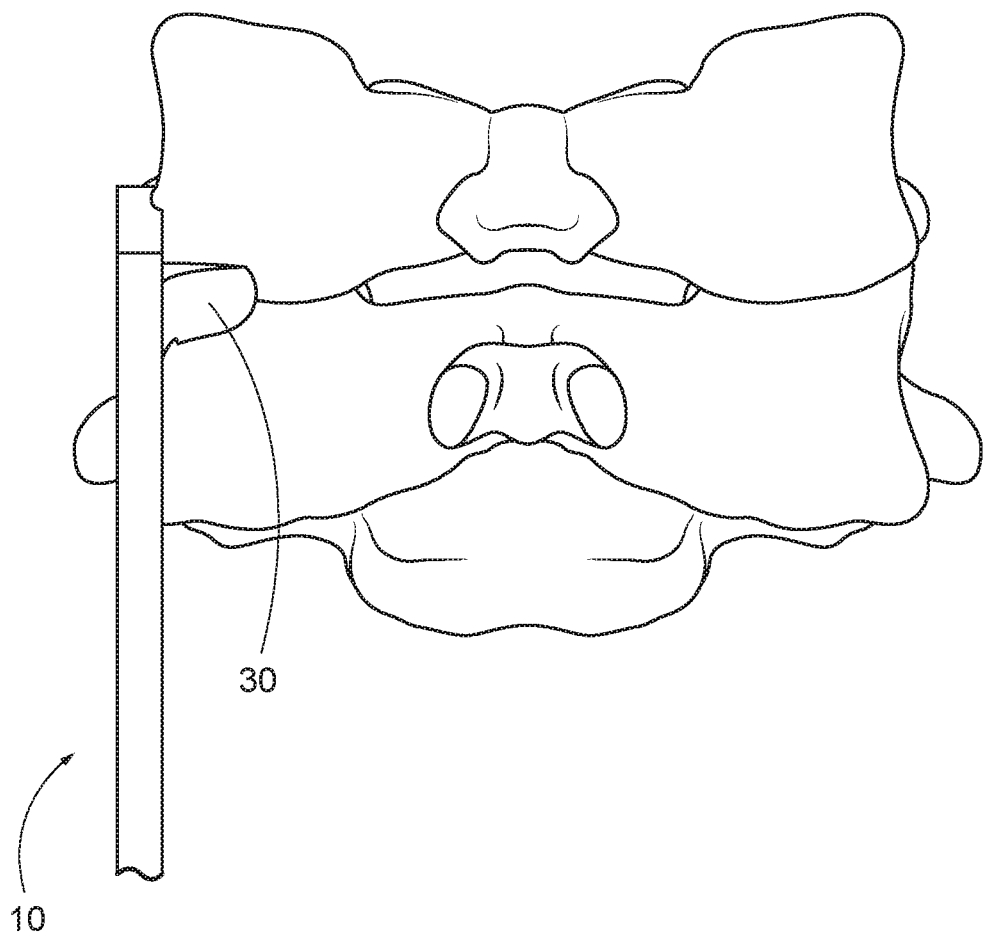

As can be understood from FIGS. 2B-2D, which illustrate the device 10 inserted at or about the facet joint, the elongated body may be vertically oriented to give vertical rigidity in the cranial-caudal direction to help resist slipping of the pedicle or lateral mass screw (insertion described in more detail below). Further, the elongated body is used to reference off the lateral aspect of the lateral mass (see FIGS. 2D-2E) and such a shape may advantageously provide for an unobstructed approach to the lateral mass.

Figure 3A:
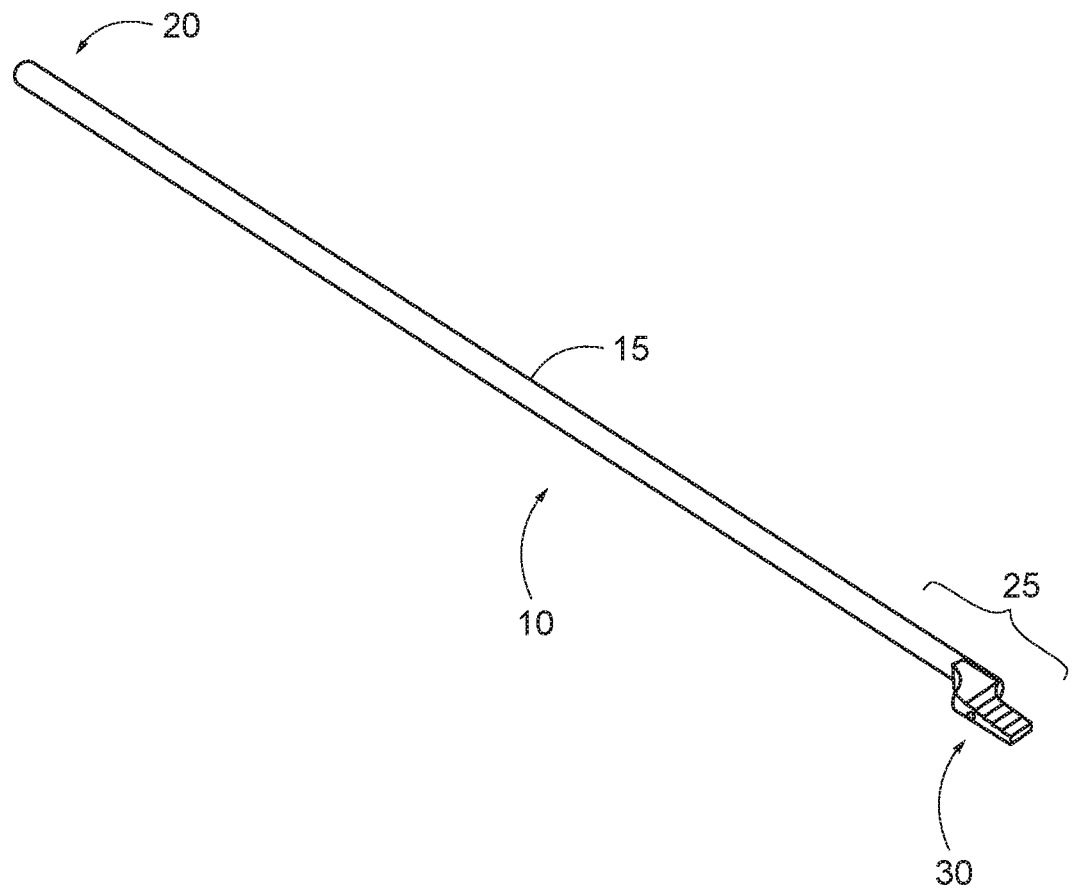
FIGS. 3A-3C are perspective, top and partial rear views of another access device according to the present disclosure.
Figure 3B:
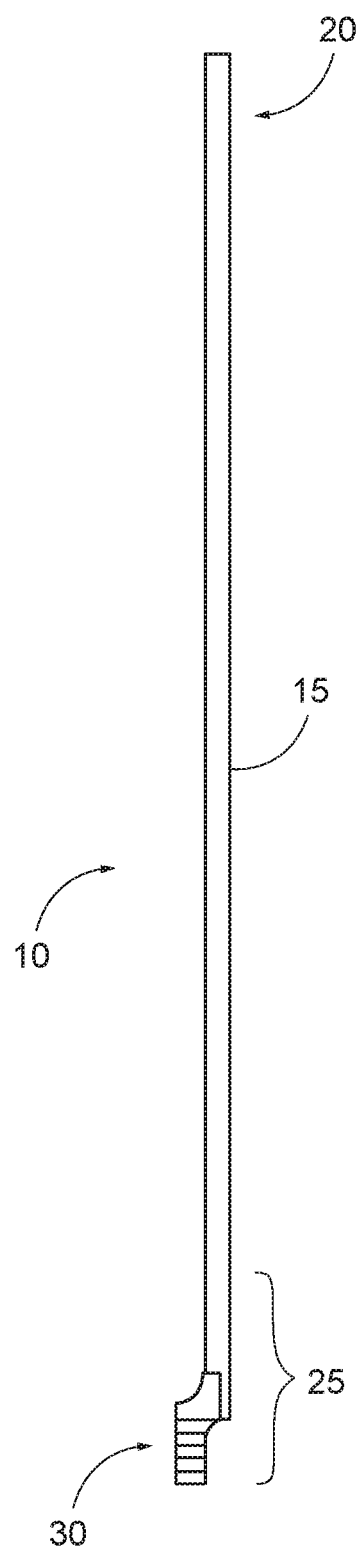
Figure 3C:
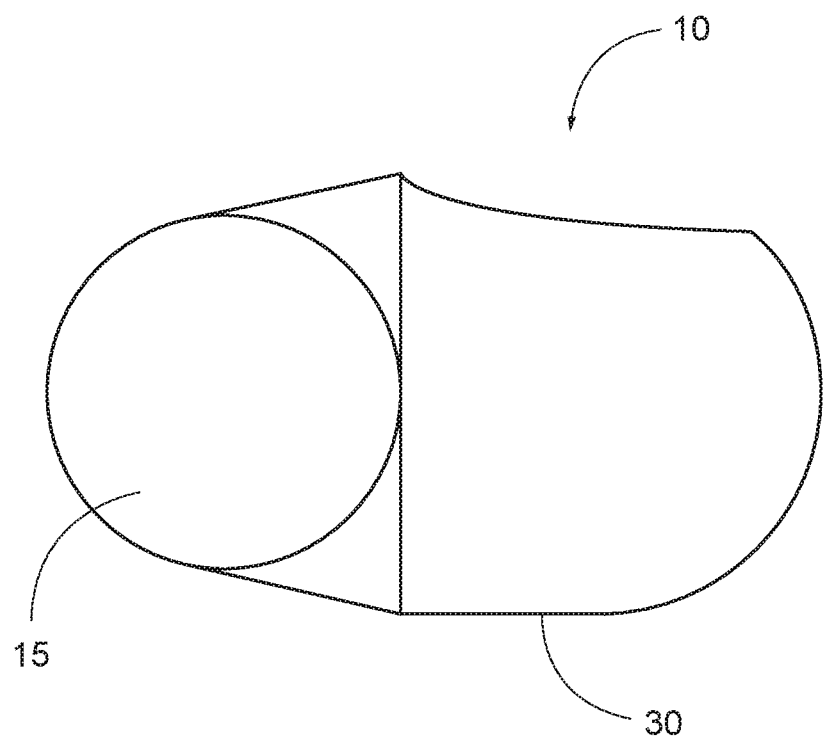

As depicted in FIGS. 3A-3C, in some aspects, the access device 10 includes the body 15 which may be an elongated tubular body having a proximal portion 20 and a distal portion 25. The distal portion 25 further includes a chamfered or beveled end feature 30 positioned on a side of the elongated body. That is, the end feature 30 is offset relative to the body. The tubular body has a low profile and may be used to slidingly receive other instruments along its body.

Figure 3D:
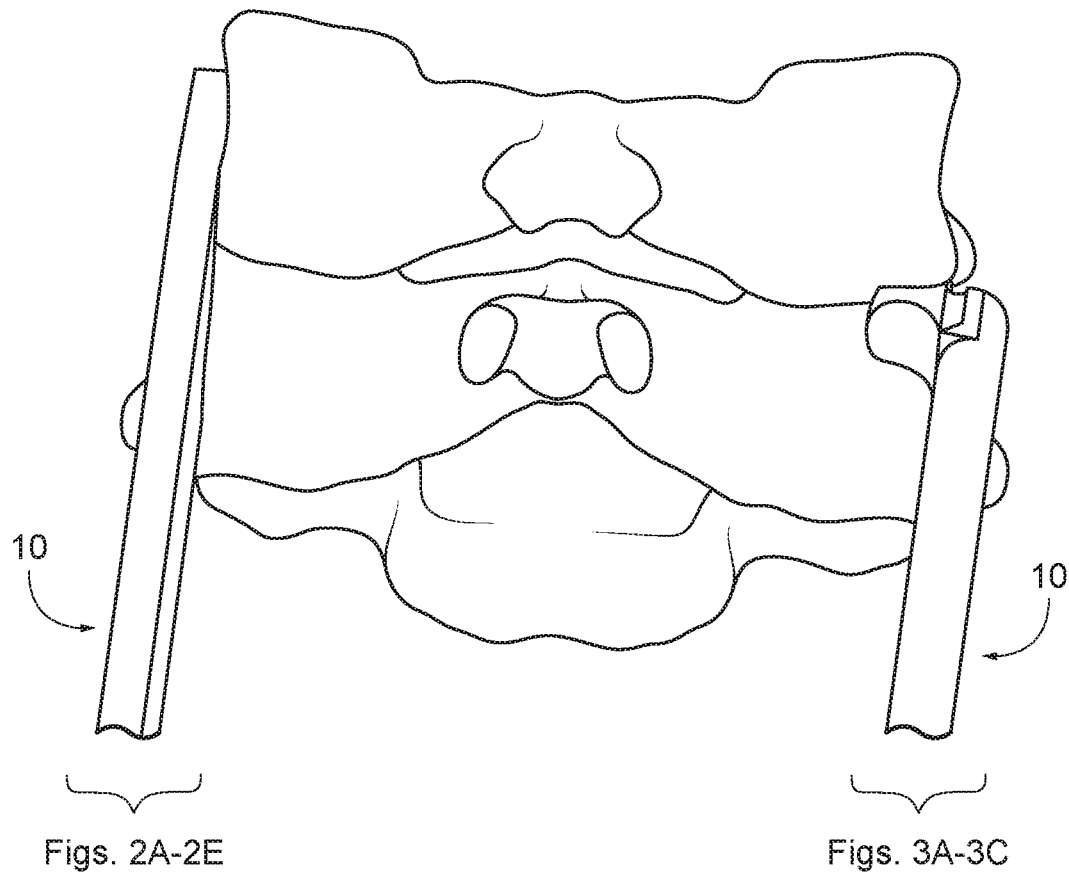
FIG. 3D is a posterior view of the access devices of both FIG. 2A and FIG. 3A in use.

FIG. 3D depicts both the access device of FIGS. 2A-2E and the access device of FIGS. 3A-3C, and illustrates an asymmetrical chamfered or beveled end feature which provides a device that is offset from the axial approach to the joint space.

Figure 4A:
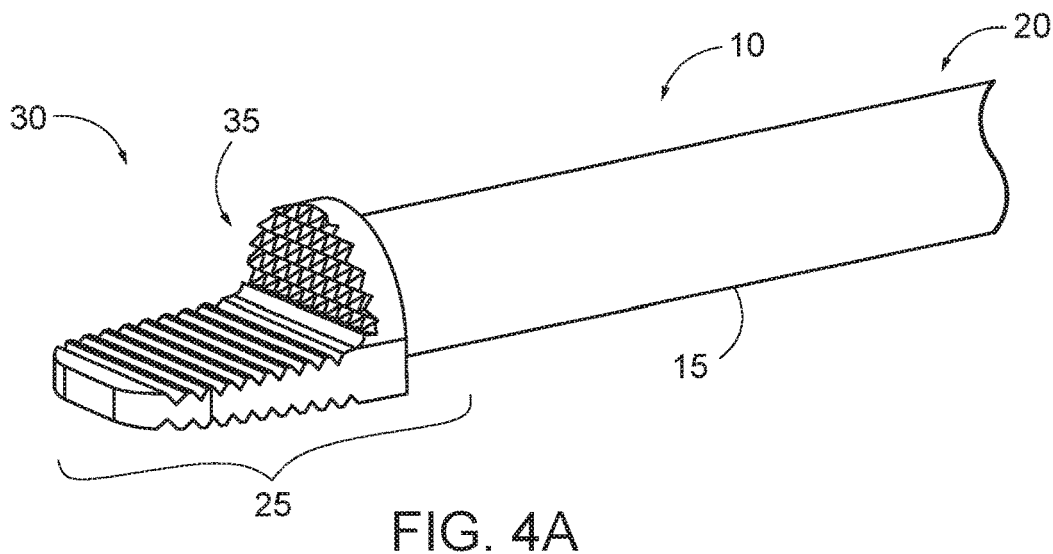
FIGS. 4A-4C are partial perspective views of an access device according to the present disclosure having a stop feature.
Figure 4B:
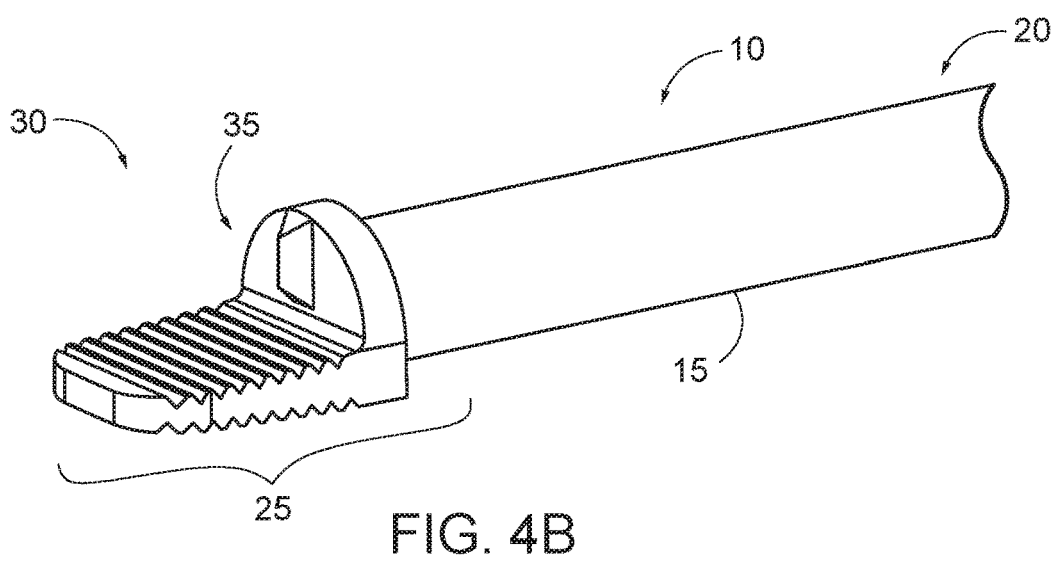
Figure 4C:
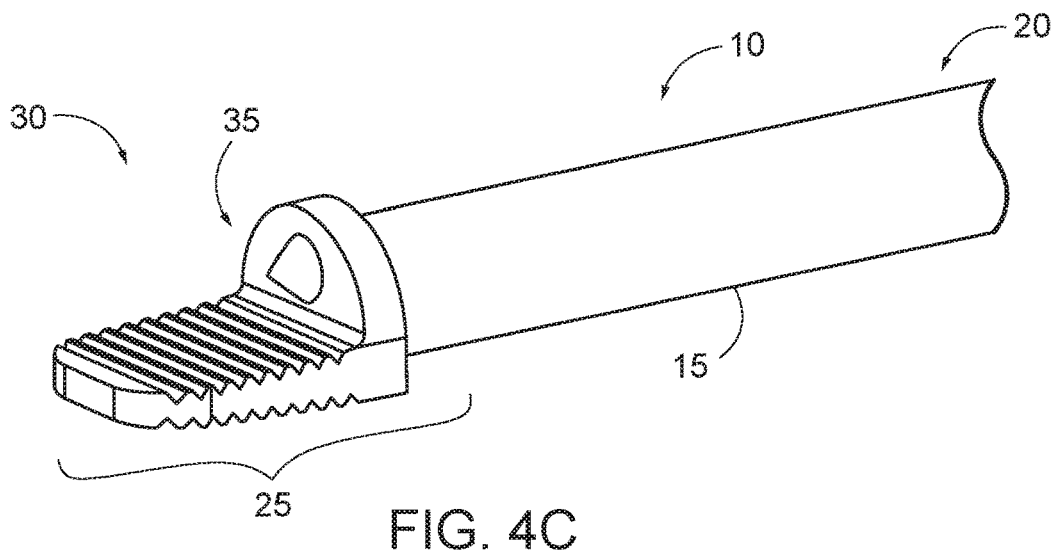
Figure 4D:
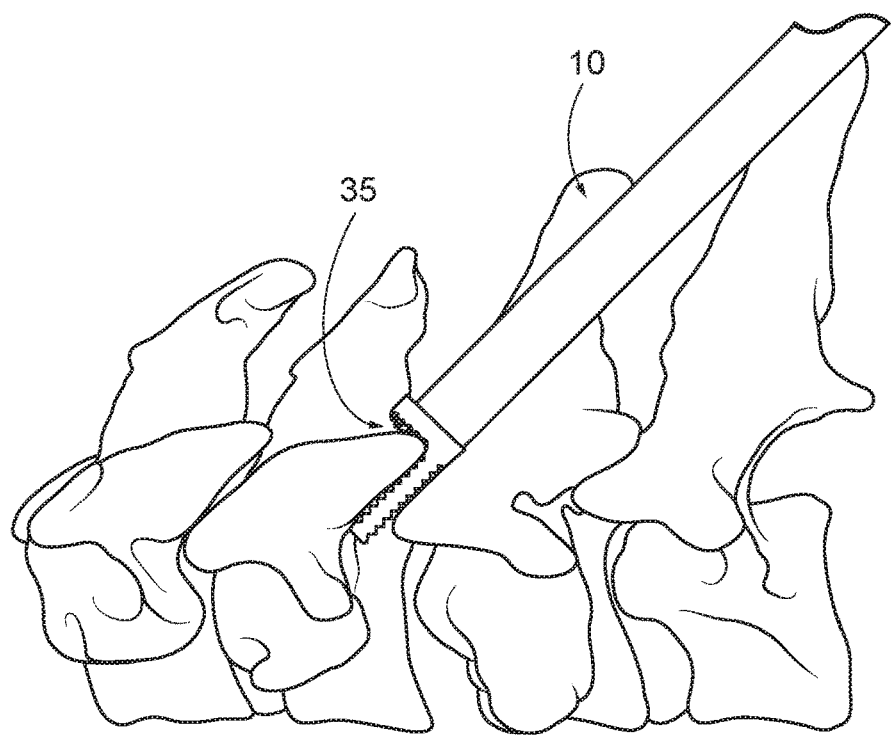
FIGS. 4D-4G are various views of the access devices of FIGS. 4A-4C in use.
Figure 4E:
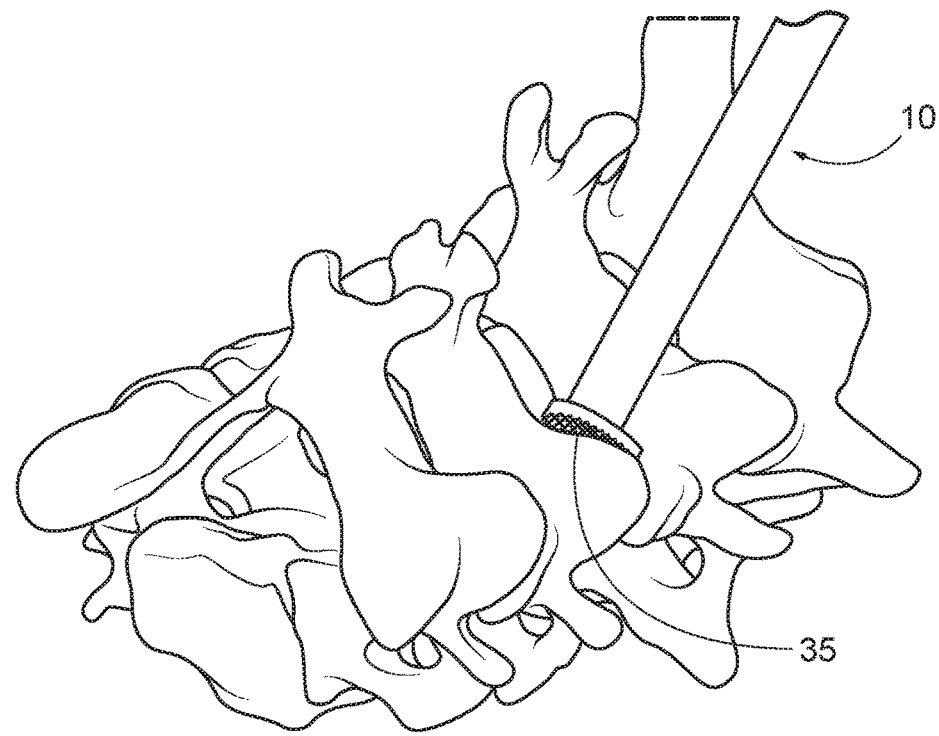
Figure 4F:
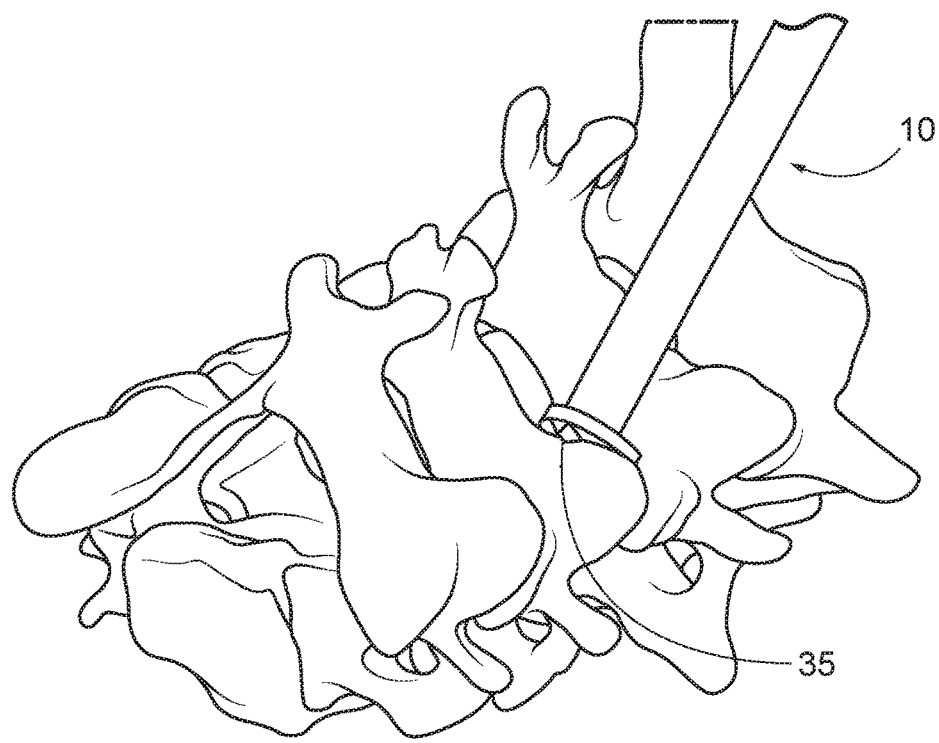
Figure 4G:
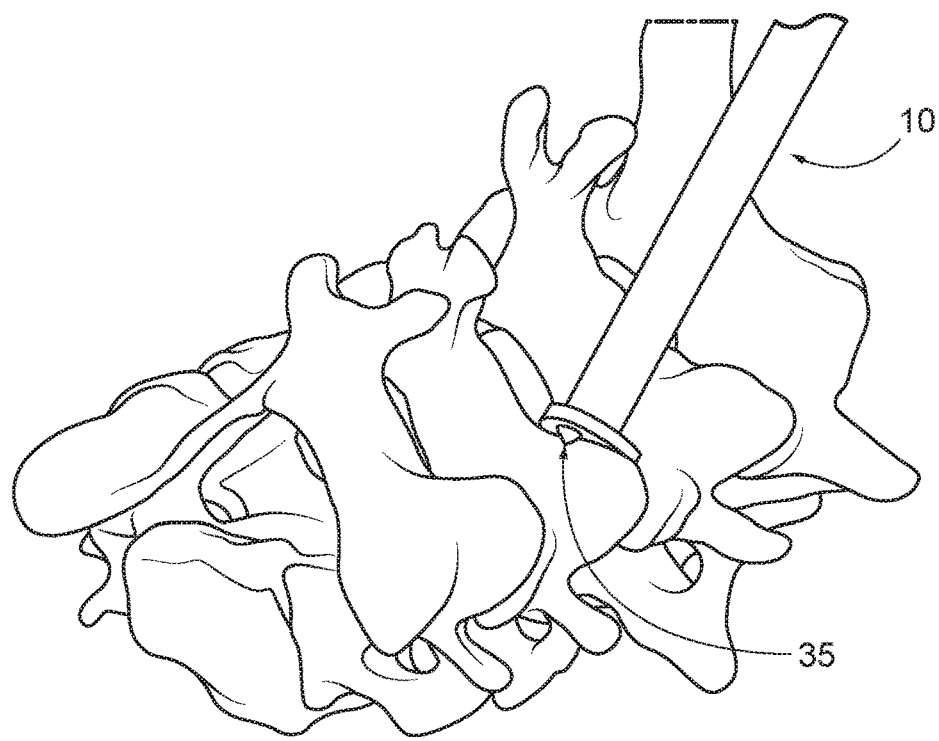

In some aspects, and as can be understood from FIGS. 4A-4G, the access device 10 includes the body 15 which may be an elongated tubular body having a proximal portion 20 and a distal portion 25. The distal portion 25 further includes a chamfered or beveled end feature 30 positioned at an end of the distal portion of the access device. The end feature 30 further includes a stop feature 35 configured to abut the posterior edge of the facet joint. The stop feature 35 may include a raised or protruding feature such as a single spike (FIG. 4C) or a plurality of spikes or teeth (FIG. 4A), such as waffle pattern spikes, or a keel (FIG. 4B). The raised or protruding feature engages the facet joint to anchor the device 10 into the facet joint. FIGS. 4D-4G illustrate the stop features depicted in FIGS. 4A-4C in use, where the device 10 is inserted in the facet joint, the stop feature 35 abuts the posterior edge of the facet joint and the raised or protruding feature engages the joint to anchor the device 10.

In some aspects, and as can be understood from FIGS. 5A-6F, the access device 10 includes the body 15 which may be an elongated tubular body having a proximal portion 20 and a distal portion 25. The distal portion 25 further includes a chamfered or beveled end feature 30 positioned at an end of the distal portion of the access device. The end feature 30 may be an expandable end feature including teeth or raised ridges 30a to engage the facet joint and/or the stop feature or the raised/protruding features described in FIG. 4.

Figure 5A:
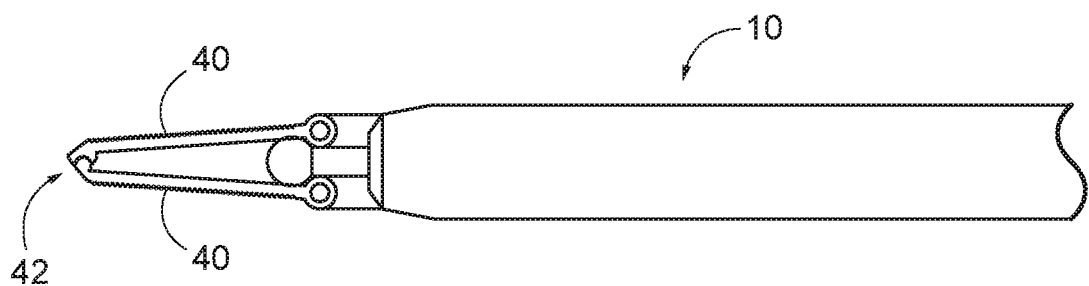
FIGS. 5A-5D are side and isometric views of an access device according to the present disclosure having an expandable end feature, where
Figure 5B:
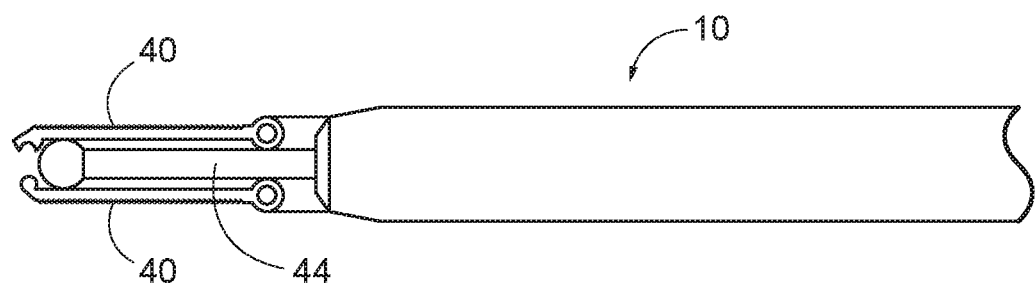
Figure 5C:
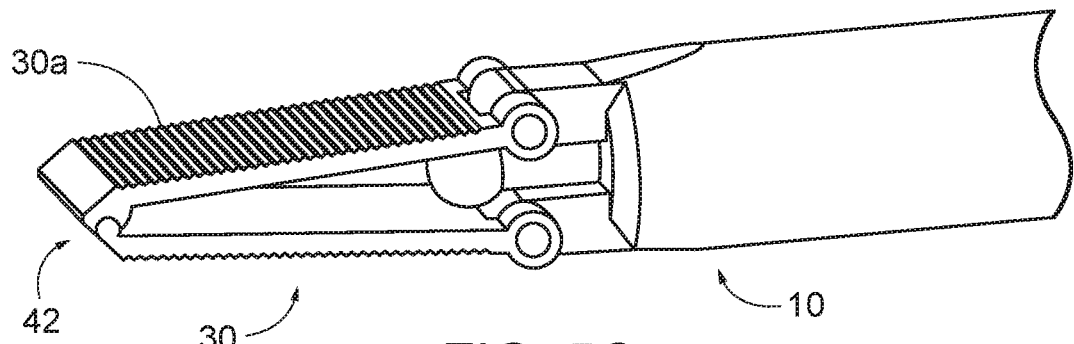
Figure 5D:
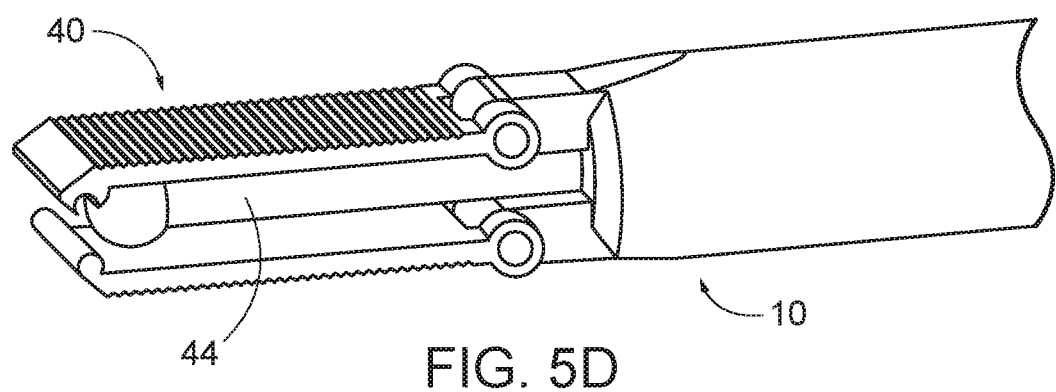
Figure 5E:
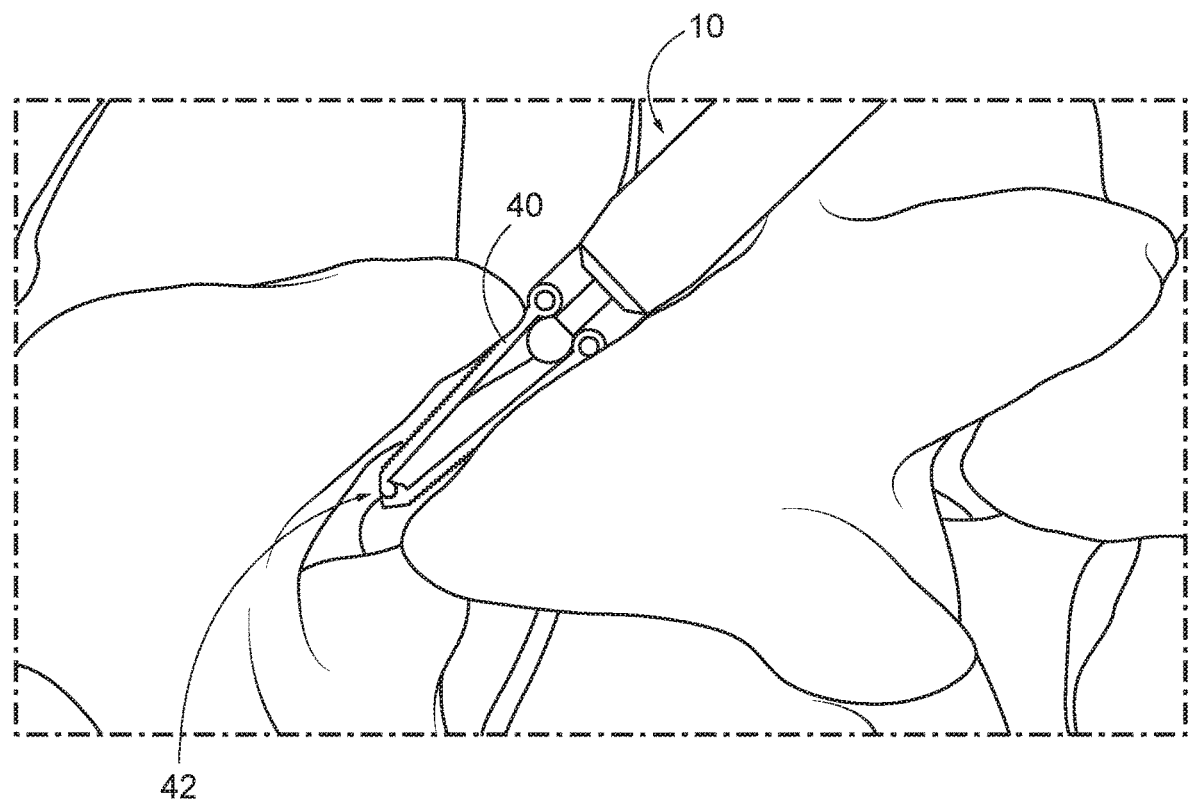
FIGS. 5E-5F show the access device of FIGS. 5A-5D in use.
Figure 5F:
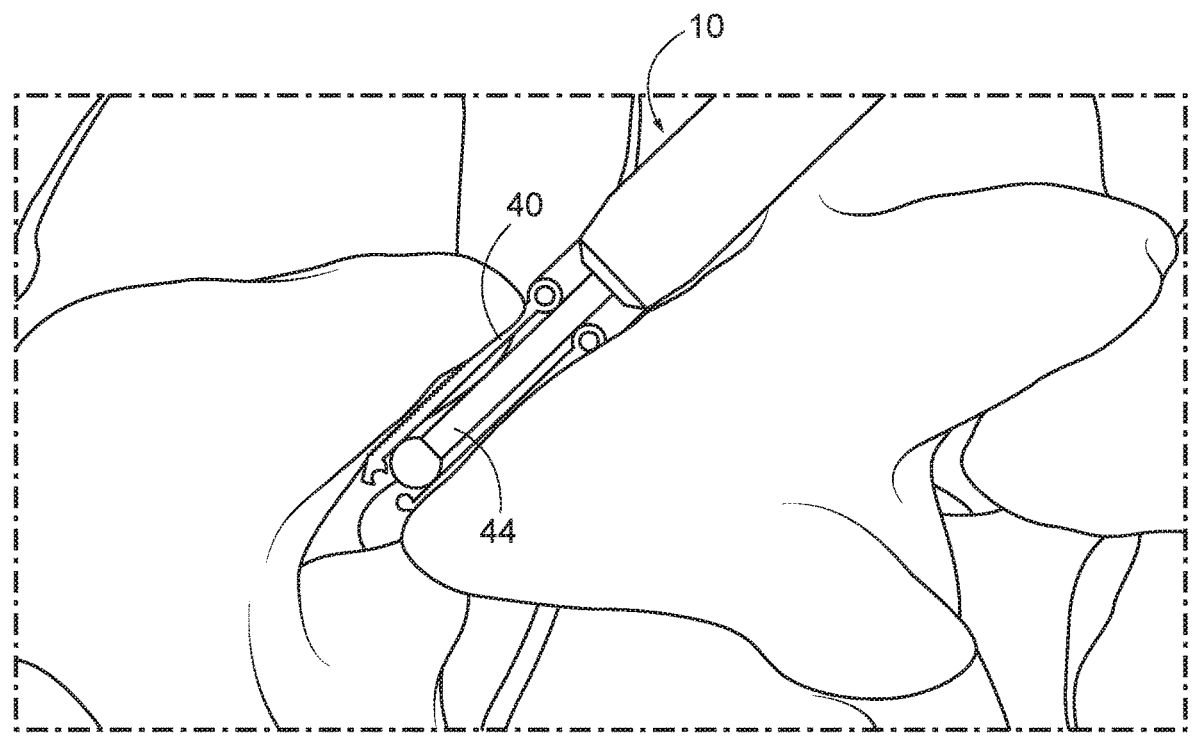

As shown in FIGS. 5A-5D, in one aspect, the end feature 30 comprises two arms 40 held in a closed position by a detent feature 42 and expanded by actuation of an internal rod 44 when positioned in the facet joint (see FIGS. 5E-5F showing placement in the facet joint). The internal rod may open the arms at a pivot point or the arms may have an internal edge with a ramp feature that is engaged by the rod as the rod is advanced distally.

Figure 6A:
FIGS. 6A-6D are side and isometric views of an access device according to the present disclosure having an expandable end feature, where
Figure 6B:
Figure 6C:
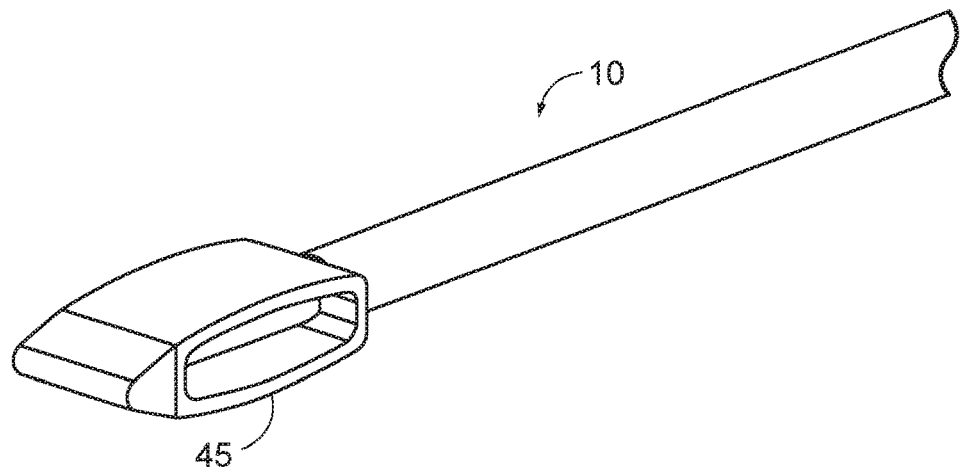
Figure 6D:
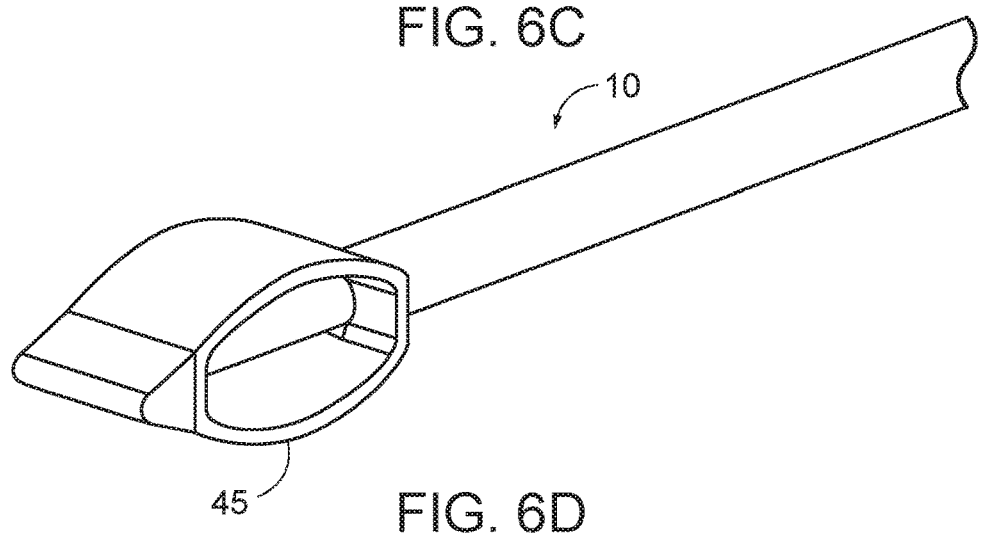
Figure 6E:
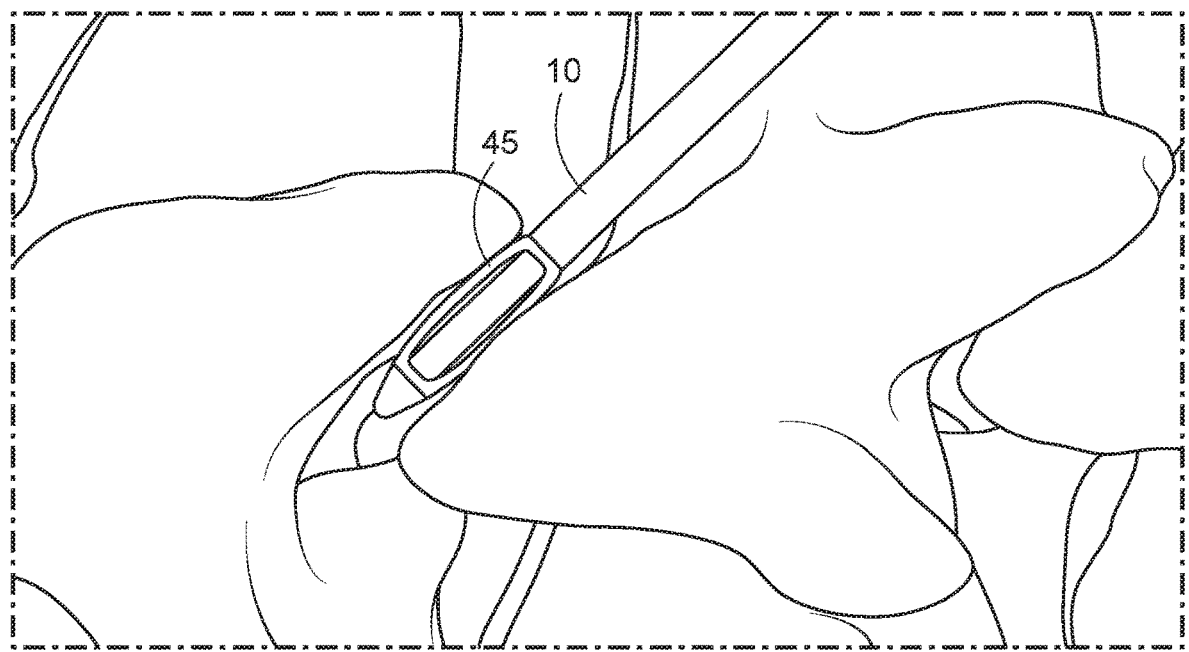
FIGS. 6E-6F show the access device of FIGS. 6A-6D in use.
Figure 6F:
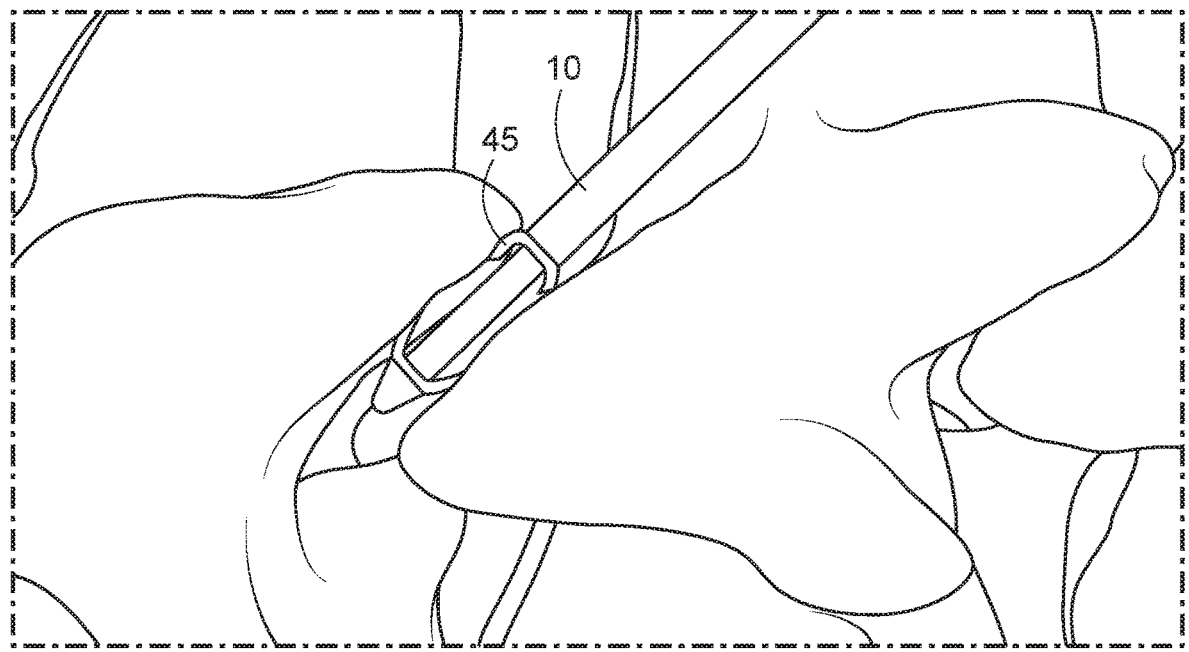

As illustrated in FIGS. 6A-6D, in another aspect, the end feature comprises an expandable member 45 that is delivered in a flat or closed position (see FIG. 6E) and is expanded or opened once in position in the facet joint (FIG. 6F). The expandable member is opened via an inner rod connected to the tip that is actuated proximally to compress the expandable member. Alternatively, an outer rod actuates distally to compress the expandable member. The expandable member is made of nitinol, stainless steel, spring steel or other metal or metal alloy that can expand and contract without permanent deformation.

Figure 7A:
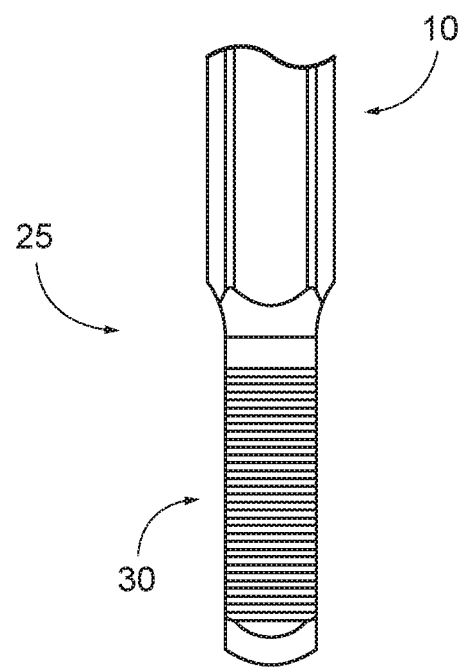
FIGS. 7A-7B are top and lateral views of an access device according to the present disclosure having an end feature with a rigid tip.
Figure 7B:
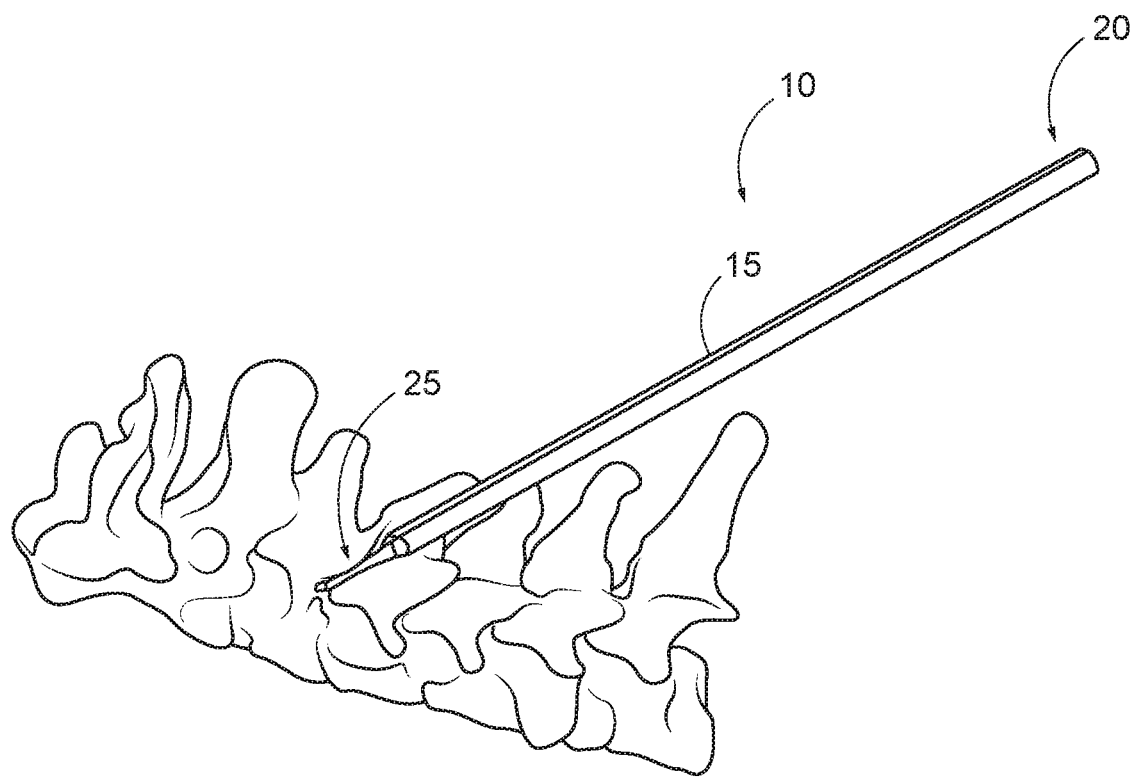
Figure 7C:
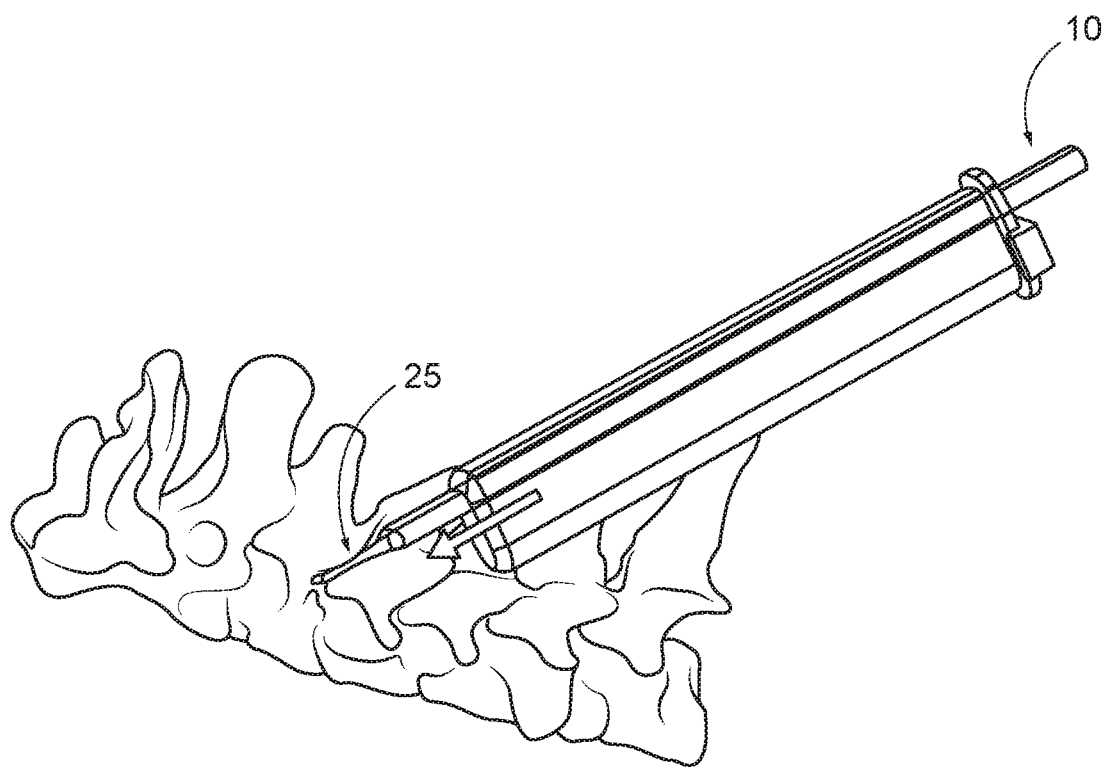
FIG. 7C is the device of FIG. 7A-7B in use.

In some aspects, and as can be understood from FIGS. 7A-7C, the access device 10 includes the body 15 which may be an elongated body having a proximal portion 20 and a distal portion 25. The distal portion 25 further includes a chamfered or beveled end feature 30 positioned at an end of the distal portion of the access device. The end feature 30 may be a rigid tip 50 (7A). In use, and as seen in FIGS. 7B-7C, the device 10 is inserted in the facet space and is used in conjunction with other instruments (such as the guide tube shown in FIG. 7C) to guide a screw (depicted by an arrow in FIG. 7C) into the lateral mass at the same angle as the facet joint.

In some aspects, and as can be understood from FIGS. 8A-12H, the access device 10 includes the body 15 which may be an elongated body having a proximal portion 20 and a distal portion 25. The distal portion 25 further includes a chamfered or beveled end feature 30 positioned at an end of the distal portion of the access device. The end feature 30 may include an articulating tip 50.

Figure 8A:
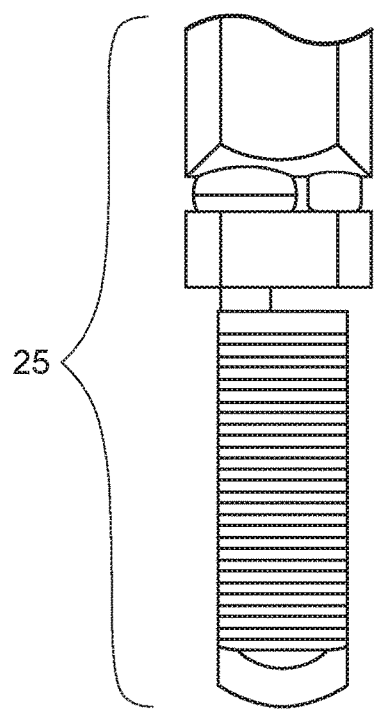
FIGS. 8A-8B are top and isometric views of an access device according to the present disclosure having an end feature with an articulating tip.
Figure 8B:
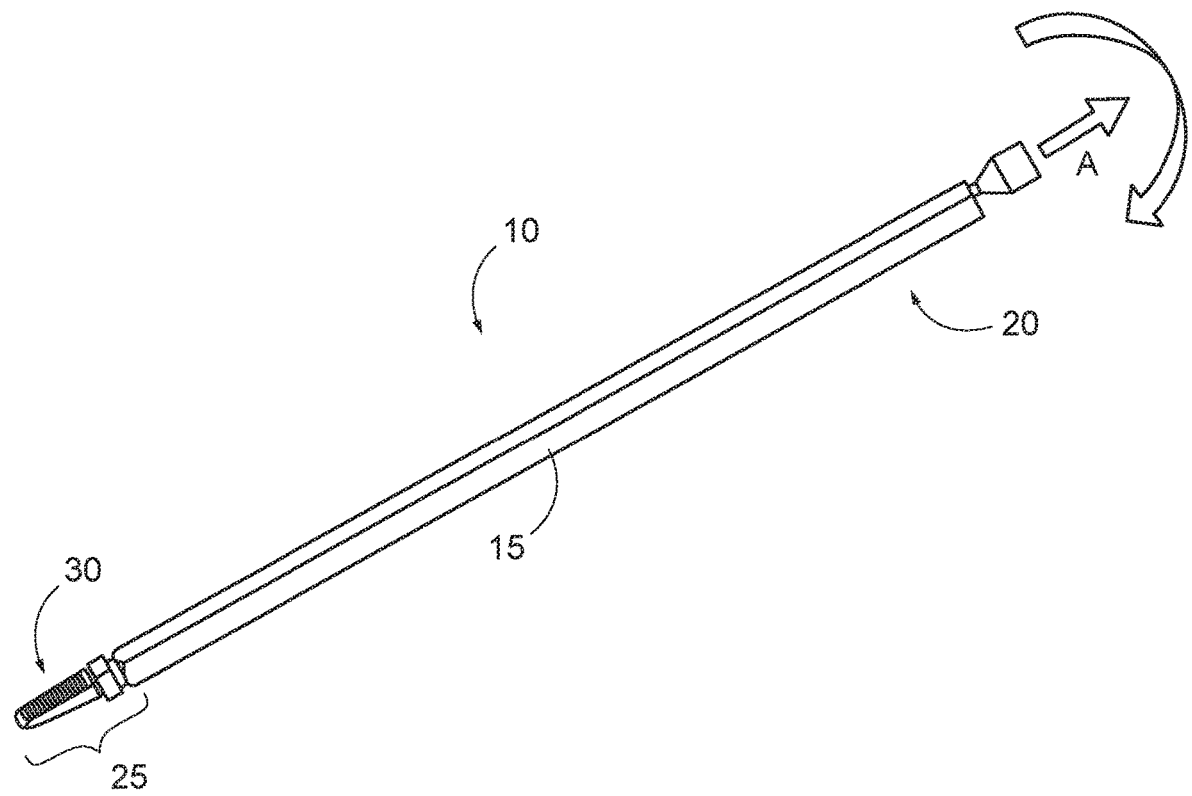
Figure 8C:
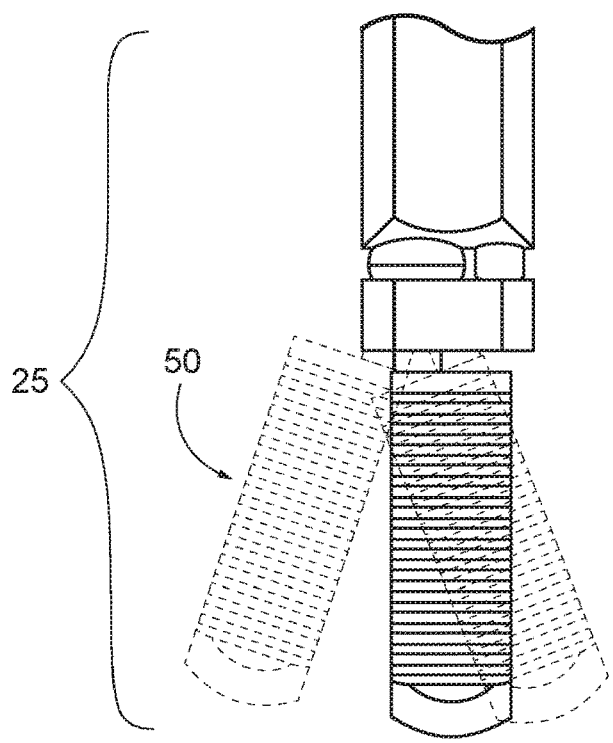
FIGS. 8C-8F are enlarged views of the tip of FIGS. 8A-B, in unlocked (FIGS. 8C-D) and locked (FIG. 8E-F) positions.
Figure 8D:
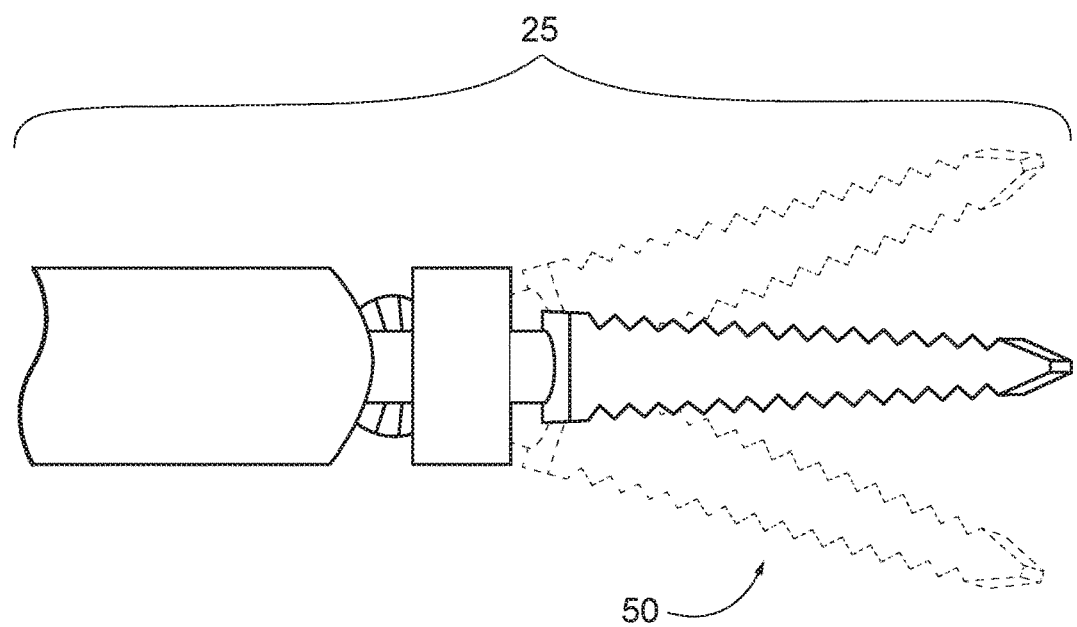
Figure 8E:
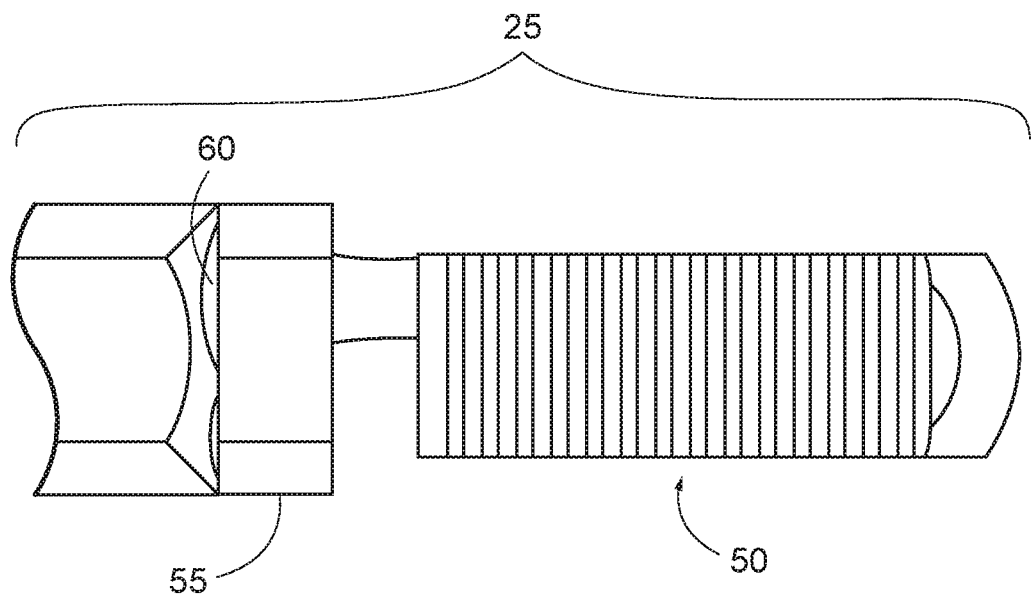
Figure 8F:
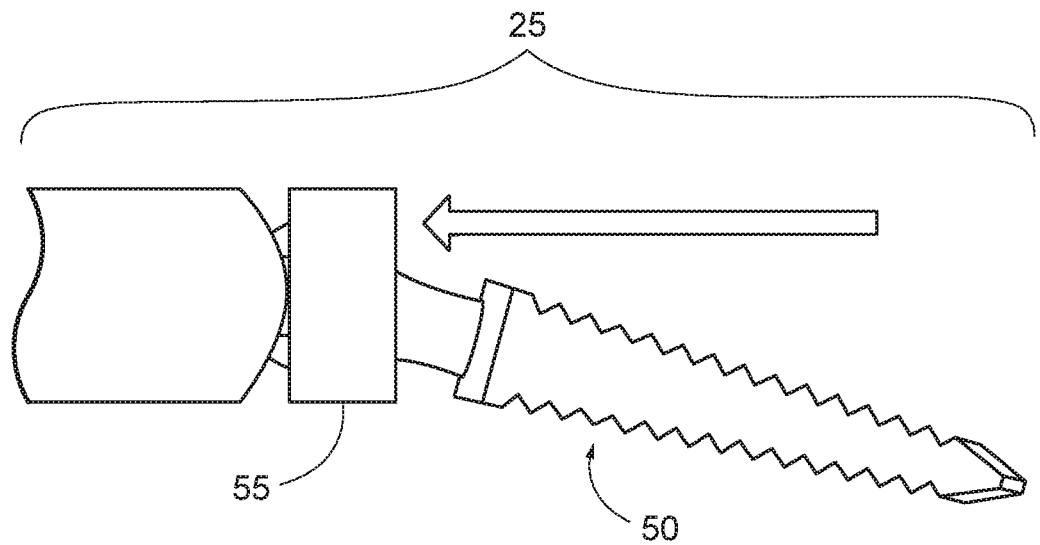
Figure 8G:
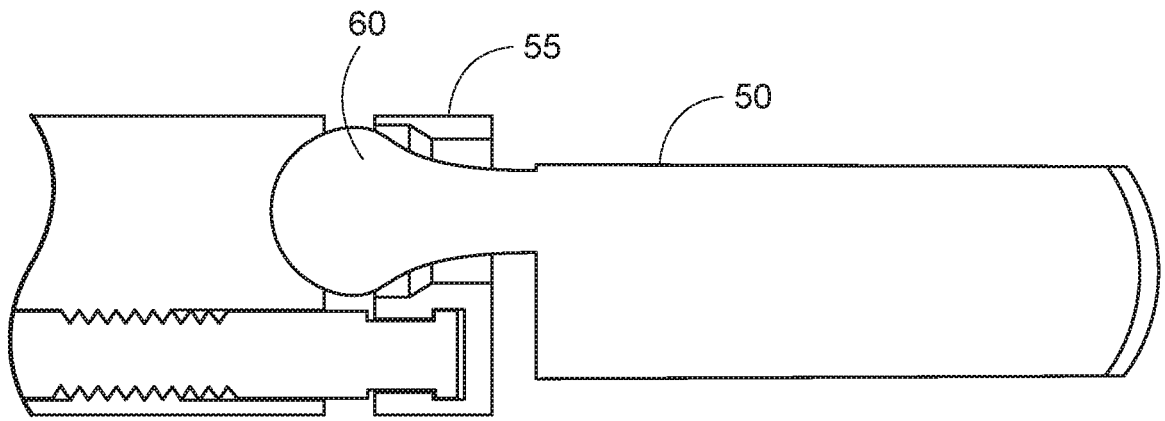
FIGS. 8G-H are cross-section views of the tip of FIGS. 8C-8F.
Figure 8H:
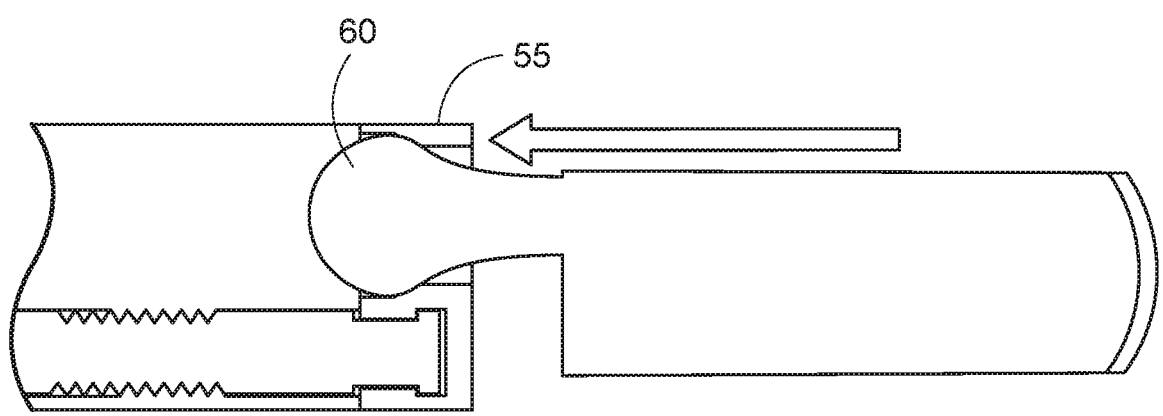

As indicated in FIG. 8A, the articulating tip 50 may comprise a locking ball joint with plate. As shown in FIG. 8B, the user pulls in the direction of arrow A and rotates the handle clockwise to lock the articulating tip into place. FIGS. 8C-8D show the articulating tip in an open or unlocked position in which the tip is permitted to rotate freely. FIG. 8E-8F show the articulating tip in a locked position. The plate 55 is engaged with the ball joint 60 which locks the tip 50 in place. FIGS. 8G-8H illustrate section views, with FIG. 8G showing the tip 50 in an open position, where the plate 55 is not engaged with a ball joint 60. FIG. 8H shows the plate 55 is locked into place via threads along the shaft of the distal portion of the body 15. The ball joint 60 is engaged with the plate 55.

Figure 9A:
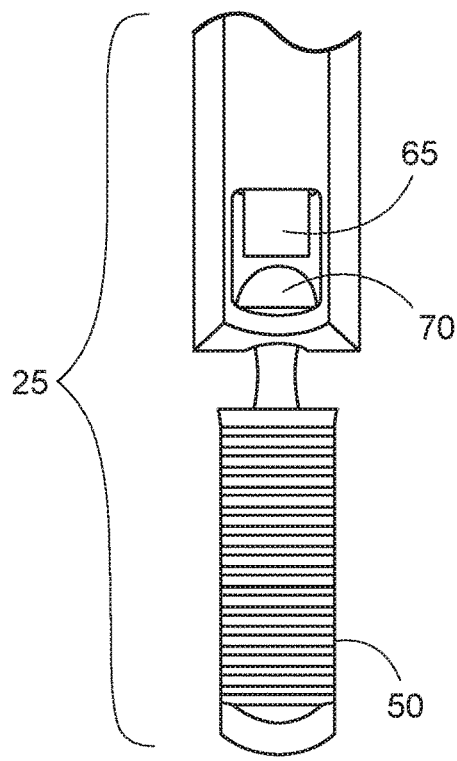
FIGS. 9A-9B are top and isometric views of an access device according to the present disclosure having an end feature with an articulating tip.
Figure 9B:
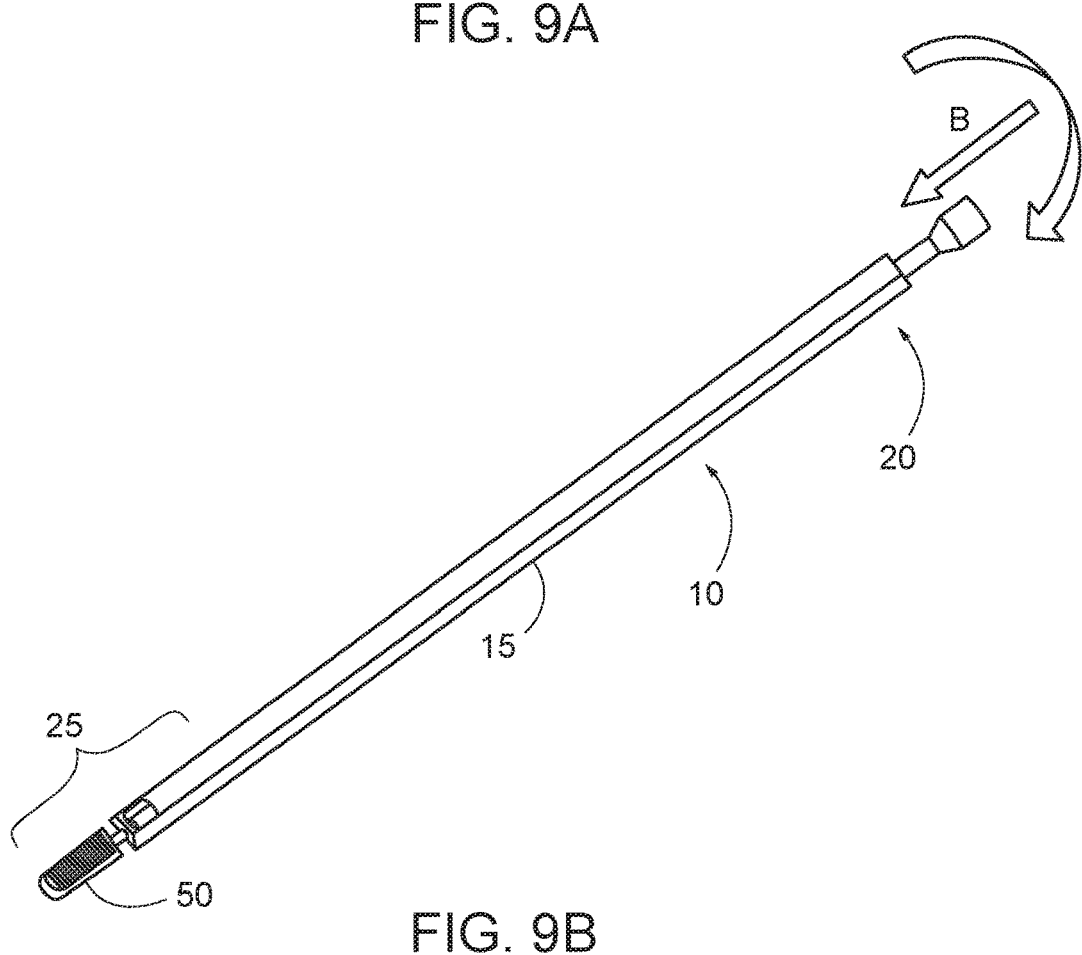
Figure 9C:
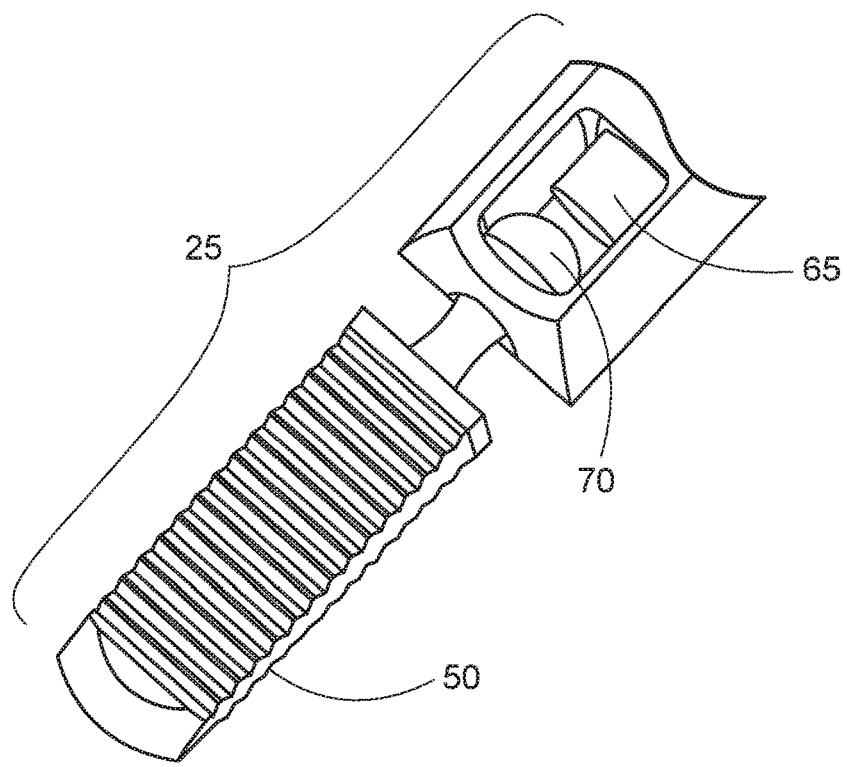
FIGS. 9C-9E are enlarged views of the tip of FIGS. 9A-B, in unlocked (FIGS. 9C-D) and locked (FIG. 9E) positions.
Figure 9D:
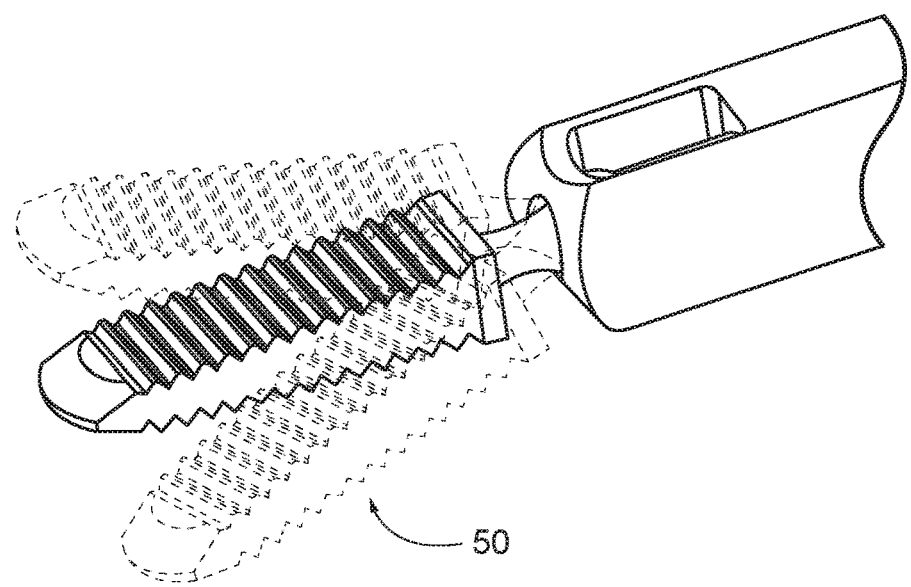
Figure 9E:
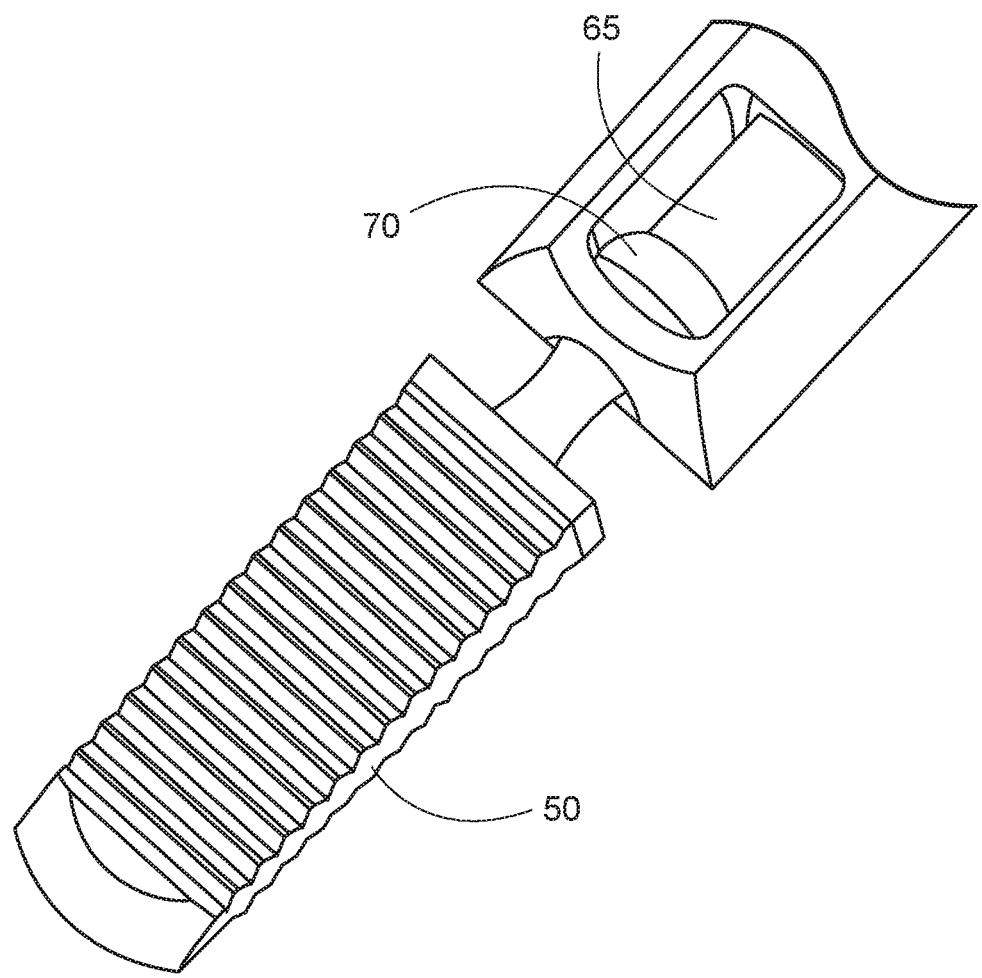
Figure 9F:
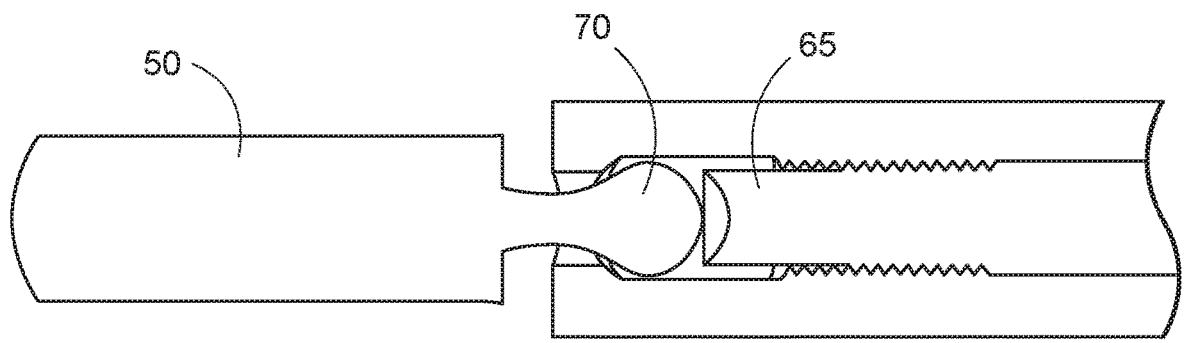
FIGS. 9F-G are cross-section views of the tip of FIGS. 9C-9E.
Figure 9G:
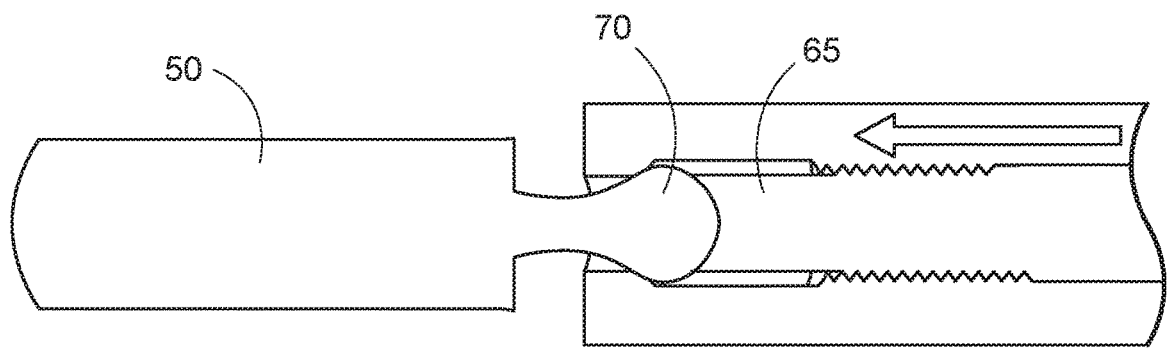

As indicated in FIG. 9A, the articulating tip 50 comprise a locking ball joint with a housing. As shown in FIG. 9B, the user pushes down on the handle in the direction of arrow B and rotates the handle clockwise to lock the articulating tip in place. FIGS. 9C-9D show the articulating tip 50 in an open or unlocked position in which the tip is permitted to rotate freely. FIG. 9E shows the tip 50 in a locked position. As shown, a rod 65 is engaged with a ball joint 70, thereby locking the tip 50 in place. FIGS. 9F-9G illustrate section views, with FIG. 9F showing the tip 50 in an unlocked position, where the rod 65 is disengaged with the ball joint 70 and tip 50. FIG. 9G shows the tip 50 in a locked position where the rod 65 is engaged with the ball joint 70 and tip 50.

Figure 10A:
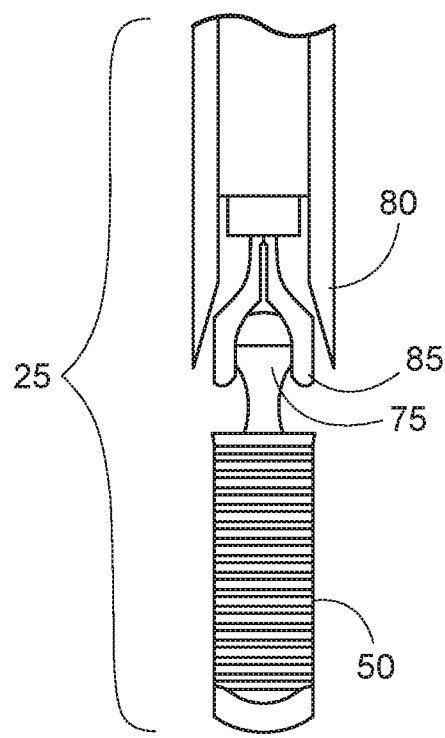
FIGS. 10A-10B are top and isometric views of an access device according to the present disclosure having an end feature with an articulating tip.
Figure 10B:
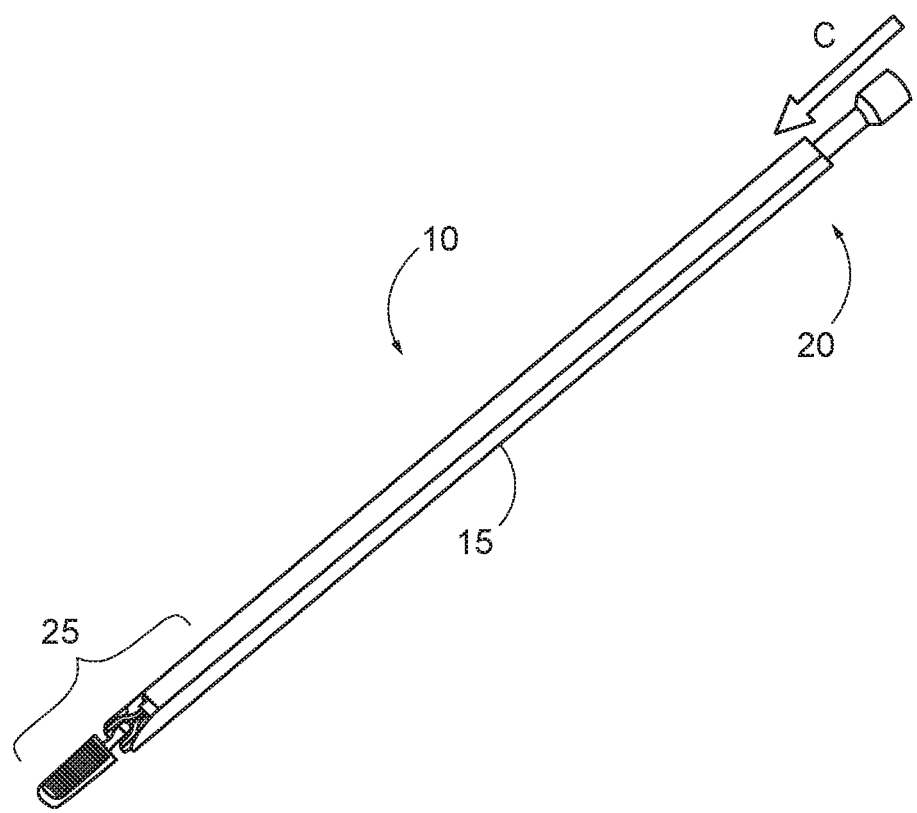
Figure 10C:
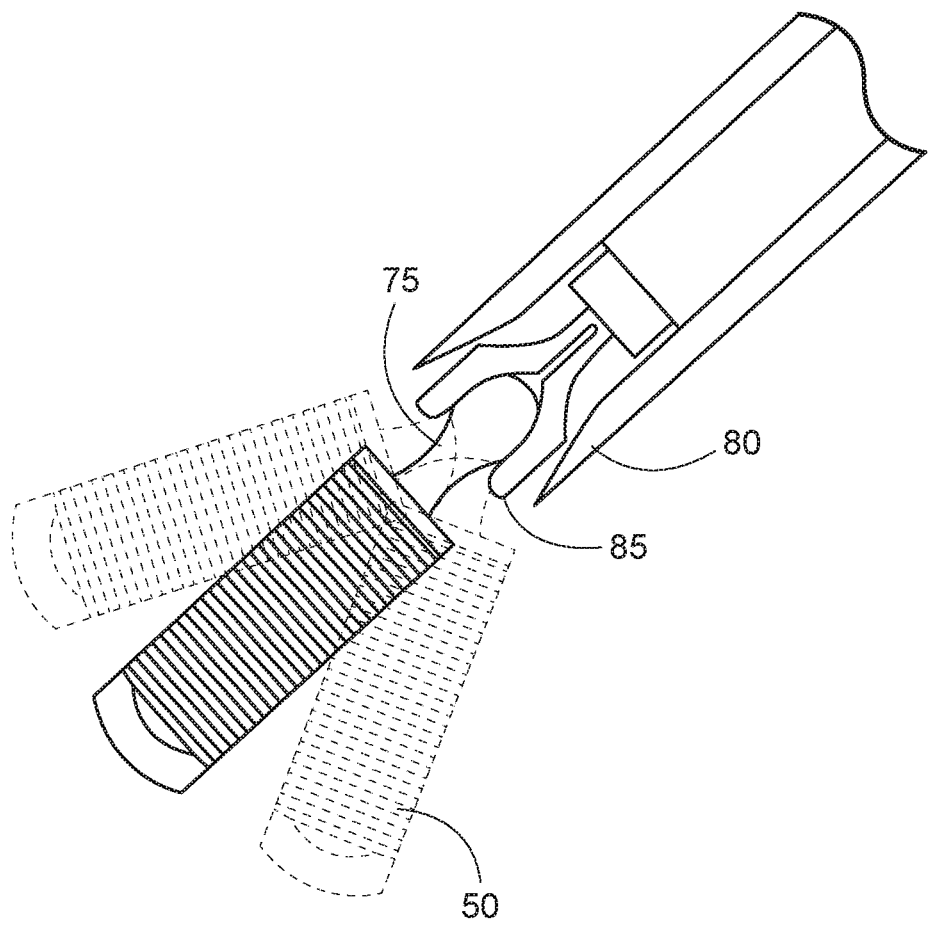
FIGS. 10C-10D are enlarged views of the tip of FIGS. 10A-B, in unlocked (FIG. 10C) and locked (FIG. 10D) positions.
Figure 10D:
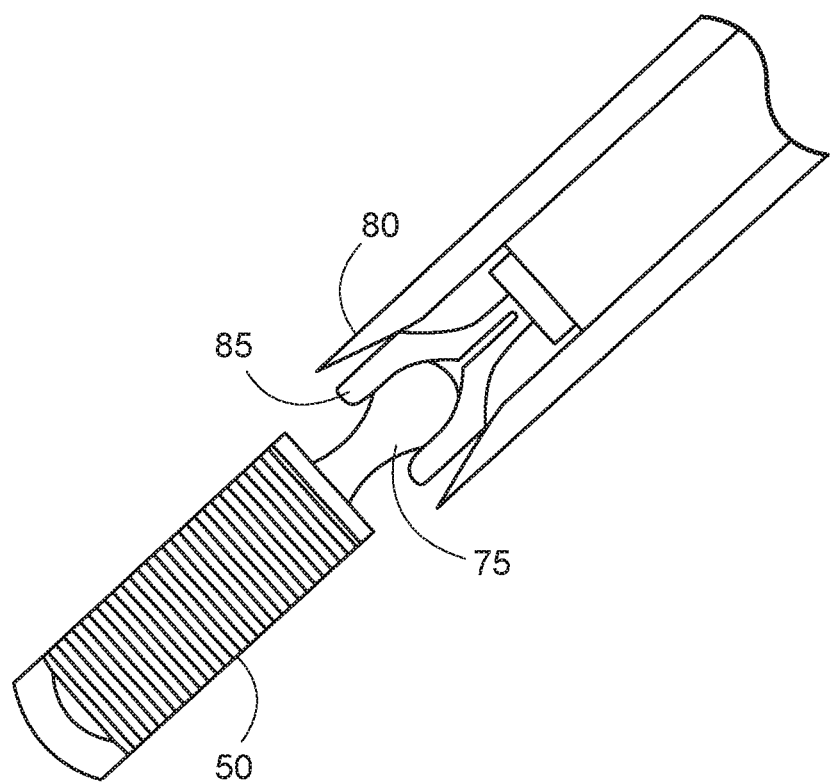
Figure 10E:
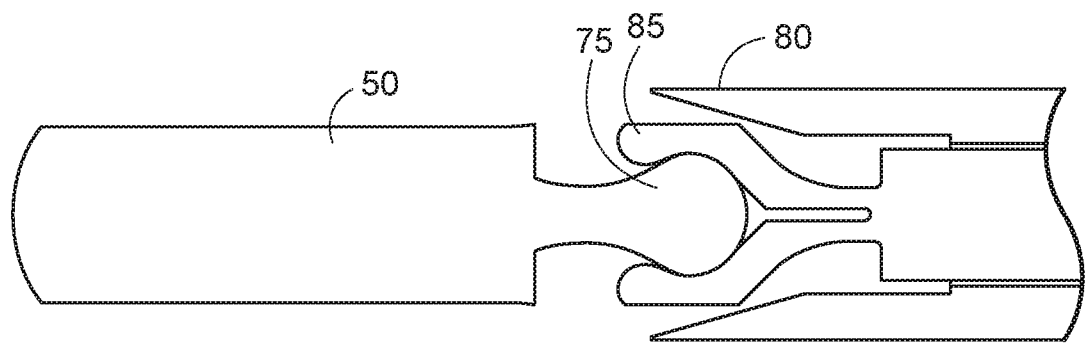
FIGS. 10E-F are cross-section views of the tip of FIGS. 10C-D.
Figure 10F:
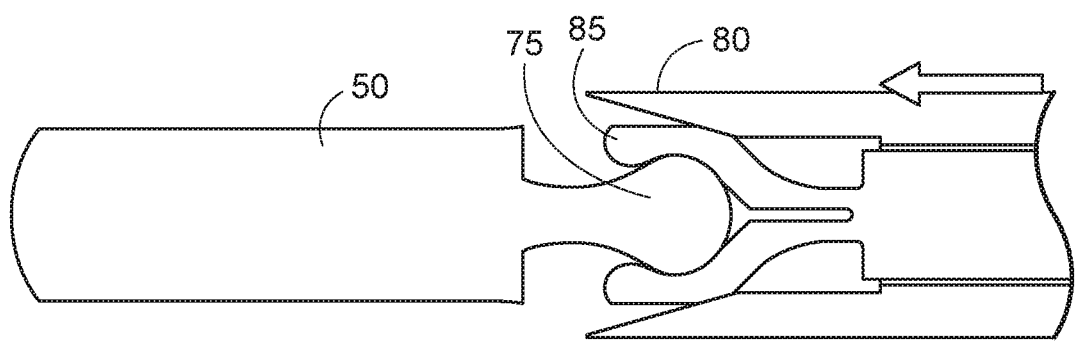

As indicated in FIG. 10A, the articulating tip 50 comprises a sleeve 80 with a tulip 85. As shown in FIG. 10B, the user presses down on the handle in the direction of arrow C to lock the articulating tip 50 in place. FIG. 10C show the articulating tip 50 in an open or unlocked position in which the tip is permitted to rotate freely. FIG. 10D shows the tip in a locked position. As shown, a sleeve 80 and tulip 85 are engaged with a ball joint 75 thereby locking the tip 50 in place. FIGS. 10E-10F illustrate section views, with FIG. 10E showing the tip 50 in an unlocked or open configuration. The sleeve is disengaged with the locking tulip and the tip 50 is able to freely rotate. FIG. 10F shows the tip in a locked position. The sleeve 80 is engaged with the locking tulip 85 thereby locking the ball joint 75 and thereby the tip 50 in place.

Figure 11A:
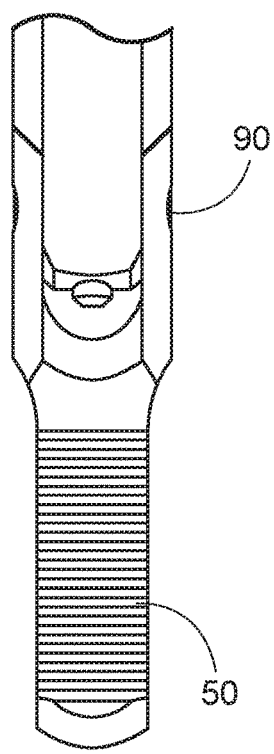
FIGS. 11A-11B are top and isometric views of an access device according to the present disclosure having an end feature with an articulating tip.
Figure 11B:
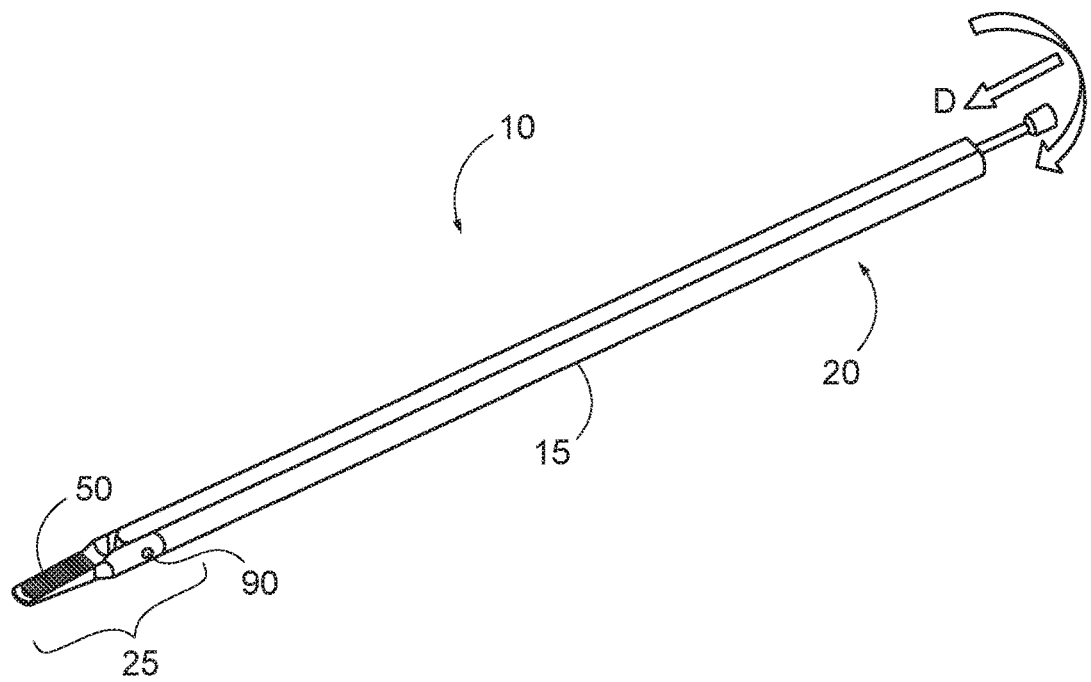
Figure 11C:
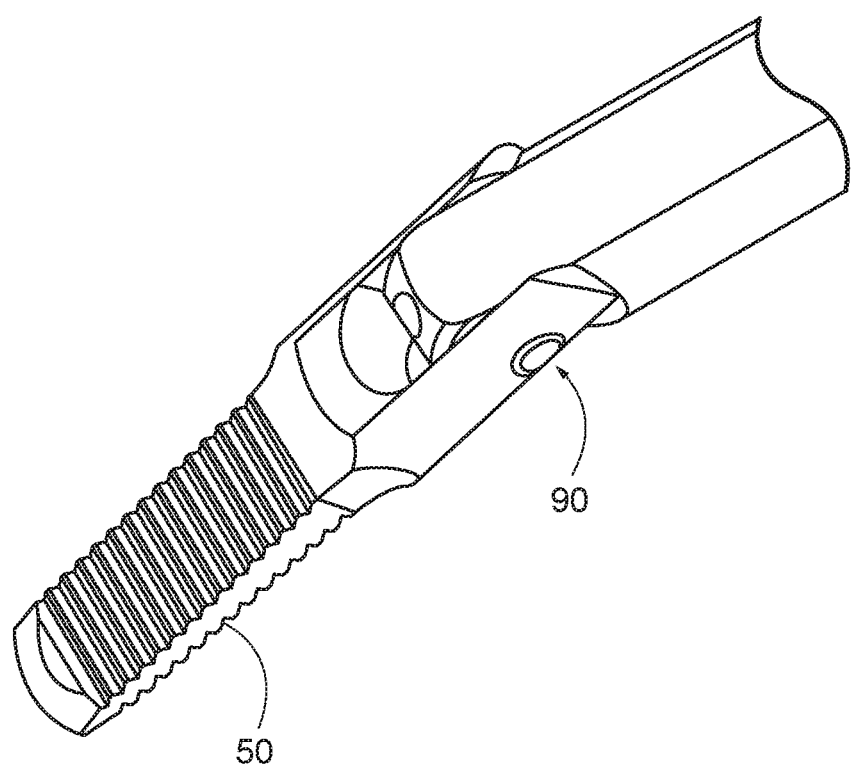
FIGS. 11C-11H are enlarged or transparent views of the tip of FIGS. 11A-B, in unlocked (FIGS. 11C, 11E-F) and locked (FIG. 11D, 11G-H) positions.
Figure 11D:
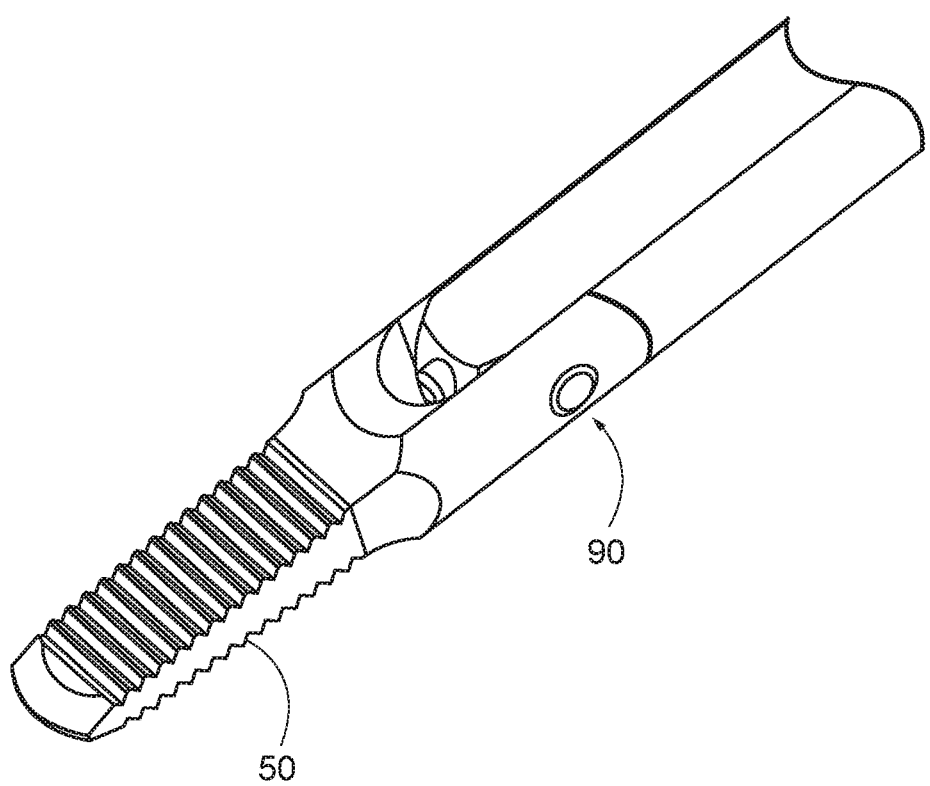
Figure 11E:
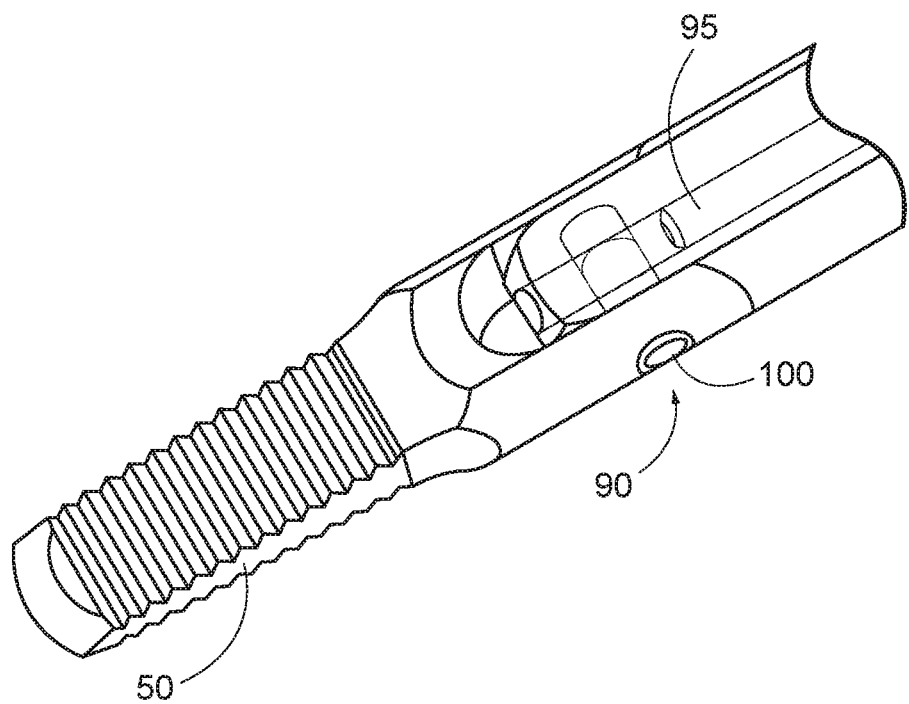
Figure 11F:
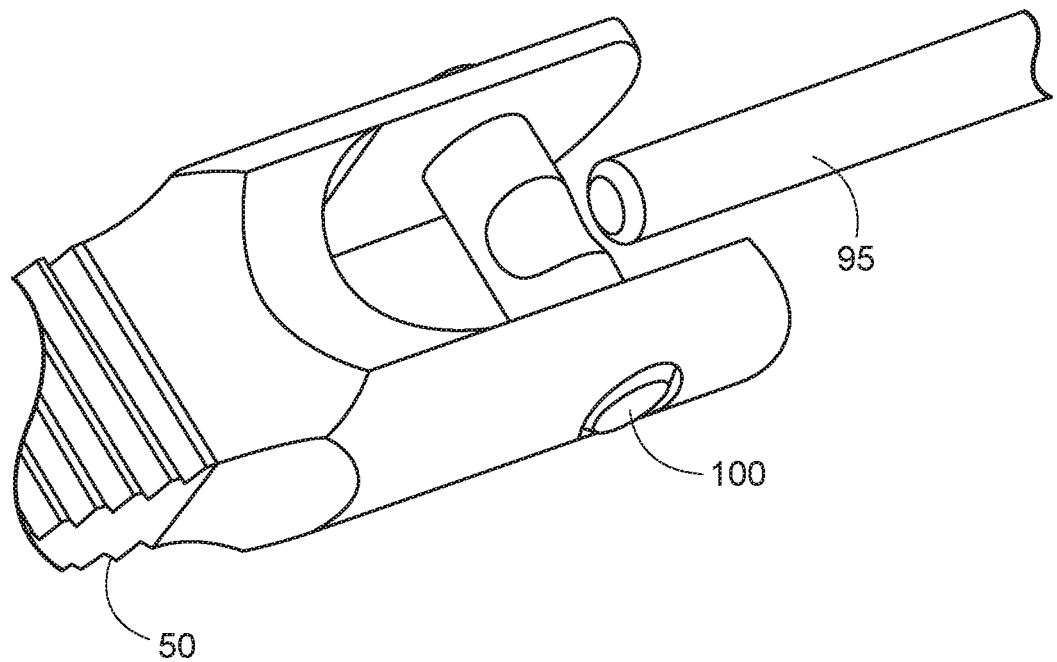
Figure 11G:
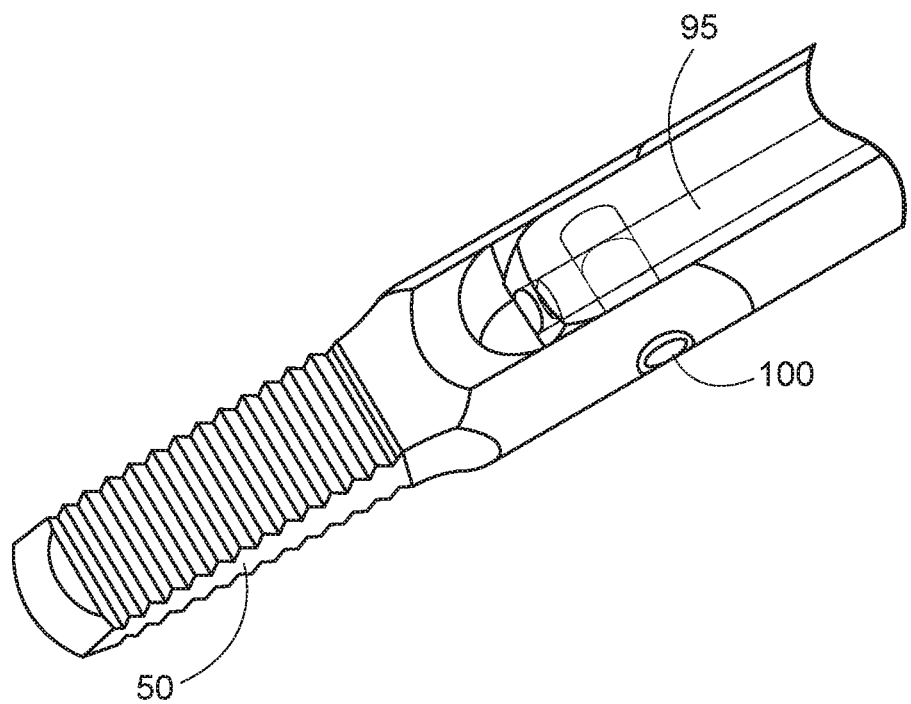
Figure 11H:
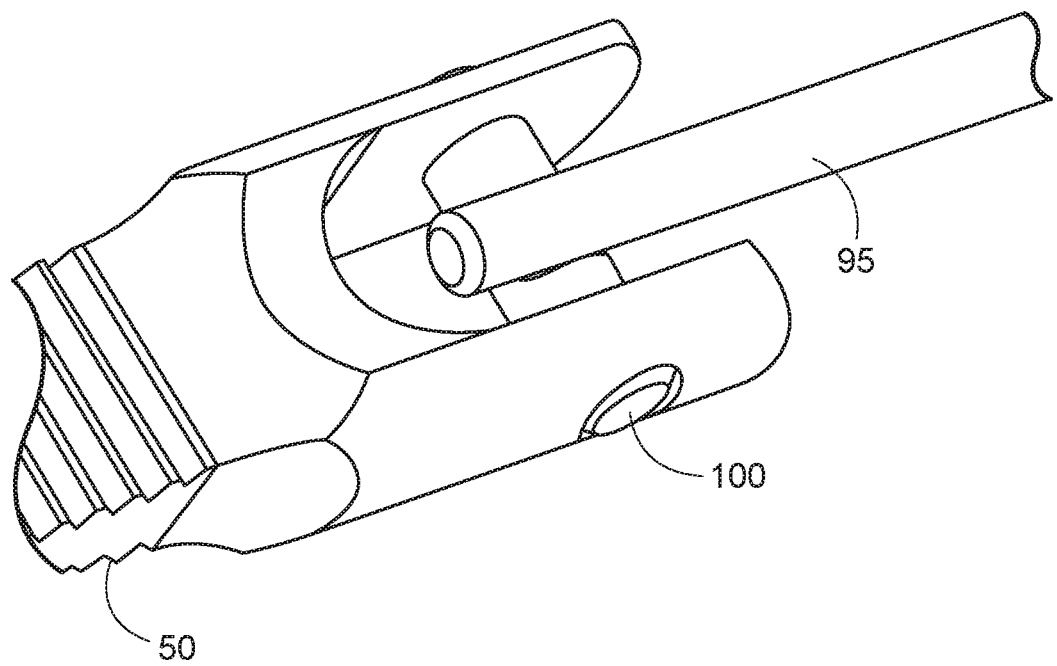

As indicated in FIG. 11A, the articulating tip 50 comprises a single direction pivot 90. As shown in FIG. 11B, the user pushes down on the handle in the direction of arrow D, and turns the handle clockwise to lock the tip 50 in place. FIG. 11C illustrates the tip 50 in an open or unlocked position. FIG. 11D illustrates the tip 50 in a closed or locked position. FIGS. 11E-F are transparent and enlarged views showing the tip 50 in an unlocked position. A rod 95 is not engaged with a locking dowel pin 100 and the tip 50 is able to rotate along the coronal plane. FIGS. 11G-H are transparent and enlarged views showing the tip 50 in a locked position. The rod 95 is pushed forward to interact with the locking dowel pin 100 thereby locking the tip 50 in one position in the coronal plane.

Figure 12A:
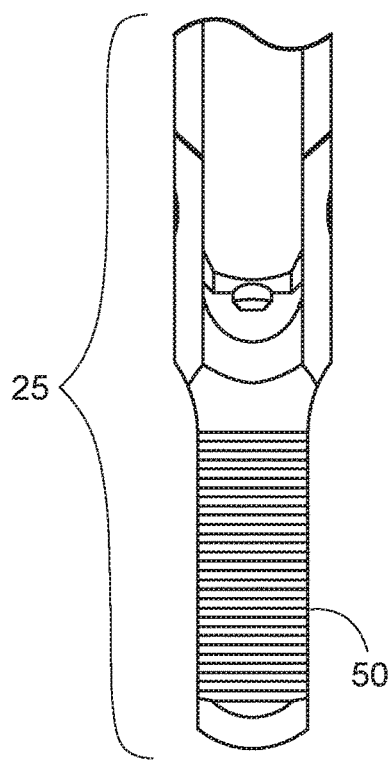
FIGS. 12A-12B are top and isometric views of an access device according to the present disclosure having an end feature with an articulating tip.
Figure 12B:
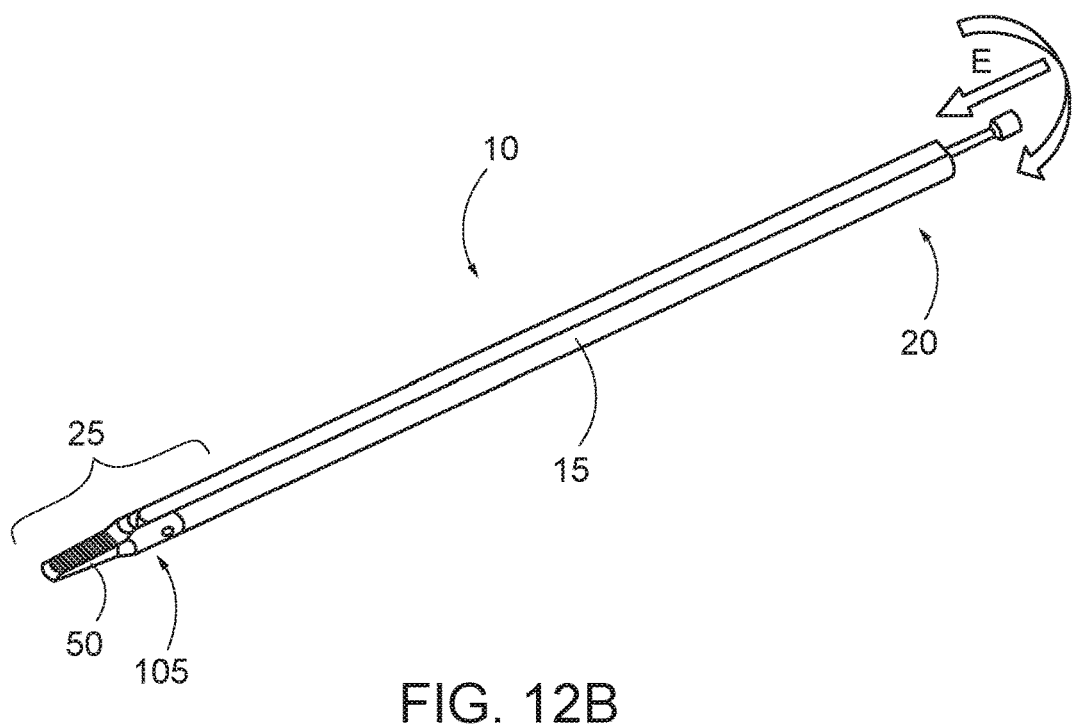
Figure 12C:
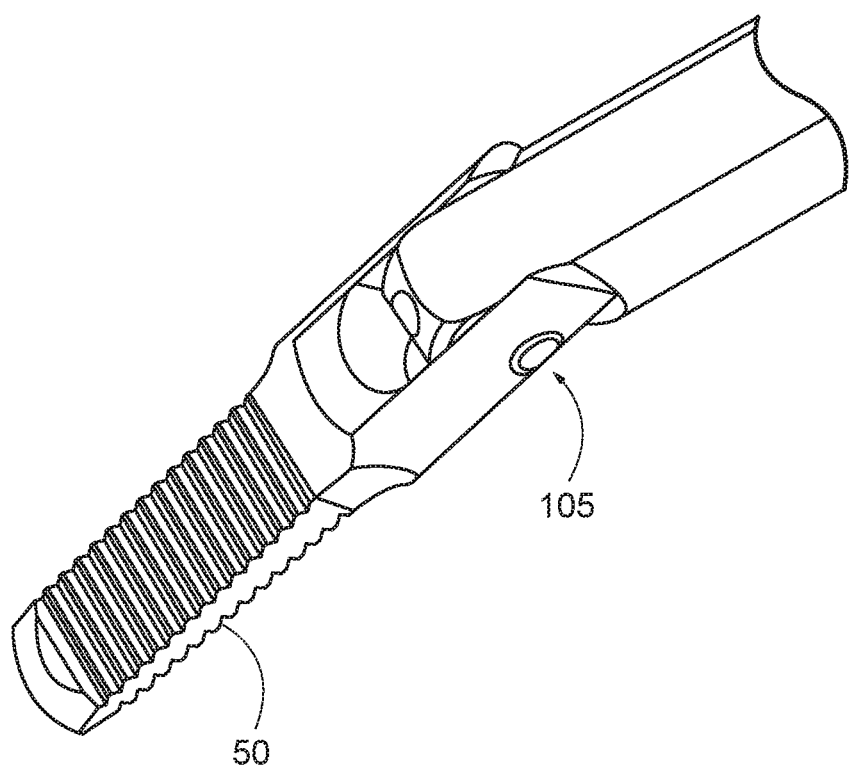
FIGS. 12C-12H are enlarged or transparent views of the tip of FIGS. 12A-B, in unlocked (FIGS. 12C, 12E-F) and locked (FIGS. 12D, 12G-H) positions.
Figure 12D:
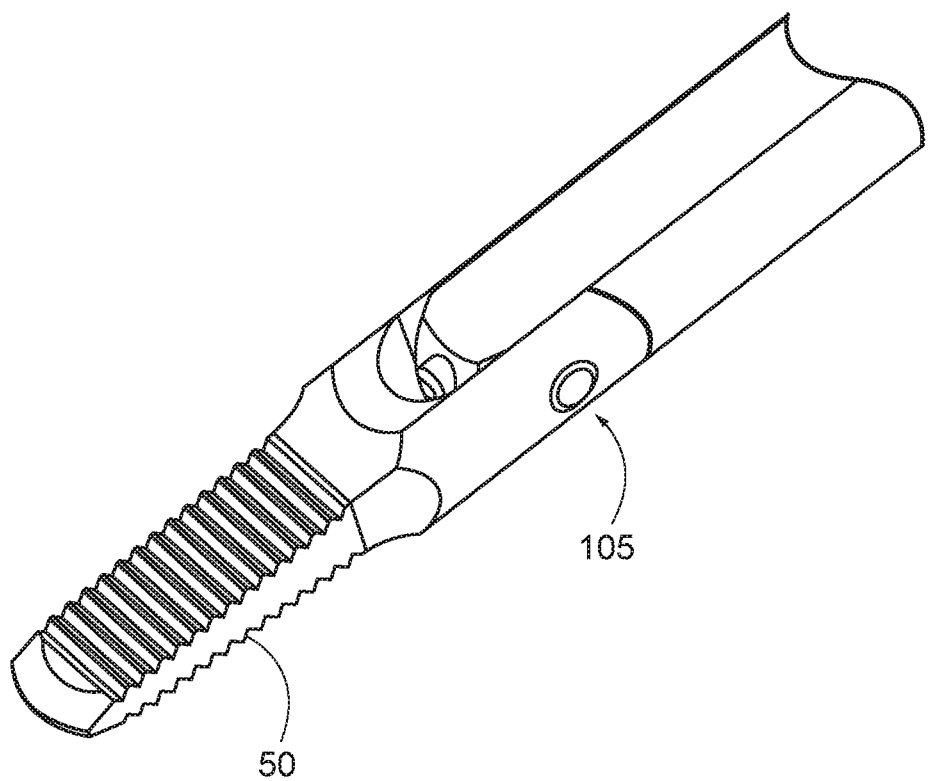
Figure 12E:
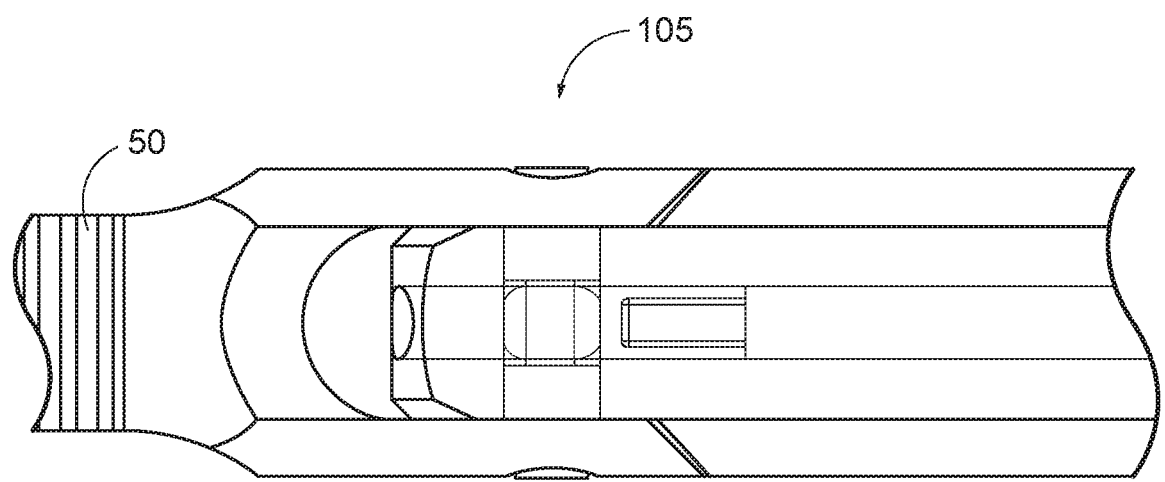
Figure 12F:
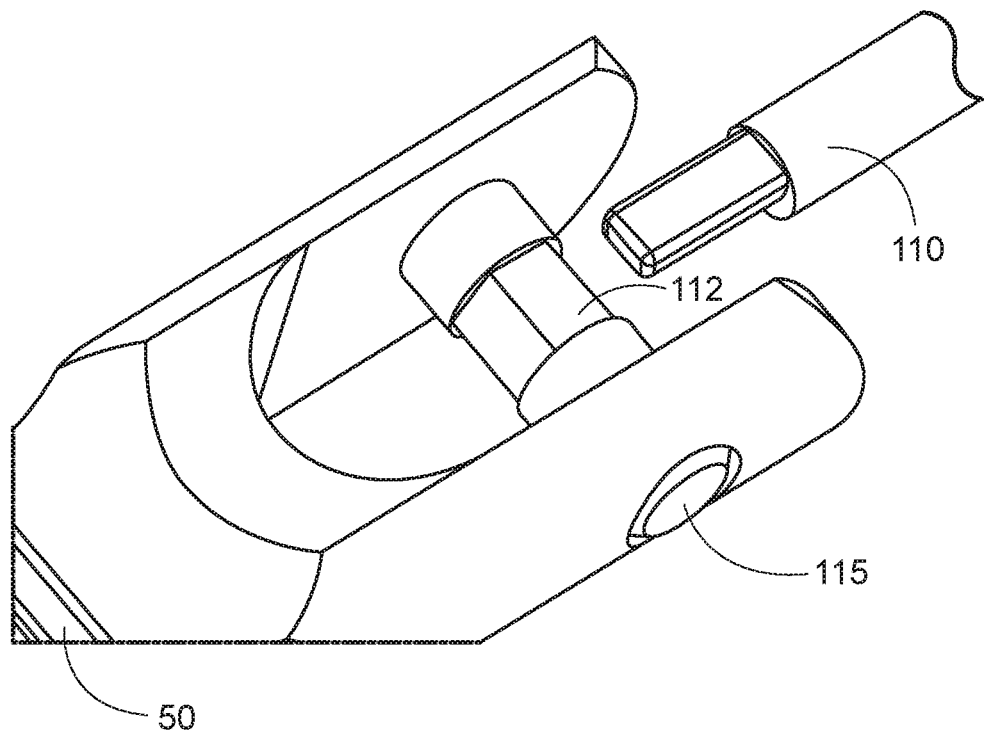
Figure 12G:
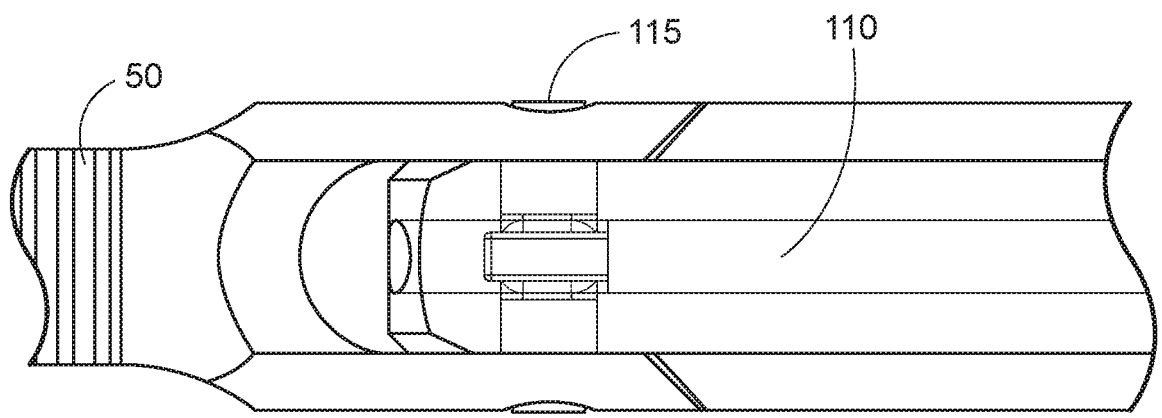
Figure 12H:
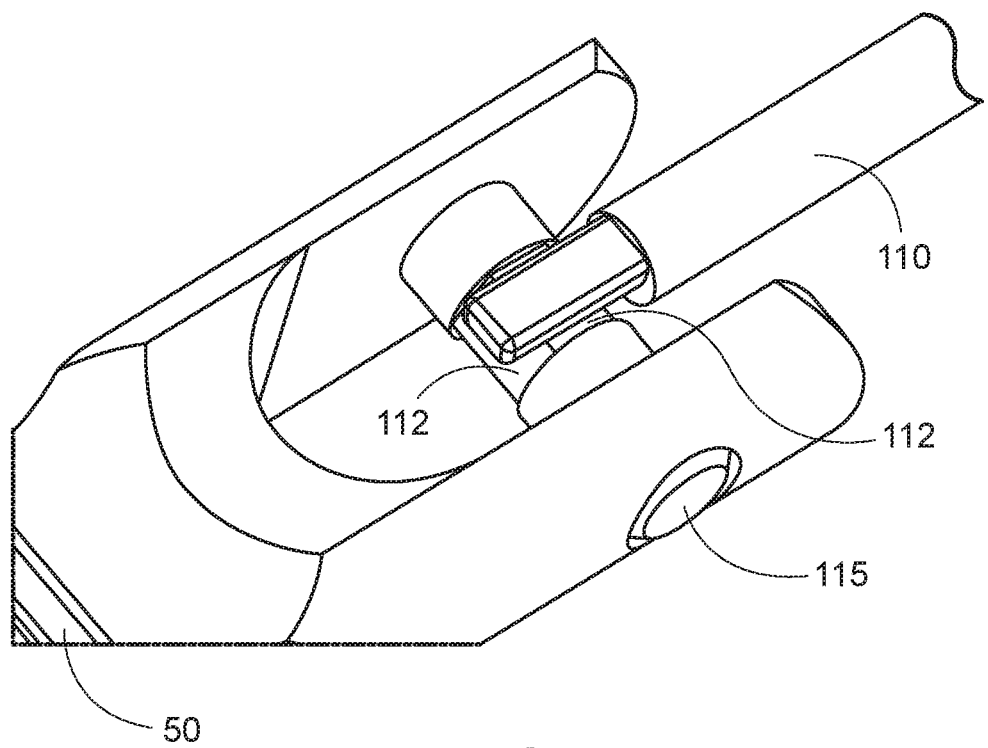

As indicated in FIG. 12A, in some aspects, the articulating tip 50 comprises a locking wheel 105. As shown in FIG. 12B, the user pushes down on the handle in the direction of arrow E and turns the handle clockwise to lock the tip in place. FIG. 12C illustrates the tip 50 in an open or unlocked position. FIG. 12D illustrates the tip 50 in a closed or locked position. FIGS. 12E-F are transparent and exploded views showing the tip in an unlocked position. A rod 110 is disengaged from a locking feature 112 on a dowel pin 115 thereby allowing the tip 50 to rotate freely. FIGS. 12G-H are transparent and exploded view showing the tip 50 in a locked position. The rod 110 is pushed forward to interact with the flat locking feature 112 of the dowel pin 115 thereby locking the tip 50 into place. Depending on which portion of the flat locking feature is engaged, the tip 50 can be locked in one of six different positions in the coronal plane. In other embodiments, the flat locking feature may have more than six positions or less than six positions.

As noted above, the access device may be used with other tools to deliver a spinal fixation device. The delivery may be achieved with, for example, a guide portal or device.

Figure 13A:
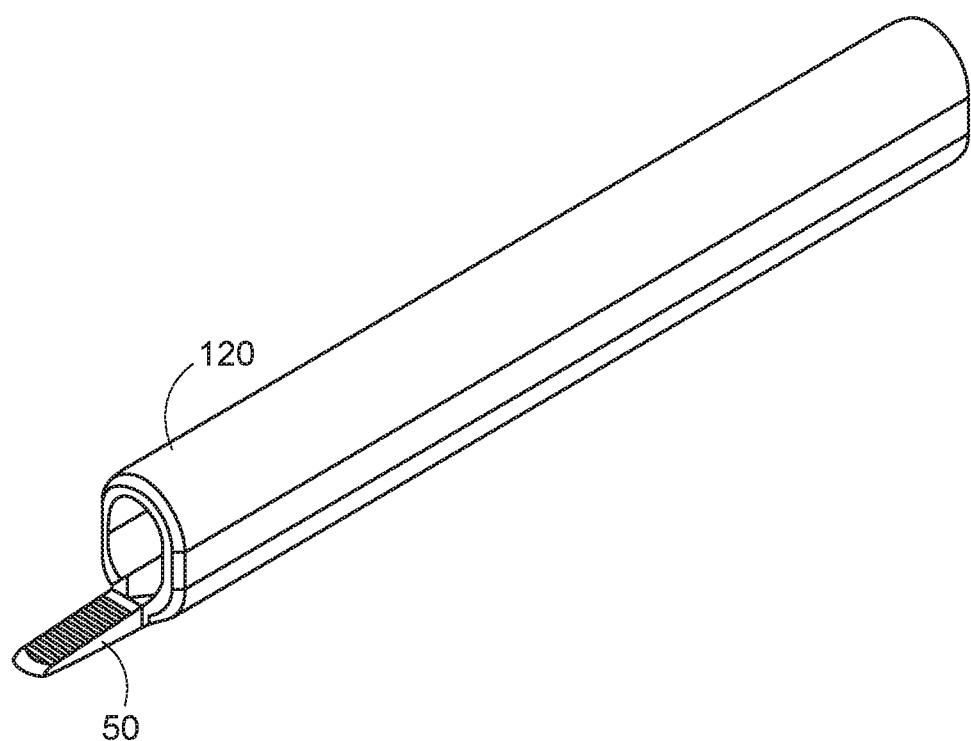
FIGS. 13A-13F are a combined access and guide system according to aspects of the present disclosure.
Figure 13B:
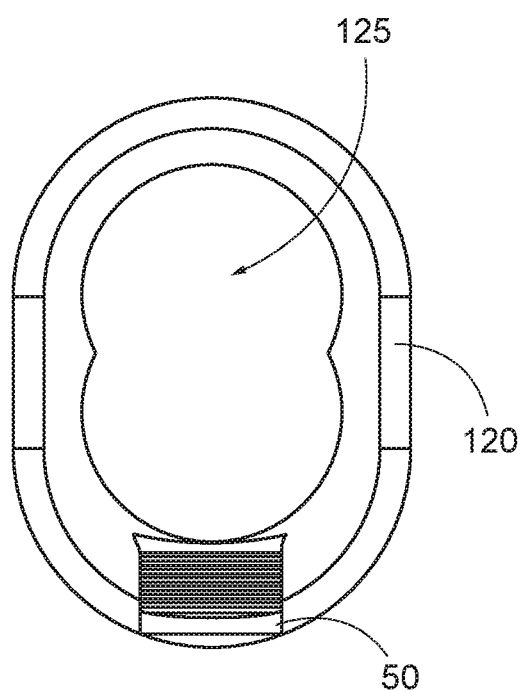
Figure 13C:
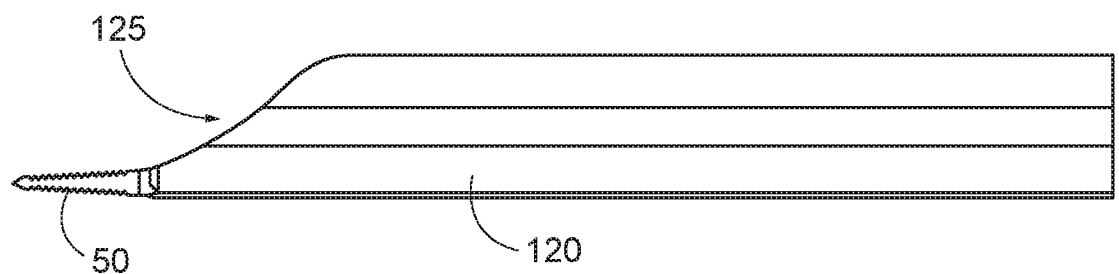
Figure 13D:
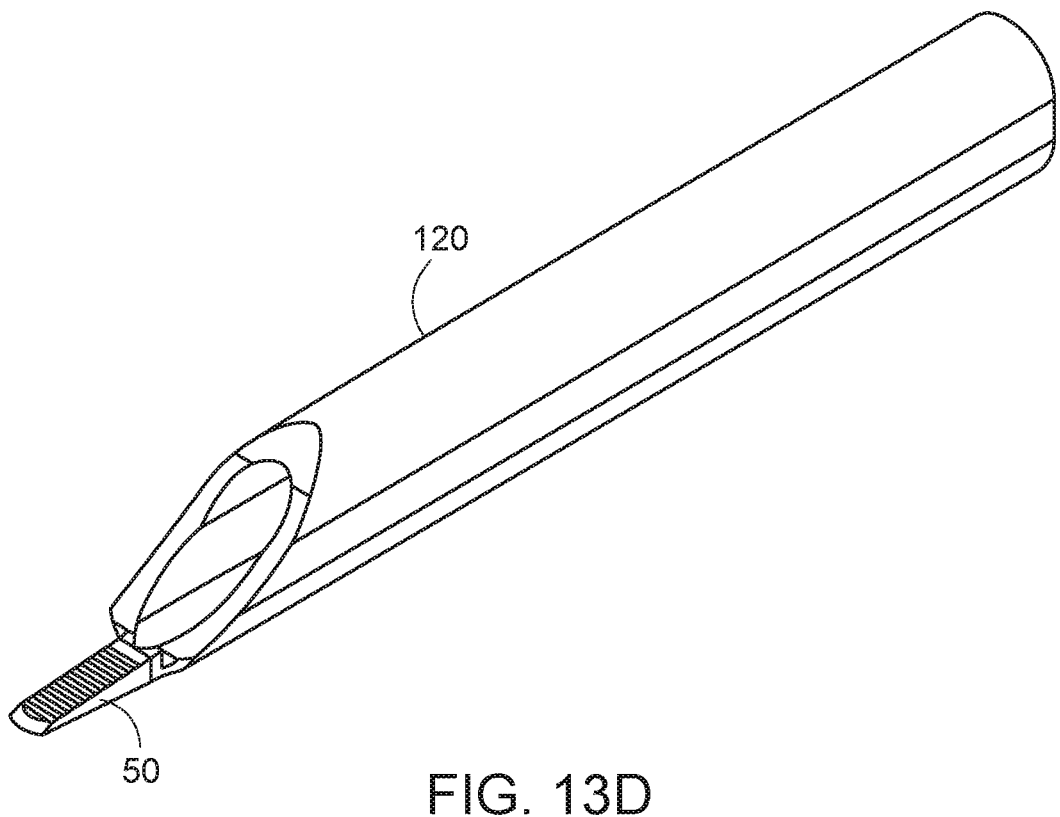
Figure 13E:
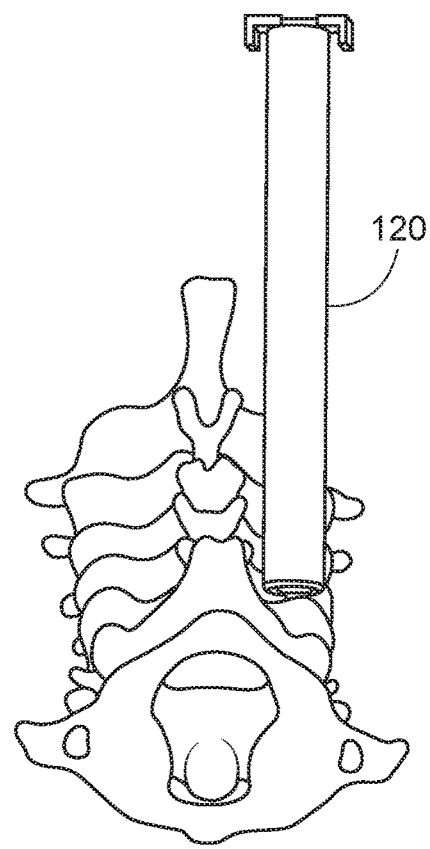
Figure 13F:
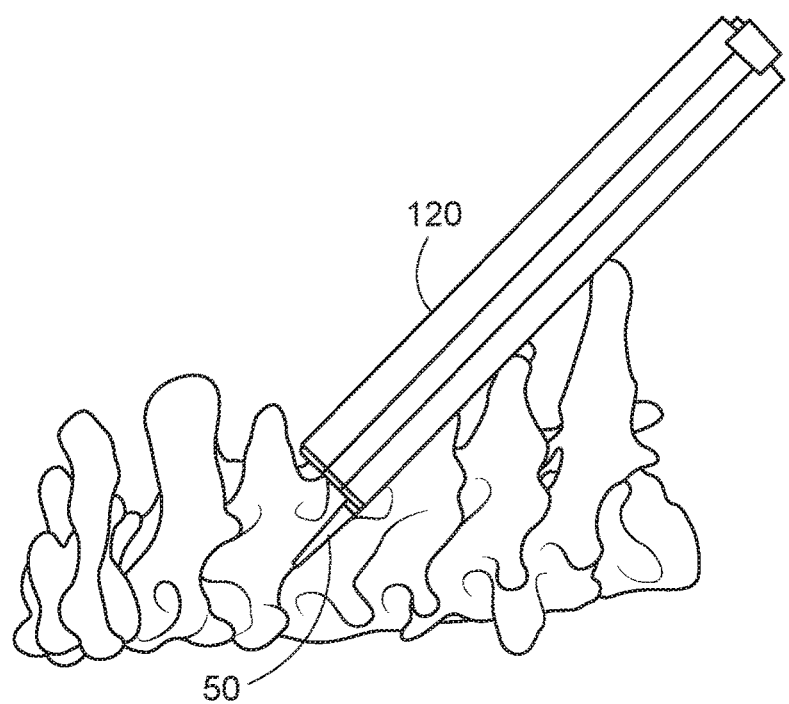

As shown in FIGS. 13A-13F, in some aspects, the access device 10 or the tip 50 is combined with a guide portal as a single, integral or monolithic access and guide system. As indicated in FIGS. 13A-B, the guide portal 120 comprises an elongated tubular body defining at least one lumen 125 therethrough. In some aspects, there may be more than one lumen or there may be partial lumen. FIGS. 13C-D illustrate another embodiment of the access and guide system the guide portal 120 comprises an elongated tubular body defining at least one lumen 125 therethrough. The tip 50 and the facet engaging face of the guide portal 120 are tapered to aid in insertion and access to the facet space. In use, and as shown in FIGS. 13E-F, the access and guide system is inserted into the facet space. The tip 50 imbeds and fixates the portal 120 to the angle of the facet. After insertion, other instruments in the system, such as a spinal fixation device, pass through the portal to the lateral mass at the same angle as the facet. While FIGS. 13E-F show insertion of the embodiment shown in FIG. 13A-B, it is understood that the embodiment of FIGS. 13C-D may be similarly inserted.

As illustrated in FIGS. 14A-19Q, in some embodiments, an access device 10 is keyed or paired to a guide device 130 as components of an access and delivery system. The guide device may be used to guide a spinal fixation device to the spine.

Figures 14K, 14L:
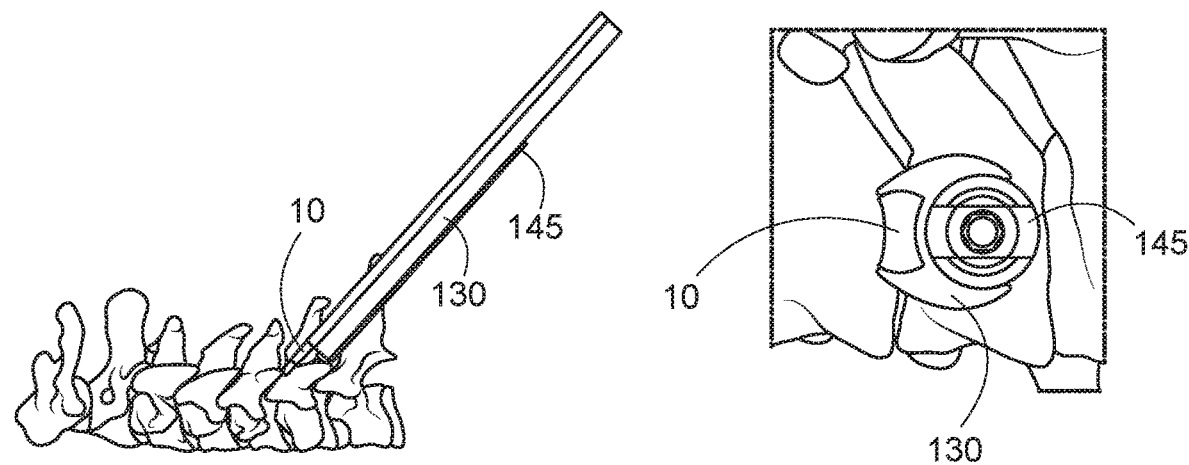
Figure 14M:
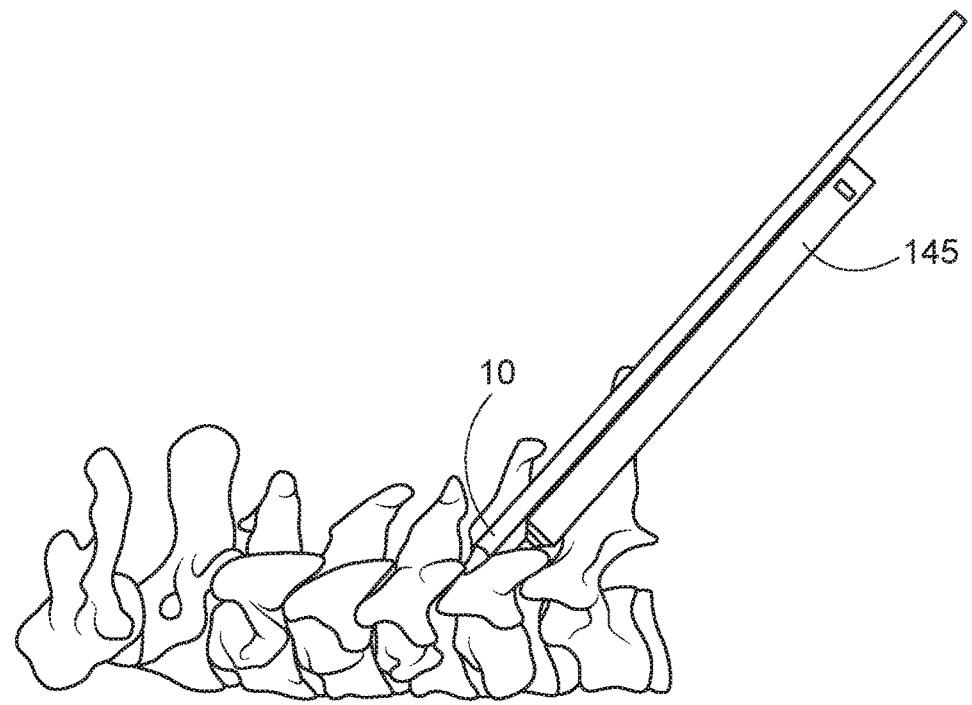
Figures 14N, 14O:
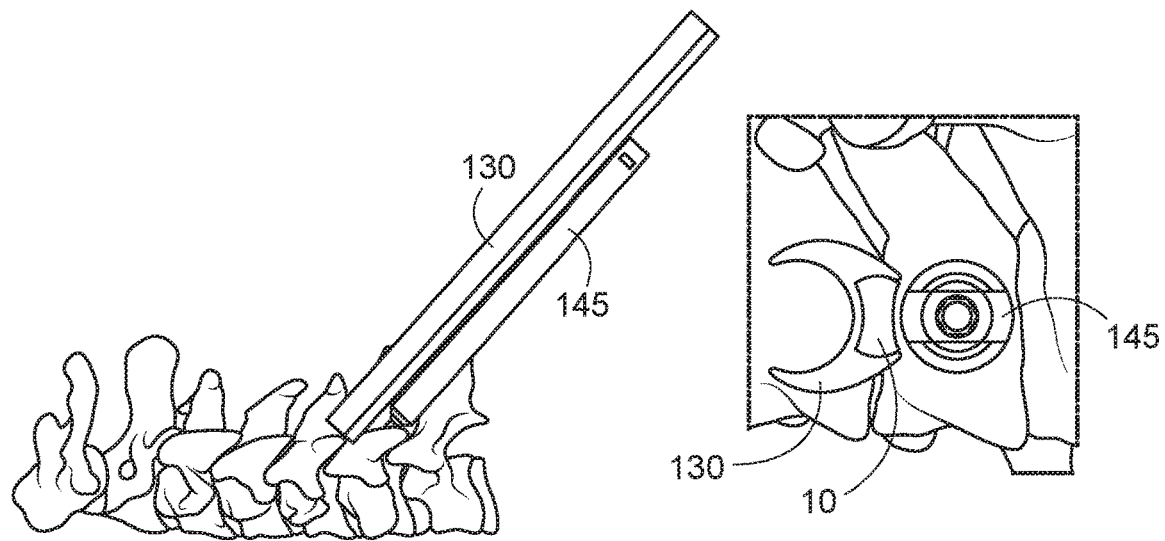
Figures 14P, 14Q:
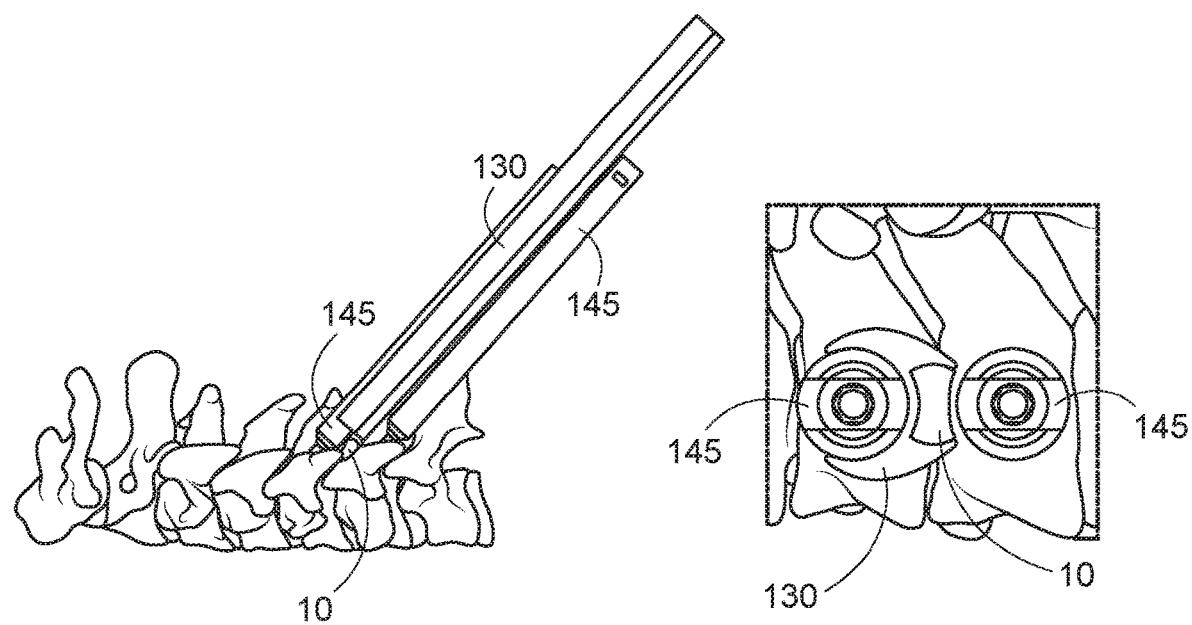
Figure 14R:
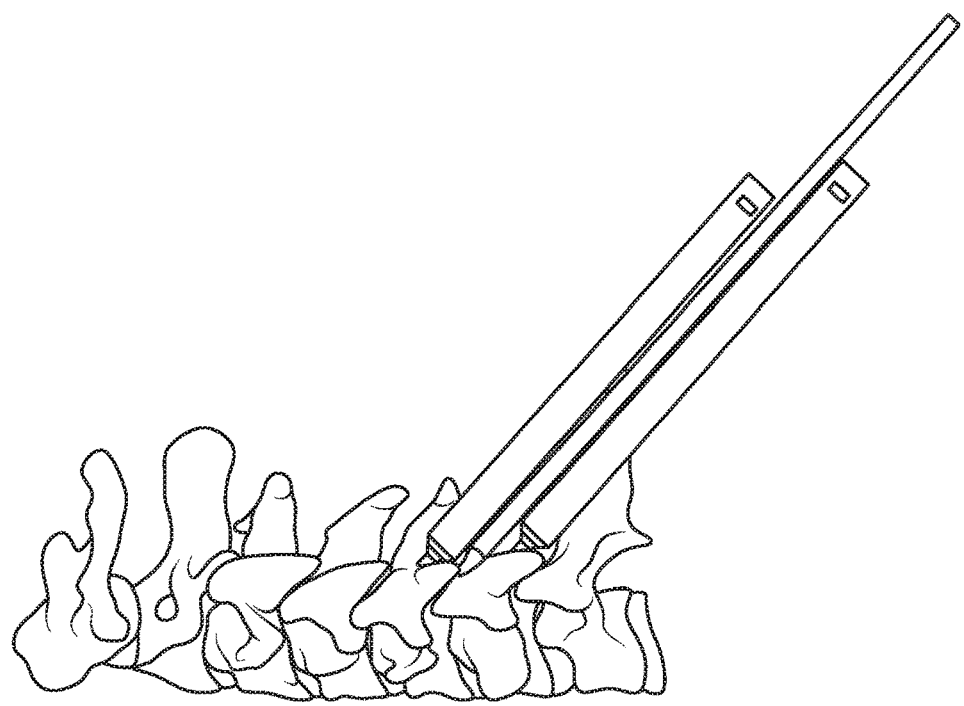
Figure 14S:
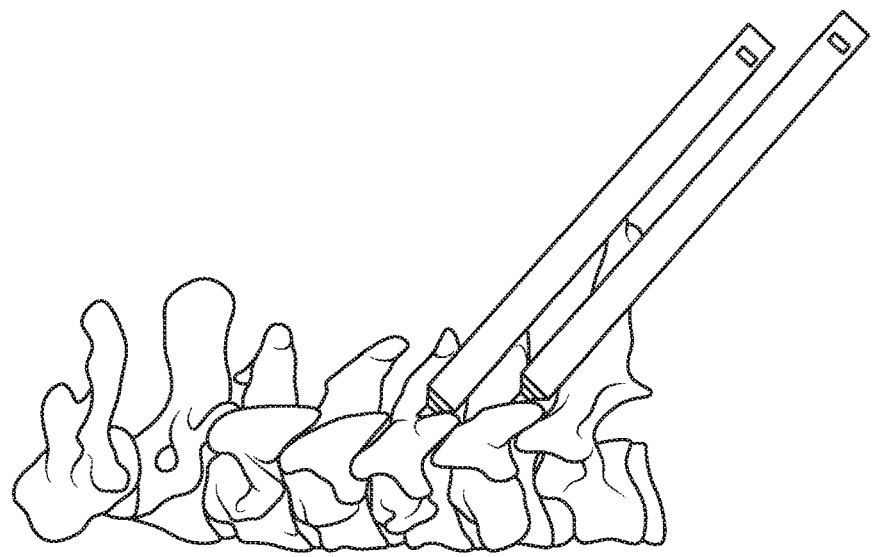

As shown in the perspective and cross section views of FIGS. 14A-D, in one embodiment, the guide device 130 includes a plurality of slots or openings 135, an upper or first slot configured to receive and guide a tower or screw component of the spinal fixation device (see more description below) and a lower or second slot configured to engage the access device 10. The access device 10 includes first (or upper) and second (or lower) notches or recesses 140 complementary to and keyed to the guide device. FIGS. 14E-G illustrate the access device 10 and guide device 130 positioned together and FIGS. 14H-J illustrate the access device 10 inserted into the facet joint and then the guide device inserted over the guide device. FIGS. 14K-14S depicts use of the access device 10 and guide device 130 to deliver one or more spinal fixation devices 145. In use, the access device 10 inserted into the facet joint and then the guide device inserted over the access device. The spinal fixation device 145 is inserted through the guide 130 and the bone screw is screwed into the lateral mass (FIGS. 14K-L). The guide 130 is removed (FIG. 14M) but the access device 10 remains in place. The guide is then placed on the other side of the access device to engage the other lateral mass. (FIGS. 14N-O). The spinal fixation device 145 is inserted through the guide 130 and the bone screw is screwed into the lateral mass. (FIGS. 14P-Q). The guide device and the access device are then removed (FIGS. 14R-S) and a rod may be inserted in the towers of the fixation devices (not shown, but see below).

Figure 15A:
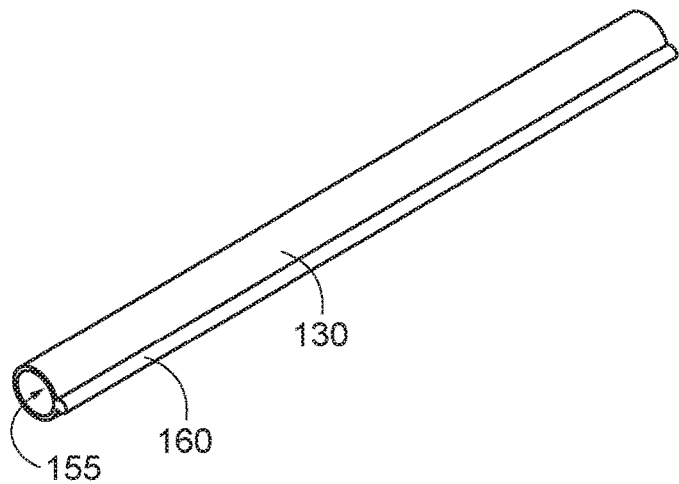
FIGS. 15A-15G illustrate an access and delivery system according to aspects of the present disclosure.
Figure 15B:
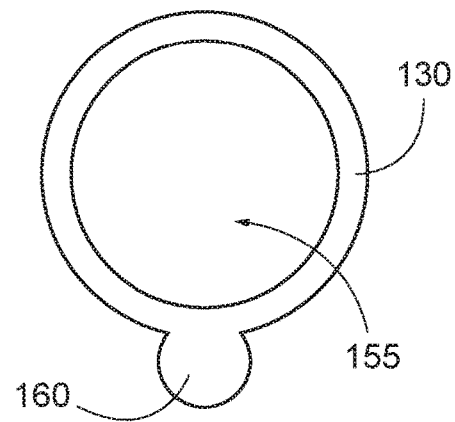
Figure 15C:
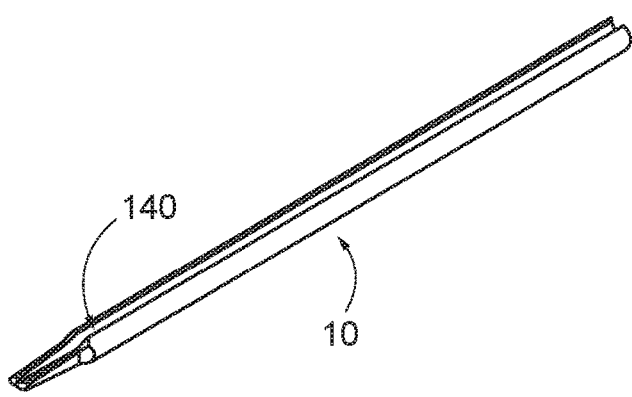
Figure 15D:
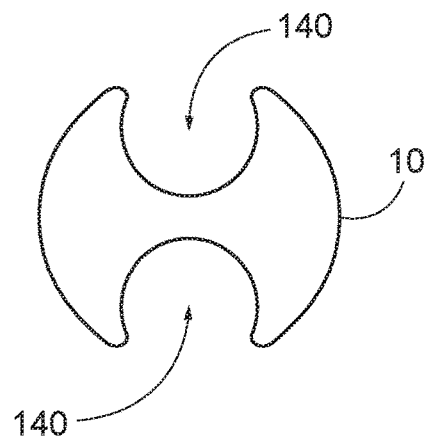
Figure 15E:
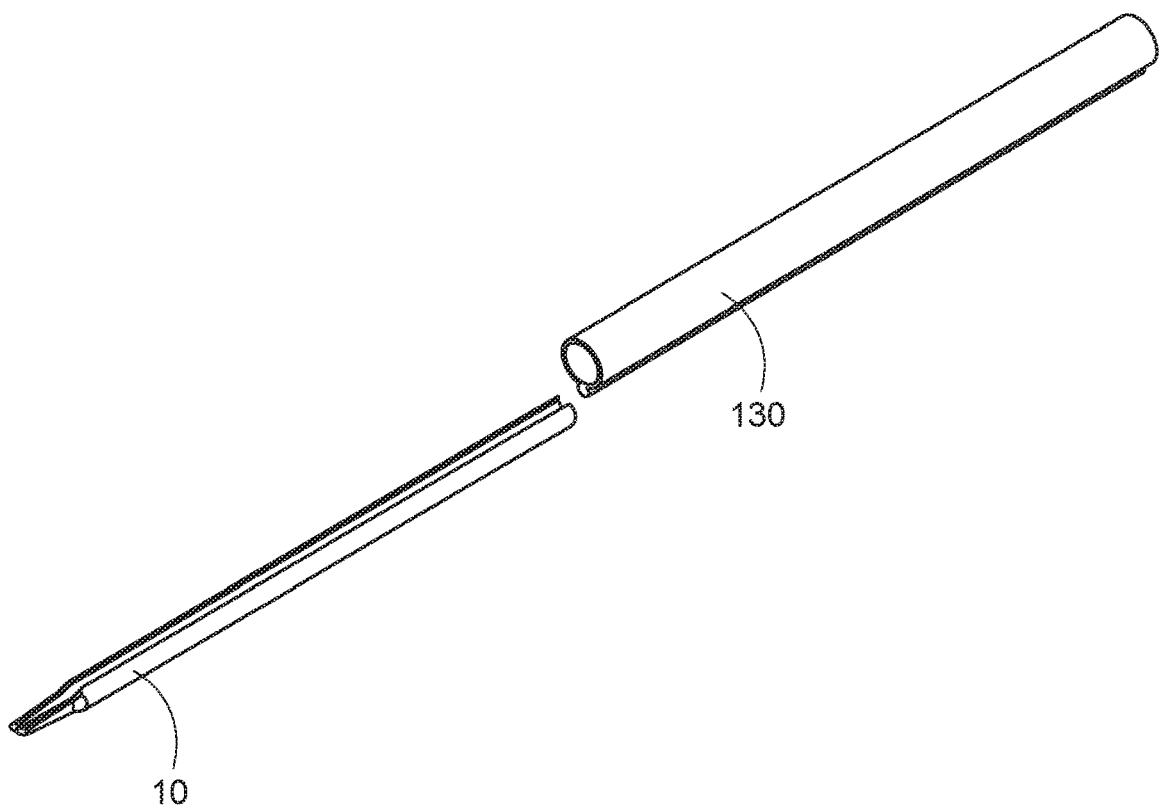
Figures 15F, 15G:
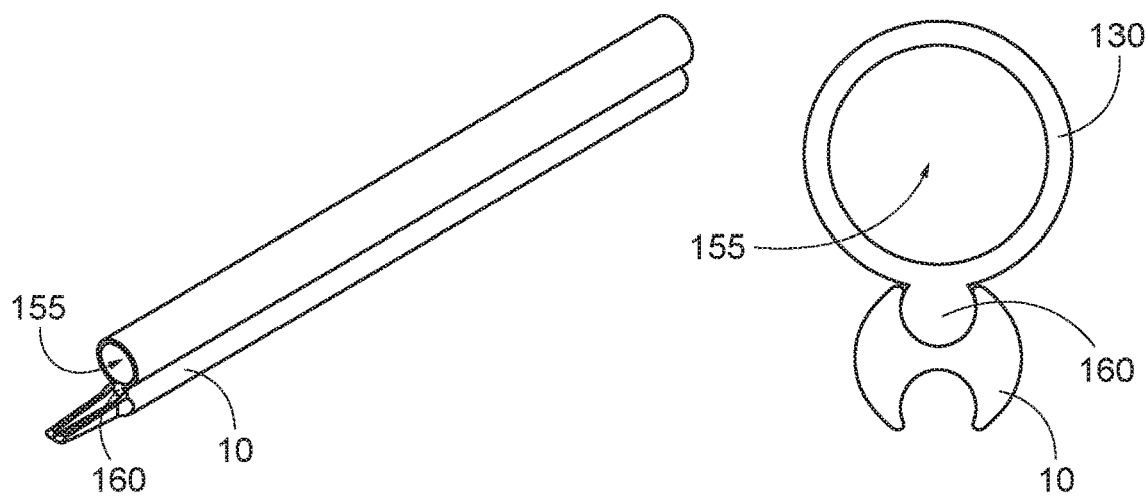
Figure 15H:
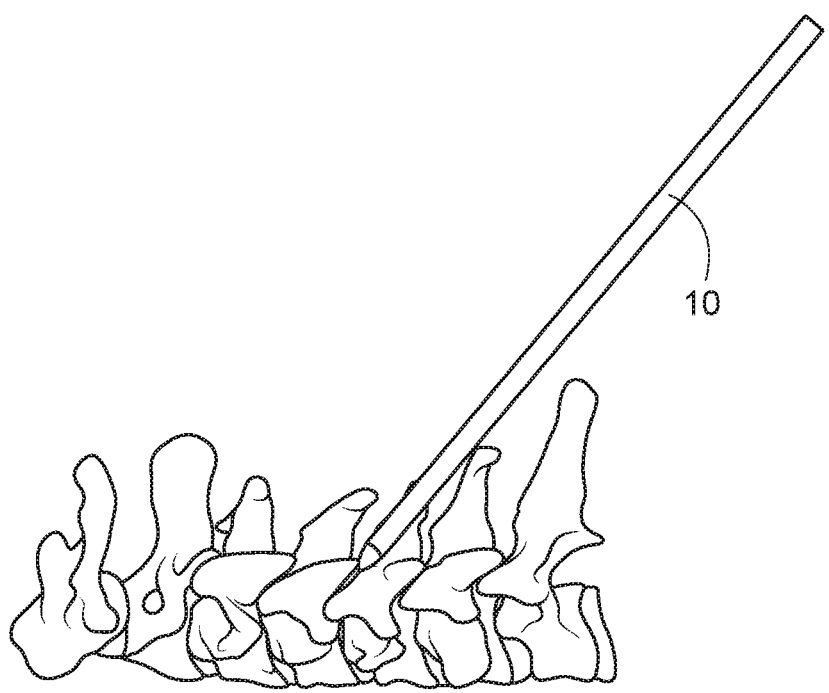
FIGS. 15H-15R illustrate the system of FIGS. 15A-15G in use.
Figure 15I:
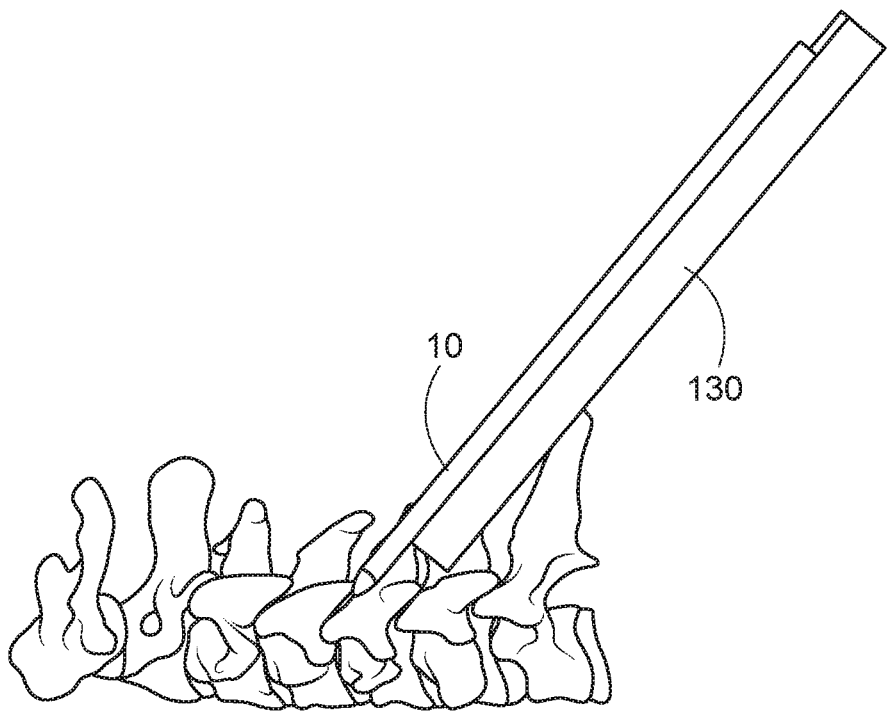
Figure 15J:
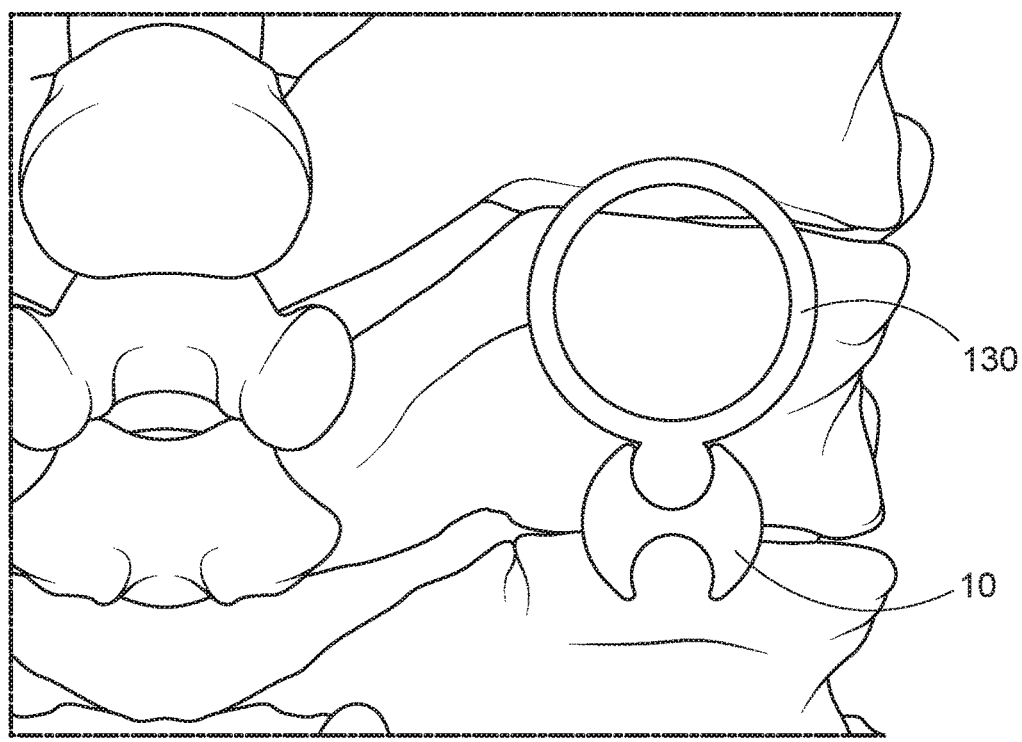
Figure 15K:
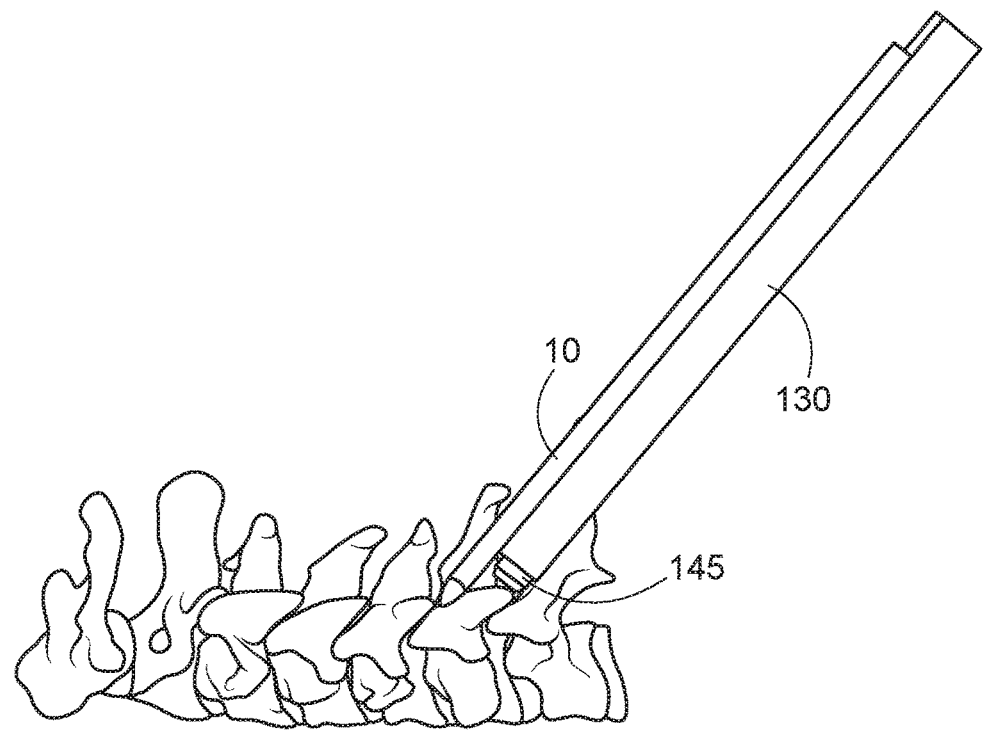
Figure 15L:
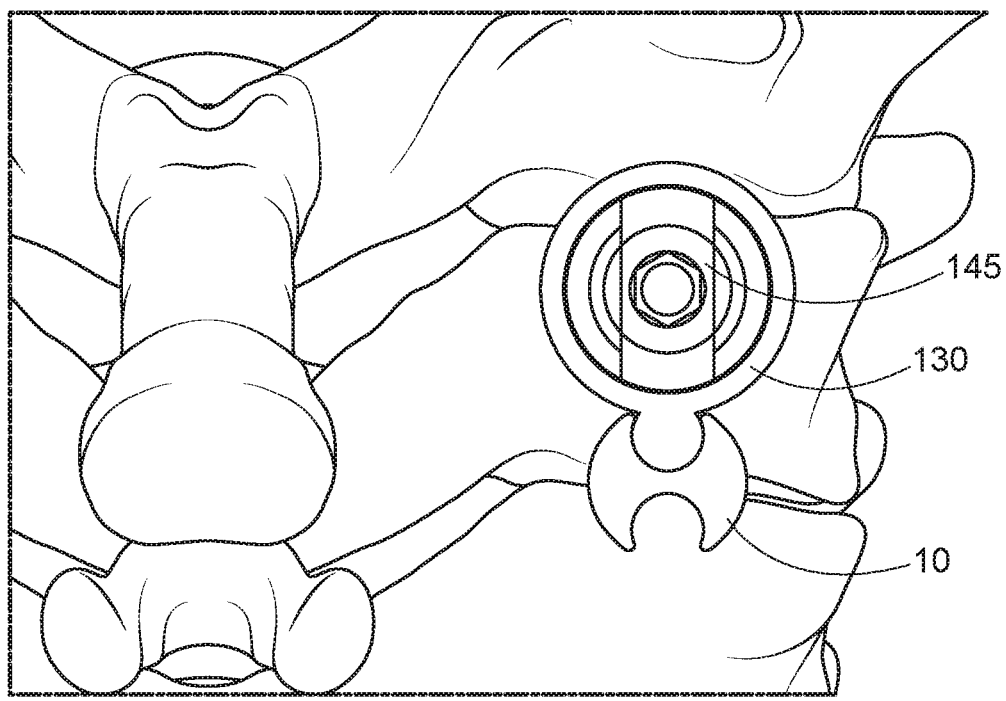
Figure 15M:
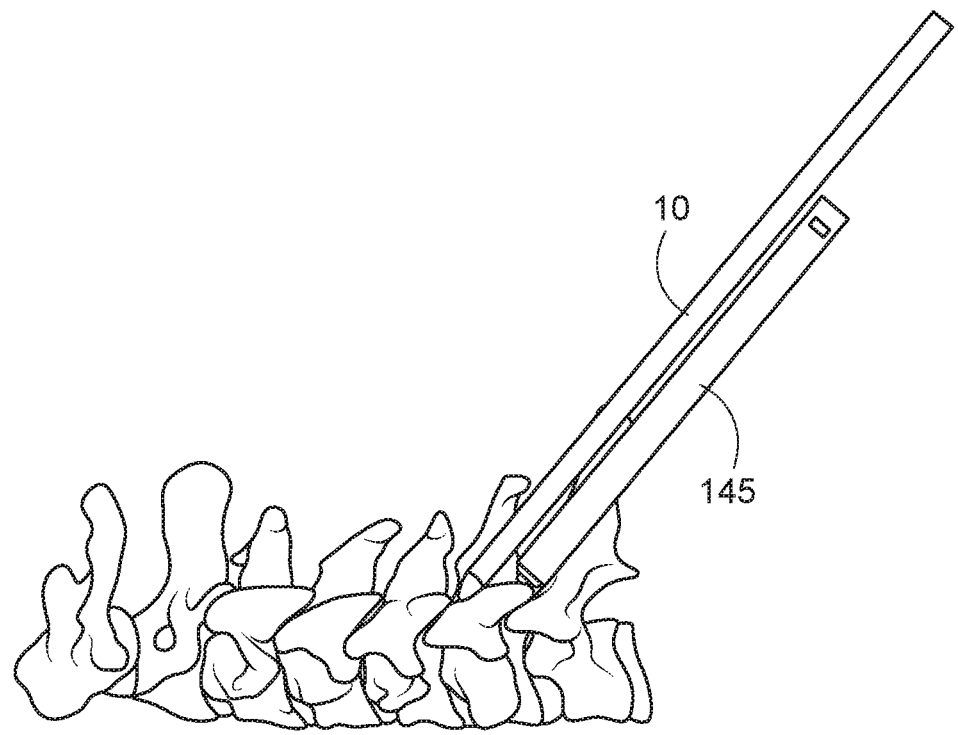
Figure 15N:
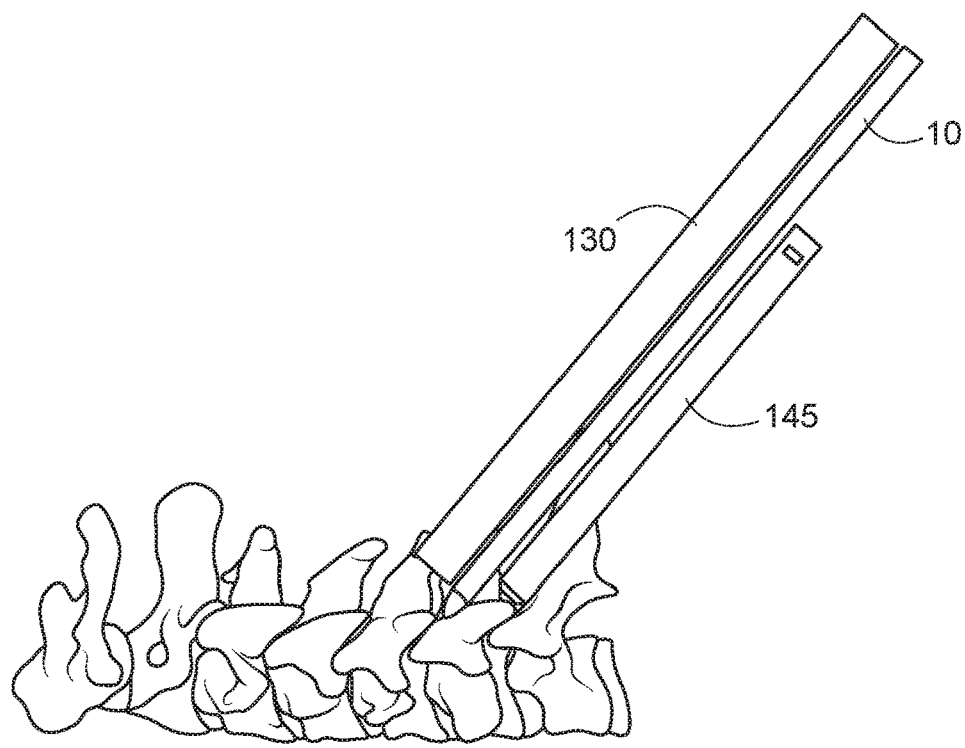
Figure 15O:
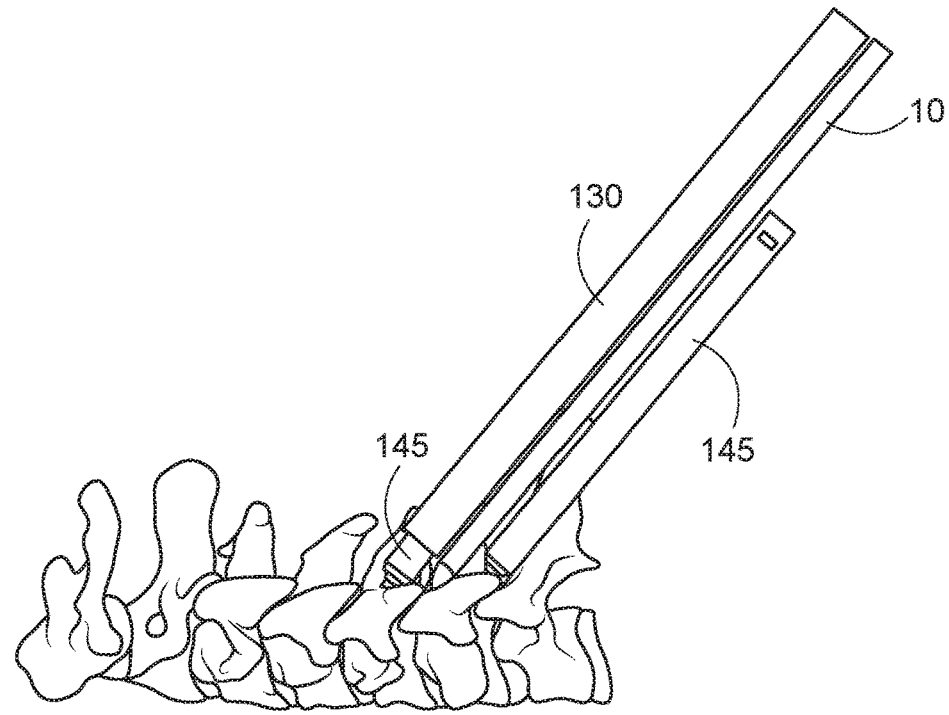
Figure 15P:
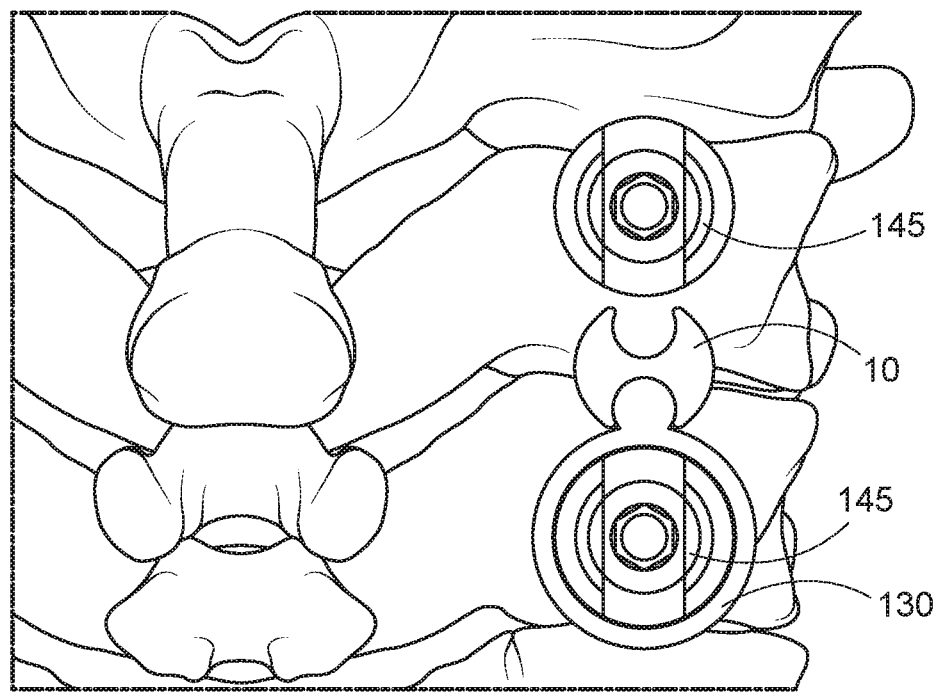
Figure 15Q:
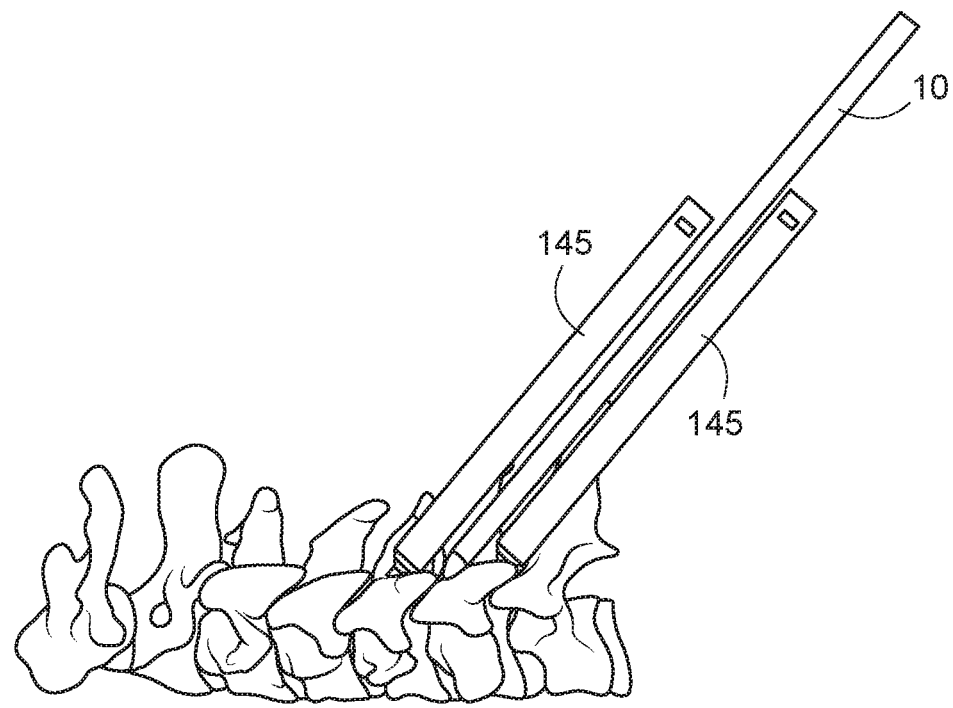
Figure 15R:
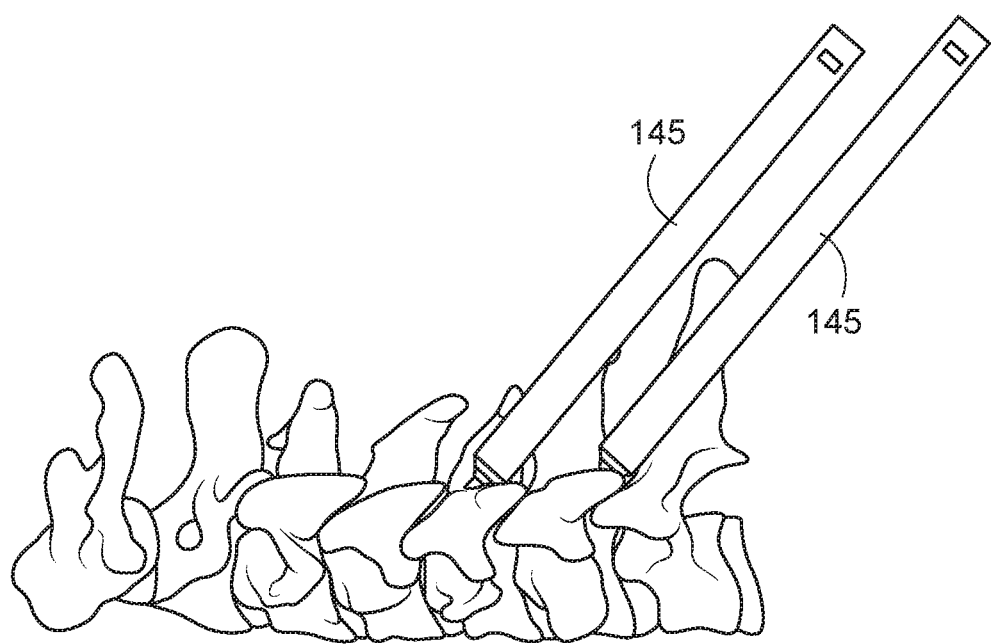

As shown in the perspective and cross section views of FIGS. 15A-D, in one embodiment, the guide device 130 includes a lumen 155 defined therethrough and configured to receive and guide a tower or screw component of the spinal fixation device (see more description below) and a rail mating feature 160 configured to engage the access device 10. The access device 10 includes first (or upper) and second (or lower) notches or recesses 140 complementary to and keyed to the guide device. FIGS. 15E-G illustrate the access device 10 and guide device 130 positioned together and FIGS. 15H-J illustrate the access device 10 inserted into the facet joint and then the guide device inserted alongside the guide device. FIGS. 15K-15R depicts use of the access device 10 and guide device 130 to deliver one or more spinal fixation devices 145. In use, the access device 10 inserted into the facet joint and then the guide device inserted alongside the guide device. The spinal fixation device 145 is inserted through the guide 130 and the bone screw is screwed into the lateral mass (FIGS. 15K-L). The guide 130 is removed (FIG. 15M) but the access device 10 remains in place. The guide is then placed on the other side of the access device to engage the other lateral mass. (FIGS. 15N-0). The spinal fixation device 145 is inserted through the guide 130 and the bone screw is screwed into the lateral mass. (FIGS. 15P-Q). The guide device and the access device are then removed (FIG. 15R) and a rod may be inserted in the towers of the fixation devices (not shown, but see below).

In some aspects, guide device 130 may be used with only a portion of the access device 10, such as the tip 50 and may be further stabilized by engagement with a fixation device, such as a tower or a polyaxial screw with a tower feature, that is already implanted.

Figure 16A:
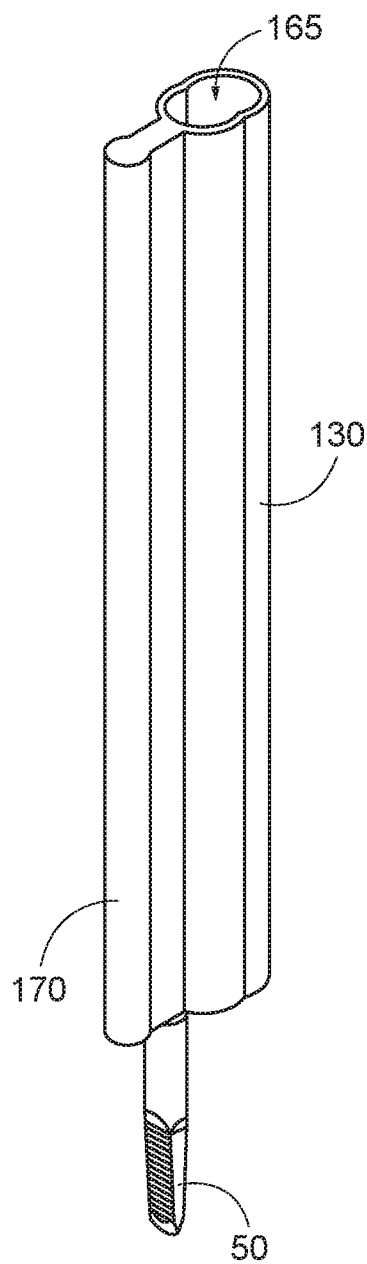
FIGS. 16A-16C illustrate an access and delivery system according to aspects of the present disclosure which may be further stabilized by engagement with a fixation device.
Figure 16B:
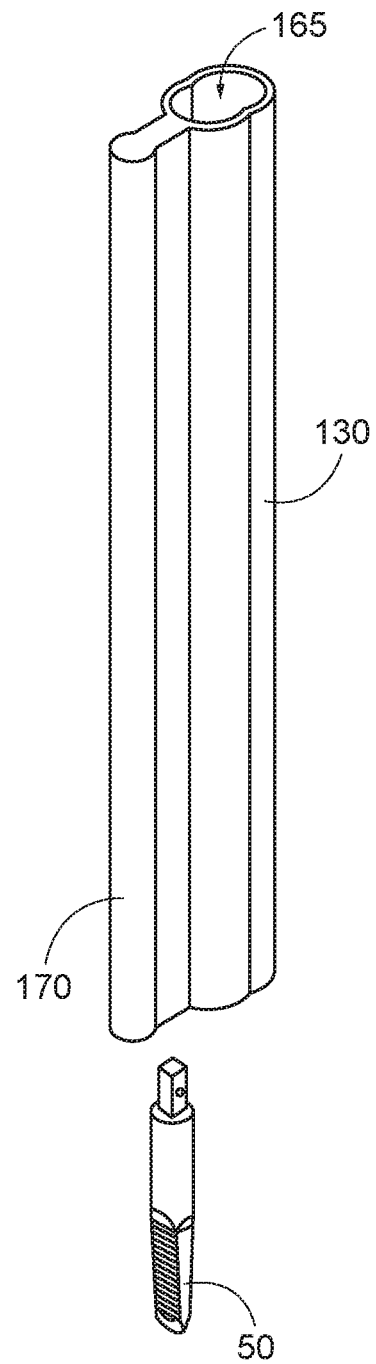
Figure 16C:
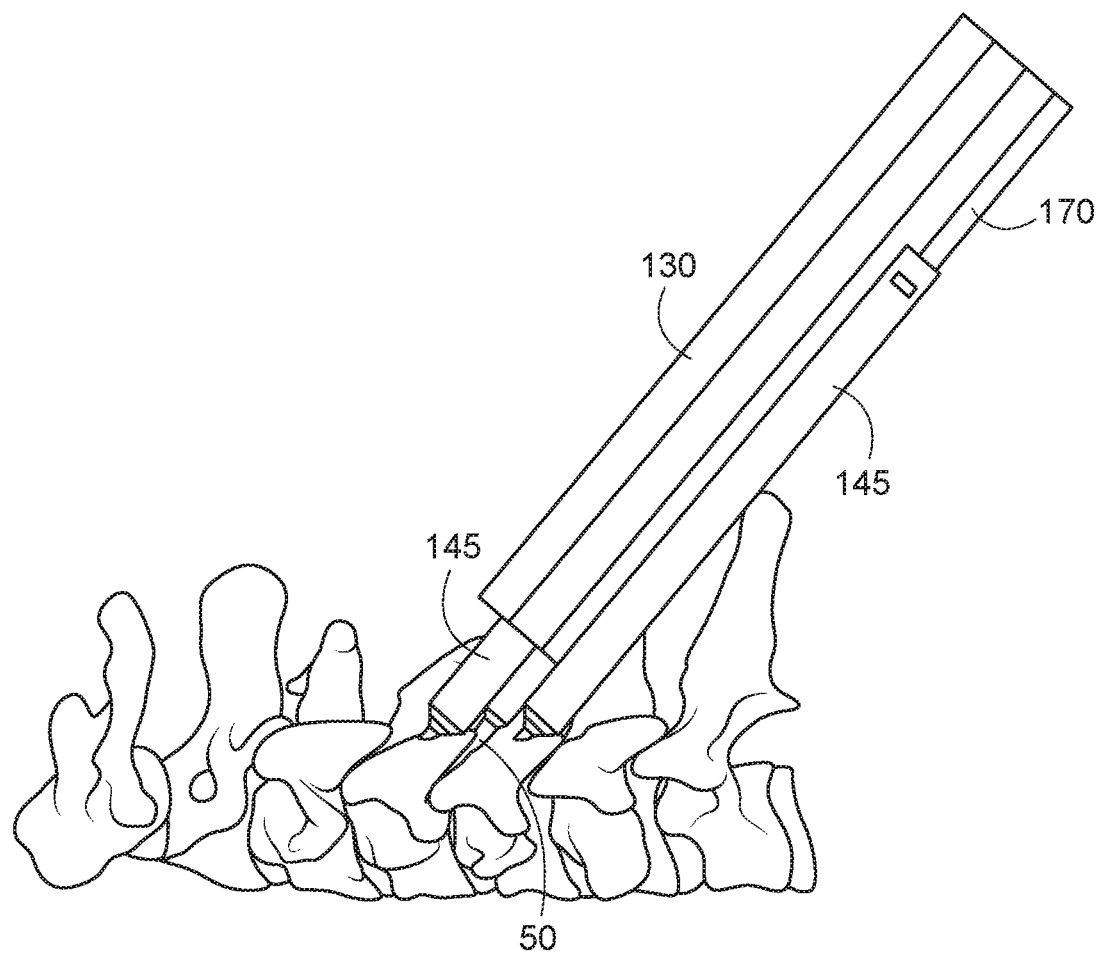

For example, and as shown in FIGS. 16A-B, guide device 130 includes a lumen 165 defined therethrough and a screw tower engagement feature 170. The engagement feature may be a generally cylindrical body protruding from an outer surface of the guide device and generally extending the length of the guide device. The lumen 165 may have the shape of a number eight or other dual positioning shape. FIG. 16C illustrates use of the guide device 130 and access device tip 50 to place towers of the fixation devices, as described in more detail below.

FIGS. 17A-17F illustrate another embodiment of the guide device 130 that may be further stabilized by engagement with a fixation device, such as a tower, that is already implanted. As shown in FIGS. 17A-B, guide device 130 includes a lumen 165 defined therethrough and a tower engagement feature 170. The engagement feature may be a generally cylindrical body protruding from an outer surface of the guide device and generally extending the length of the guide device. The lumen 165 may have the shape of a number eight or other dual positioning shape (indicated by positions 1 and 2). In use (spine is hidden for clarity), and as shown in FIGS. 17C-17F, the guide device 130 is inserted into an anchored tower 145. Then, the second tower 145 is inserted through the lumen 165 into either position 1 or position 2.

FIGS. 18A-H illustrate cross sections of other embodiments of the guide device 130 including a lumen 165 defined therethrough and a tower engagement feature 170. The tower engagement feature may be configured to be received by the tower (FIGS. 18A-D) or may be configured to receive the tower (FIGS. 18E-18H).

Figures 19G, 19H:
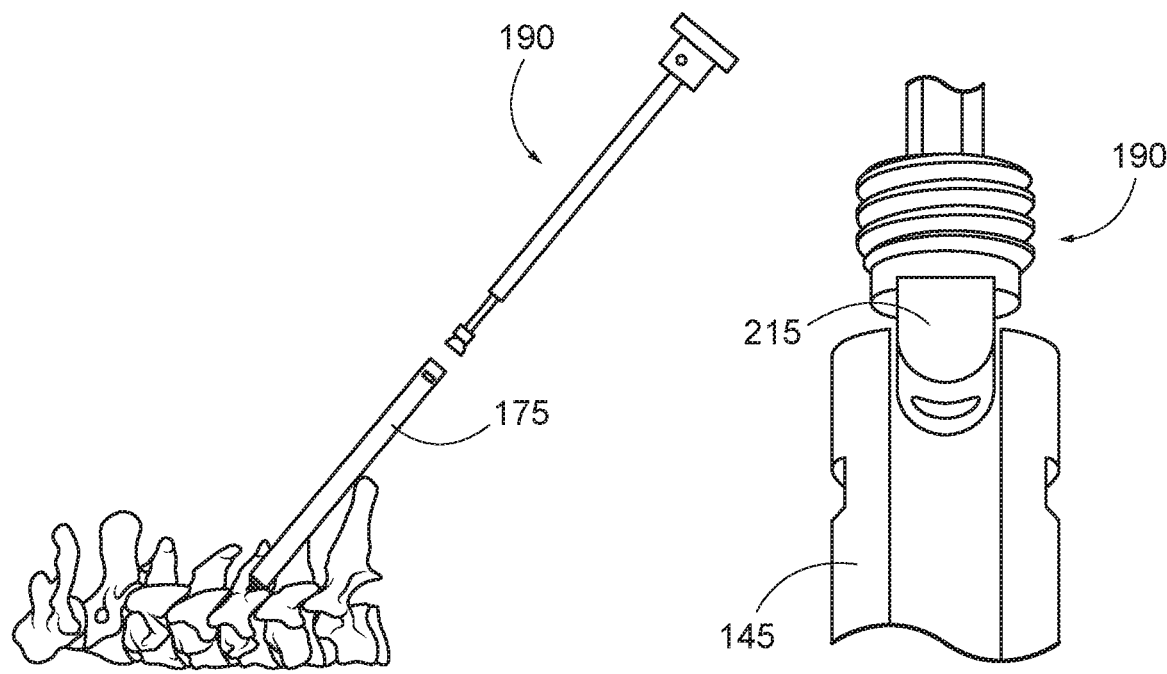
Figures 19I, 19J:
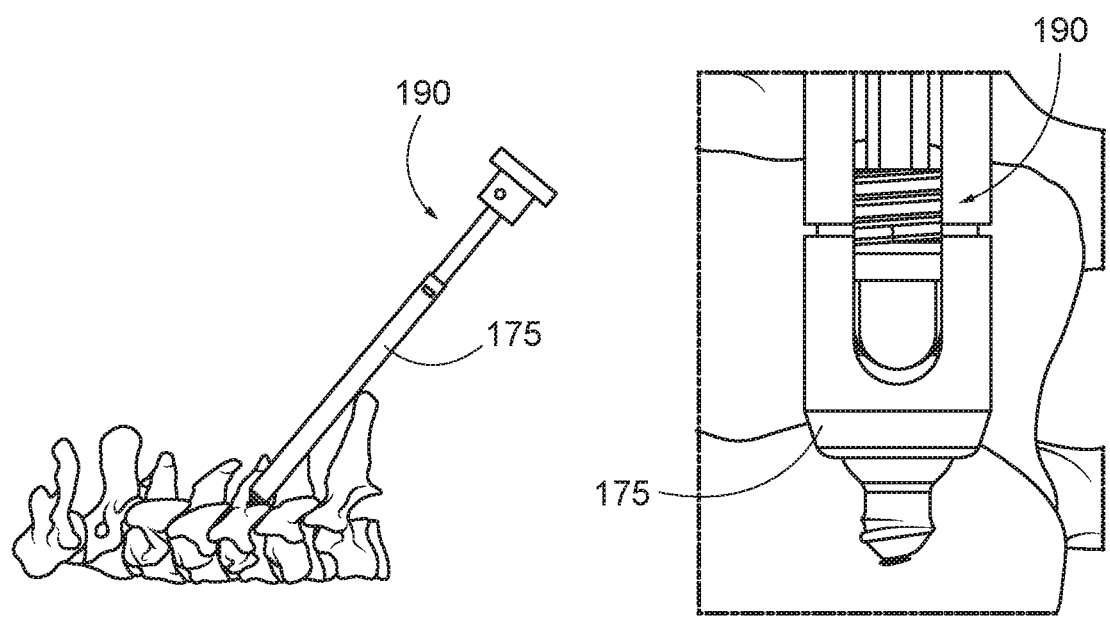

FIGS. 19A-19B depict a temporary locking screw that may be used with the system of FIG. 17. The locking screw 190 includes a hex head 195, external threads 200 that match internal tower threading, a securing pin hole 205, a securing pin 210, a rotating head 215, which may be 3.5 mm, and a pin 220 that allows the head to rotate about the shaft. In use, and as illustrated in FIGS. 19C-19E, the screw 190 is inserted into the tower (19C), and the threading 200 engages with the internal tower threading (19D). The screw head 195 abuts the saddle to lock rotation of the tower with respect to the screw (19E). The tower will not rotate if the screw remains tightened.

Figures 19K, 19L:
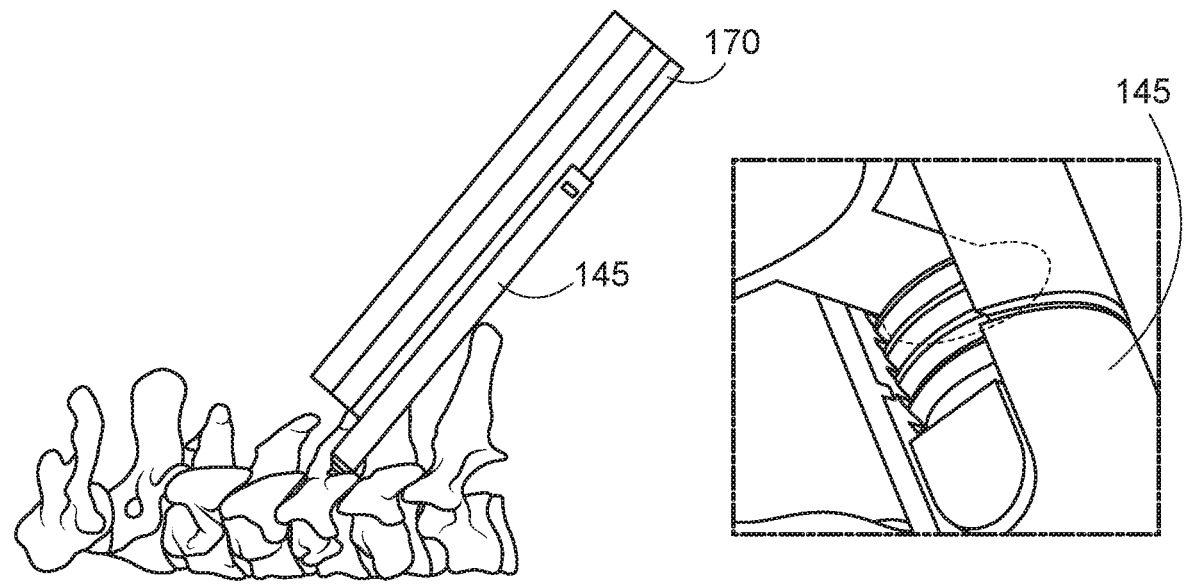
Figures 19M, 19N:
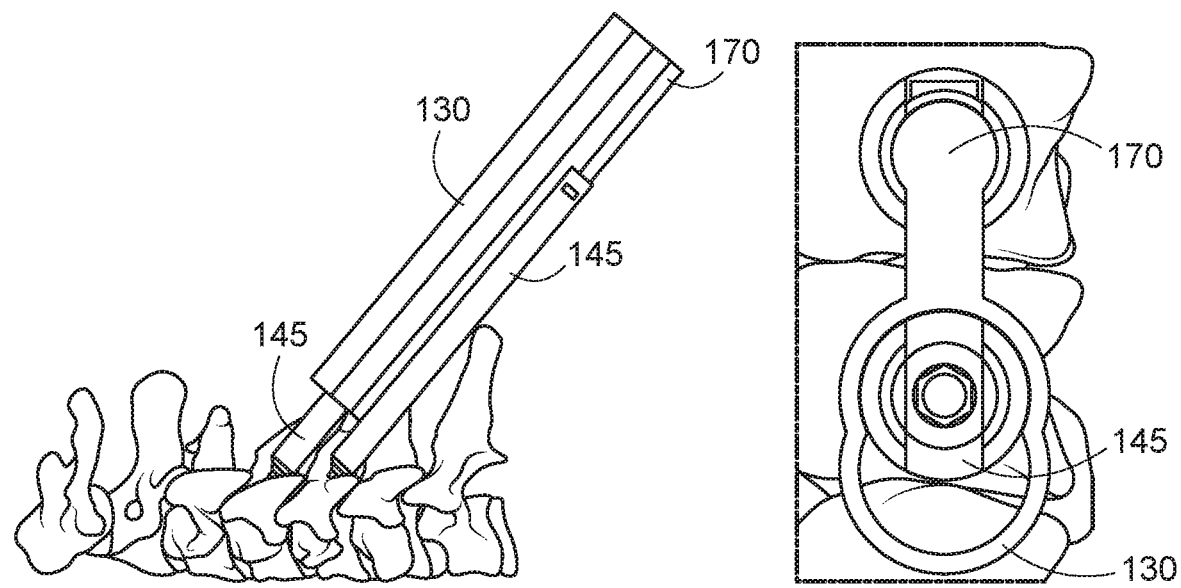
Figure 19O:
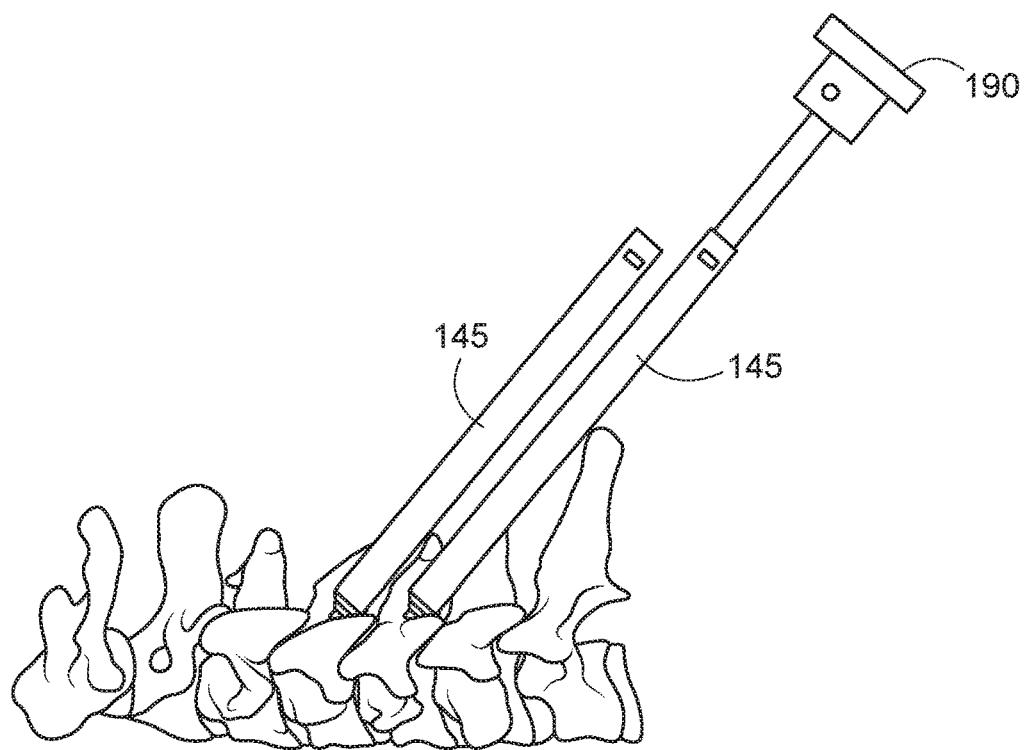
Figure 19P:
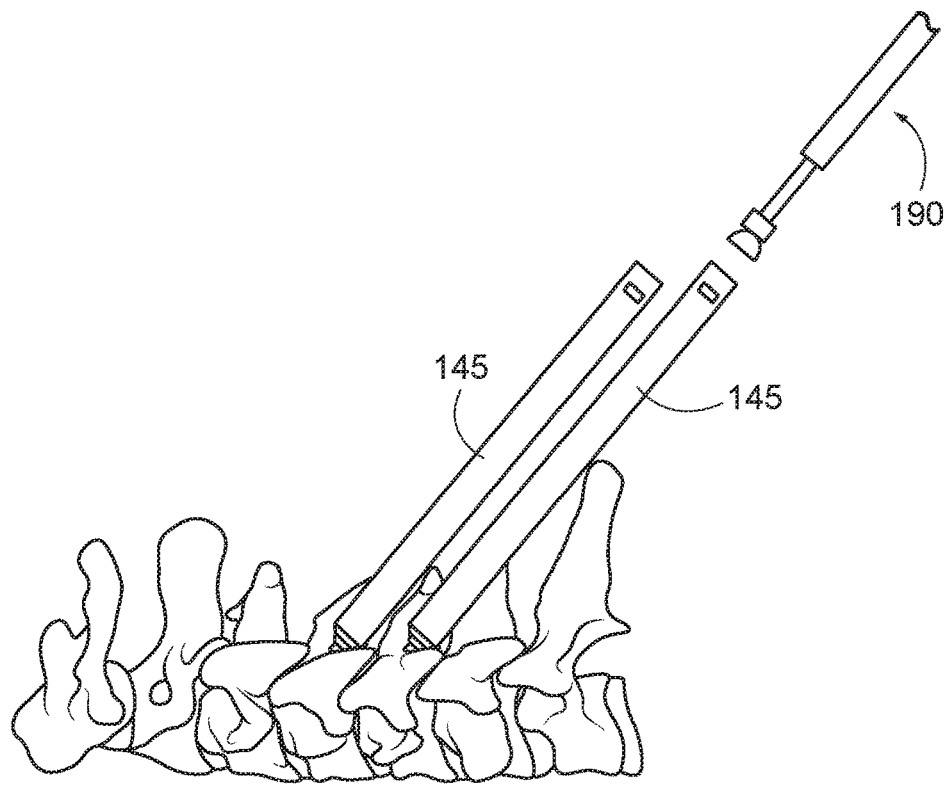
Figure 19Q:
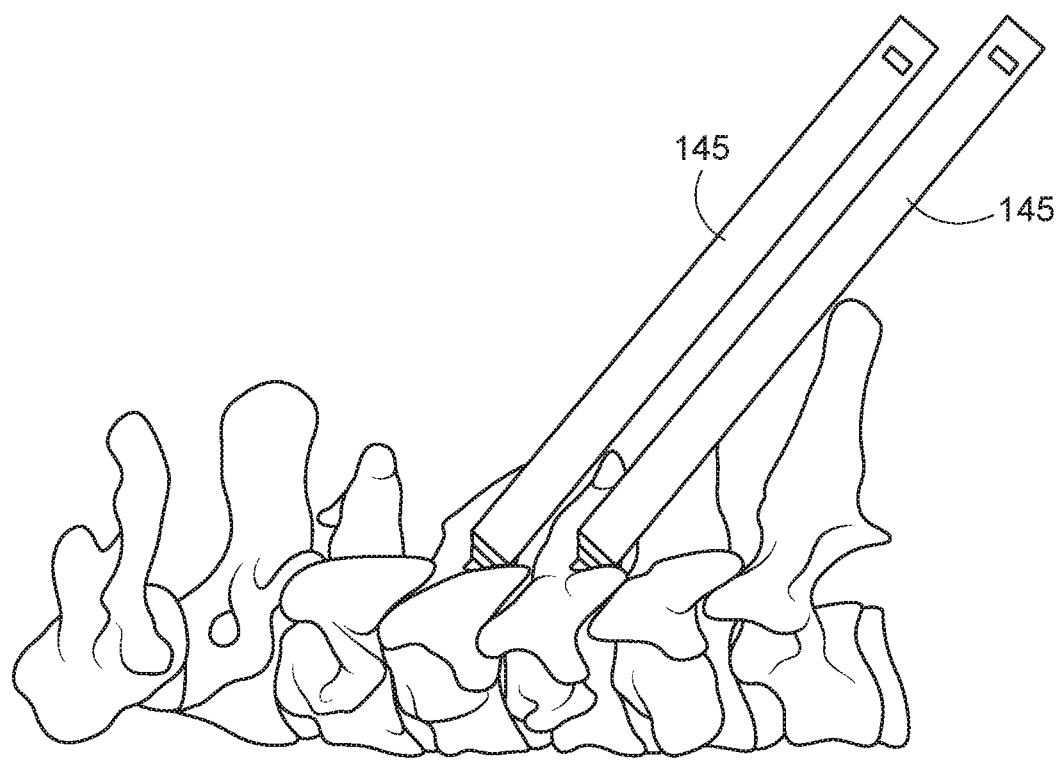

In use in the spine, the tower is screwed into the lateral mass (19F). The screw 190 is inserted into the tower 145 with a hex driver (19G). The head 215 is oriented as shown (19H). The hex driver is rotated clockwise to tighten the screw until the head contacts the saddle (19I-J). The guide device 130 is inserted onto the tower, abutting the back surface of the temporary locking screw 190 (FIGS. 19K-L). Next, the second tower is inserted through the guide tube. (19M-N). The guide is removed and the hex driver is used to unscrew the temporary locking screw (190). The locking screw is removed (19P) and the two towers are secured in the lateral mass (19Q).

In various embodiments, a fixation device 145, such as a polyaxial screw with tower feature, is used to provide additional stability to the spine following a spinal fusion procedure. The tower is an extension to a polyaxial screw, such as a pedicle screw or a lateral mass screw, that is used for minimally invasive posterior fixation systems as described herein. The tower may be a removable tower. The embodiments described above include a tower having a full length slot that permit a fixation rod to be lowered into place.

Figure 20A:
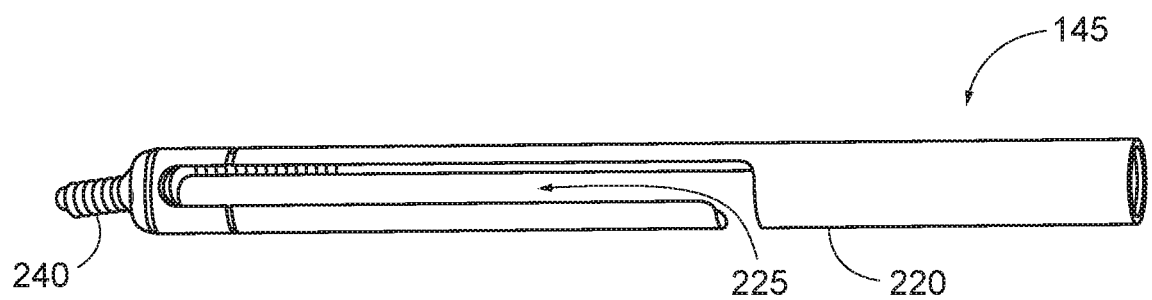
FIG. 20A is a fixation device for use with the devices and systems of the present disclosure.
Figure 20B:
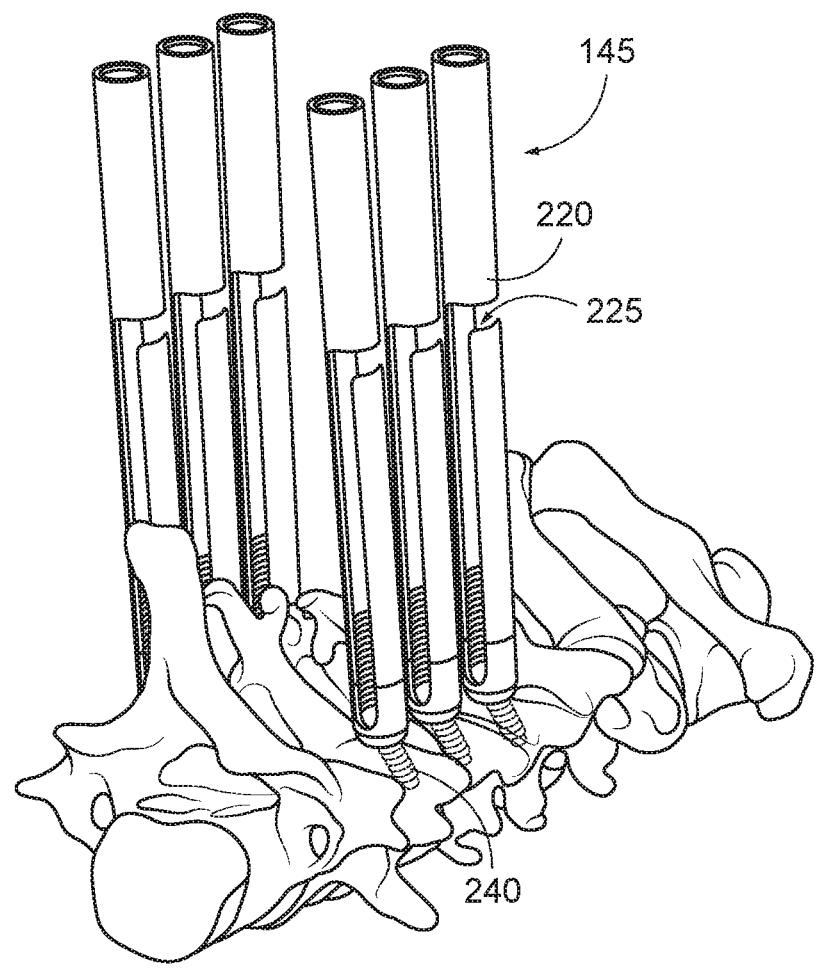
FIGS. 20B-20E show the fixation device of FIG. 20A in use.
Figure 20C:
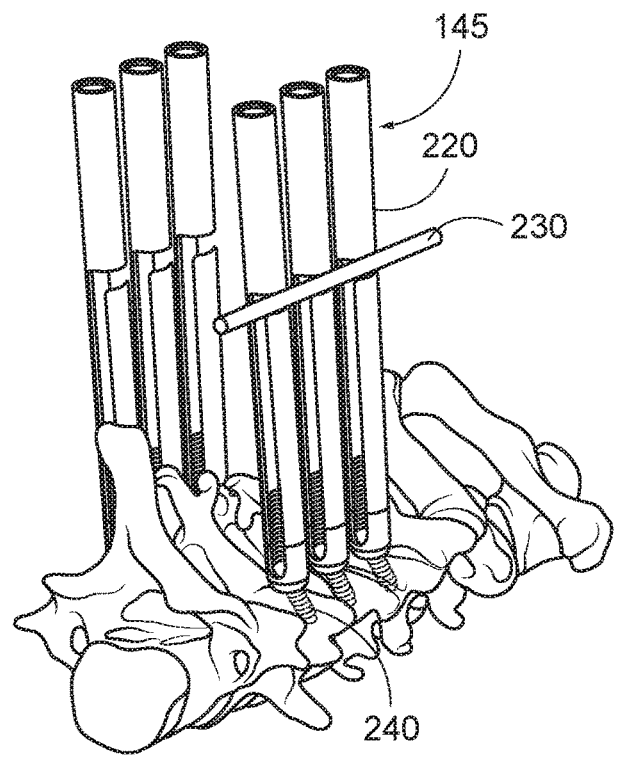
Figure 20D:
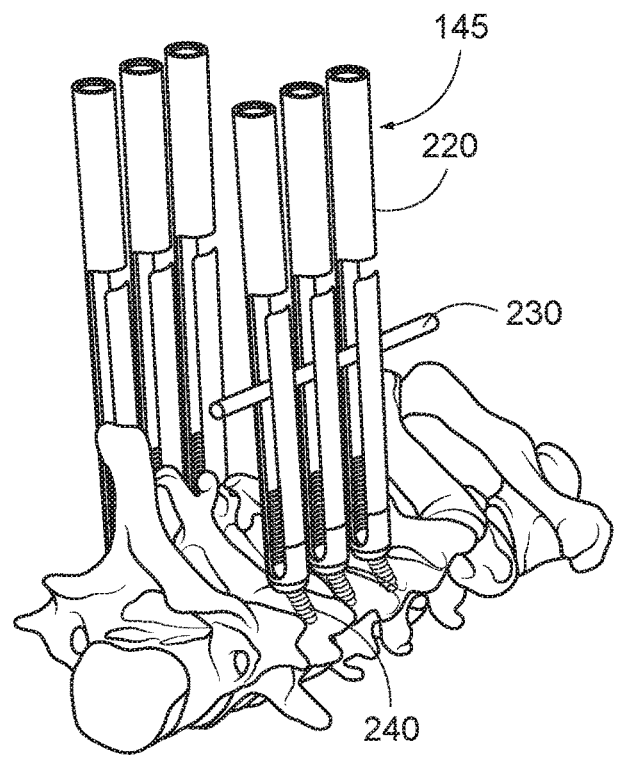
Figure 20E:
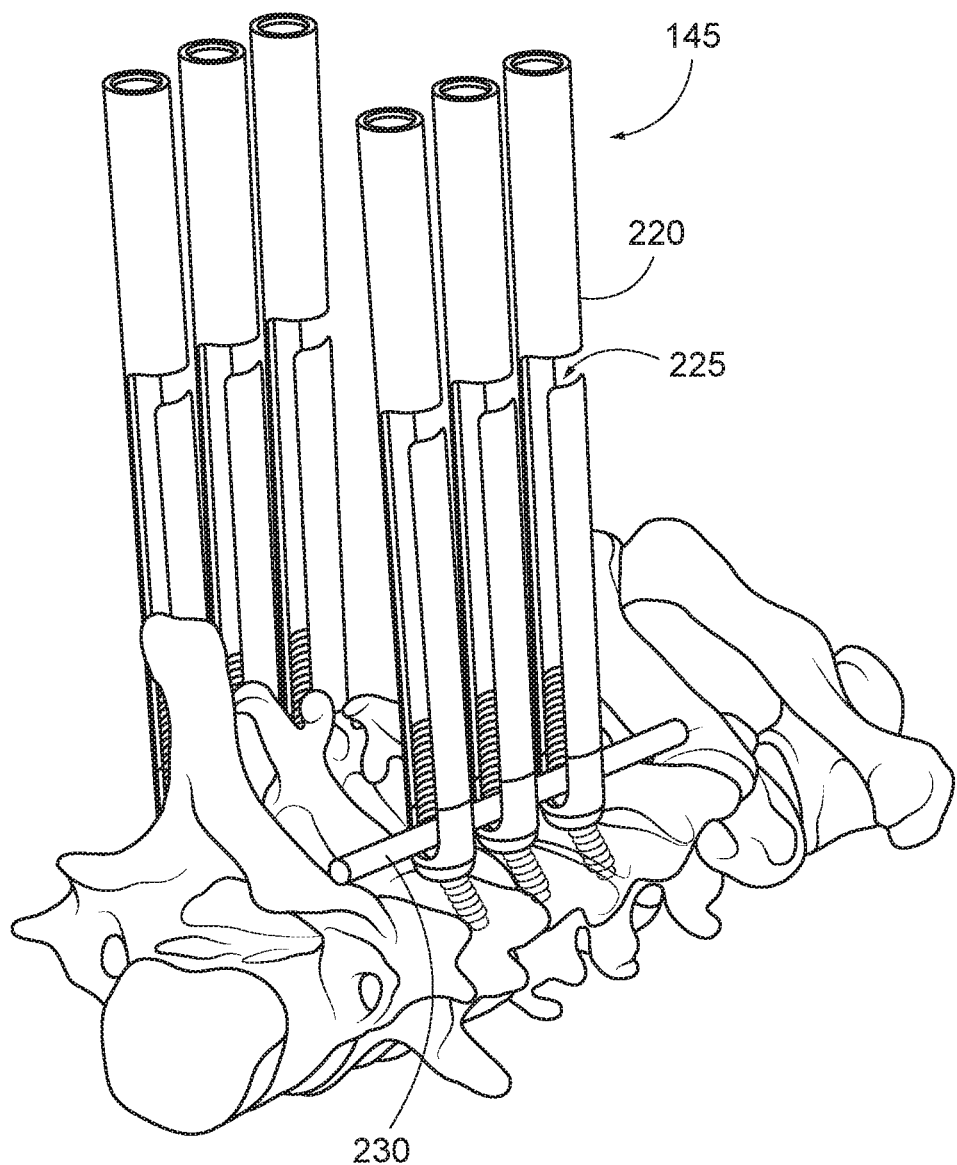

In another aspect, and as illustrated in FIGS. 20A-20E, a fixation device 145 for use with the devices and systems disclosed herein comprises an elongated tubular body or tower 220, a slot 225 and a screw 240. The slot 225 may be a partial slot or an L-shaped slot that extends at least part of the length of the tower and has a rod receiving opening formed in the outer circumference of the tower. The slot 225 receives a rod 230 for fixation of the screw 240 into the vertebrae. The slot extends along at least part of the length of the tower such that the rod is still inserted at a height above the skin level of the patient while still providing a solid cylindrical profile for at least part of the length of the tower above the slot entrance. In use, the fixation device 145 of FIG. 20A is implanted or deployed into the lateral mass of consecutive vertebrae and the slots 225 are lined up to receive the rod 230 (FIG. 20B). The fixation rod 230 is introduced into the slot (FIG. 20C) and advanced or slid down the slot (FIG. 20D) until it is seated in the screw heads (FIG. 20E). Set screws are used to secure the rod. Once secured, the excess length of the tower ("tower extension") is cut or broken off while the fixation device remains in place.

All relative and directional references (including: upper, lower, upward, downward, left, right, leftward, rightward, top, bottom, side, above, below, front, middle, back, vertical, horizontal, and so forth) are given by way of example to aid the reader's understanding of the particular embodiments described herein. They should not be read to be requirements or limitations, particularly as to the position, orientation, or use unless specifically set forth in the claims. Connection references (e.g., attached, coupled, connected, joined, and the like) are to be construed broadly and may include intermediate members between a connection of elements and relative movement between elements. As such, connection references do not necessarily infer that two elements are directly connected and in fixed relation to each other, unless specifically set forth in the claims.

Although the invention has been disclosed in the context of certain embodiments and examples, the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A spinal fixation access and delivery system for accessing the cervical facet joint via a posterior access approach, the system comprising
    an access device comprising
        a body having a proximal portion and a distal portion; and
        a chamfered or beveled end feature positioned at the distal portion of the body and configured for insertion at the cervical facet joint,
    a guide device having access device engagement features; and
    a spinal fixation member,
    wherein the access device includes at least one guide device receiving feature complementary to or keyed to the engagement feature of the guide device, and
    the guide device comprises at least one spinal fixation member engagement feature, and
    the spinal fixation member includes at least one guide device receiving feature complementary to or keyed to the engagement feature of the guide device.

2. The system of claim 1 wherein the chamfered or beveled end feature of the access device is offset from the body.

3. The system of claim 1 wherein the chamfered or beveled end feature of the access device further includes a stop adapted to abut a posterior edge or posterior portion of the facet joint.

4. The system of claim 1 wherein the access device engagement features are selected from a protrusion, a notch or a recess.

5. The system of claim 1 further comprising a decortication tool.

6. The system of claim 1, wherein the spinal fixation member is a tower or a polyaxial screw with a tower feature.

7. The system of claim 1 wherein the at least one spinal fixation member engagement feature is a generally cylindrical body protruding from an outer surface of the guide device and generally extending the length of the guide device.

8. The system of claim 1, wherein the end feature comprises an articulating tip.

9. The system of claim 1, wherein the body is an elongated tubular body.

10. The system of claim 1, wherein the end feature comprises teeth or raised ridges.

\* \* \* \* \*